(12) United States Patent
Chikkanna et al.

(10) Patent No.: US 11,542,275 B2
(45) Date of Patent: Jan. 3, 2023

(54) SUBSTITUTED IMIDAZOLIDIN-2-ONE DERIVATIVES AS PRMT5 INHIBITORS

(71) Applicant: Aurigene Discovery Technologies Limited, Bangalore (IN)

(72) Inventors: Dinesh Chikkanna, Bangalore (IN); Sunil Kumar Panigrahi, Boudh (IN); Srinivasa Raju Sammeta, Bangalore (IN)

(73) Assignee: AURIGENE DISCOVERY TECHNOLOGIES LIMITED, Bangalore (IN)

( * ) Notice: Subject to any disclaimer, the term of this patent is extended or adjusted under 35 U.S.C. 154(b) by 2 days.

(21) Appl. No.: 16/982,800

(22) PCT Filed: Mar. 20, 2019

(86) PCT No.: PCT/IB2019/052252
§ 371 (c)(1),
(2) Date: Sep. 21, 2020

(87) PCT Pub. No.: WO2019/180631
PCT Pub. Date: Sep. 26, 2019

(65) Prior Publication Data
US 2021/0002298 A1   Jan. 7, 2021

(30) Foreign Application Priority Data
Mar. 22, 2018   (IN) .............. 201841010656

(51) Int. Cl.
| | |
|---|---|
| *C07D 498/08* | (2006.01) |
| *C07D 401/14* | (2006.01) |
| *C07D 405/14* | (2006.01) |
| *C07D 413/14* | (2006.01) |
| *C07D 471/08* | (2006.01) |
| *C07D 487/04* | (2006.01) |
| *C07D 491/107* | (2006.01) |
| *C07D 493/08* | (2006.01) |
| *C07D 495/04* | (2006.01) |

(52) U.S. Cl.
CPC ......... *C07D 498/08* (2013.01); *C07D 401/14* (2013.01); *C07D 405/14* (2013.01); *C07D 413/14* (2013.01); *C07D 471/08* (2013.01); *C07D 487/04* (2013.01); *C07D 491/107* (2013.01); *C07D 493/08* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 9,029,399 B2 | 5/2015 | Bock et al. | |
| 2014/0228394 A1 | 8/2014 | Bock et al. | |

FOREIGN PATENT DOCUMENTS

| | | |
|---|---|---|
| IN | 67/CHE/2012 | 1/2012 |
| WO | 2014100716 A1 | 6/2014 |
| WO | 2014100719 A2 | 6/2014 |
| WO | 2014100730 A1 | 6/2014 |
| WO | 2014100734 A1 | 6/2014 |
| WO | 2014100764 A2 | 6/2014 |
| WO | 2014108820 A1 | 7/2014 |
| WO | 2014128465 A1 | 8/2014 |
| WO | 2014145214 A2 | 9/2014 |
| WO | 2015200677 A2 | 12/2015 |
| WO | 2015200680 A2 | 12/2015 |
| WO | 2016022605 A1 | 2/2016 |
| WO | 2016034675 A1 | 3/2016 |
| WO | 2017153513 A1 | 9/2017 |
| WO | 2017153518 A1 | 9/2017 |
| WO | 2017211958 A1 | 12/2017 |

OTHER PUBLICATIONS

International Search Report issued in connection with PCT Application No. PCT/IB2019/052252 dated Jul. 18, 2019.
Kharkhanis et al., "Versatility of PRMT5-induced methylation in growth control and development," Trends Biochem Sciences, vol. 36, No. 12, 633-41, Dec. 2011.
Fabbrizio et al., "Negative regulation of transcription by the type II arginine methyltransferase PRMT5," EMBO Rep. 3, 641-645, May 27, 2002.
Yan et al., "Genetic validation of the protein arginine methyltransferase PRMT5 as a candidate therapeutic target in glioblastoma," Cancer Res. 74, 1752-1765, Mar. 15, 2014.
Nicholas et al., "PRMT5 is upregulated in malignant and metastatic melanoma and regulates expression of MITF and p27kip1," PLoS One, 30, vol. 8, Issue 9: e74710, Sep. 2013.
Bao et al., "Overexpression of PRMT5 promotes tumor cell growth and is associated with poor disease prognosis in epithelial ovarian cancer," Journal of Histochemistry and Cytochemistry, 61 (3), 206-217, 2013.
Gu et al., "Protein arginine methyltransferase 5 is essential for growth of lunch cancer cells," Biochem. J., 446, 235-41, 2012.
Pal et al., "Low levels of miR-92b/96 induce PRMT5 translation and H3R8/H4R3 methylation in mantle cell lymphoma," The EMBO Journal vol. 26, No. 15, 3558-69, 2007.
Wang et al., "Protein arginine methyltranserase 5 suppresses the transcription of the RB family of tumor suppressors in leukemia and lymphoma cells," Molecular and Cellular Biology, vol. 28, No. 20, 6262-6277, Aug. 11, 2008.
Jansson et al., "Arginine methylation regulates the p53 response," Nature Cell Biology, vol. 10, No. 12, 1431-1439, Dec. 2008.
Jin et al., "Targeting methyltransferase PRMT5 eliminates leukemia stem cells in chronic myelogenous leukemia" The Journal of Clinical Investigation, vol. 126, No. 10, 3961-3980, Oct. 2016.

(Continued)

*Primary Examiner* — Samantha L Shterengarts
(74) *Attorney, Agent, or Firm* — Dennemeyer & Associates; Steven M. Shape

(57) ABSTRACT

The present invention relates to substituted imidazolidin-2-one derivatives of formula (I) or pharmaceutically acceptable salts thereof. The present invention further provides the methods of preparation of compound of formula (I) and utility as PRMT5 inhibitors. The compounds are useful as medicaments in the treatment of conditions and disorders mediated by PRMT5, such as cancer, metabolic disorders, inflammation, autoimmune disease and hemoglobinopathies.

19 Claims, No Drawings

(56) References Cited

OTHER PUBLICATIONS

Chan-Penebre et al., "A selective inhibitor of PRMT5 with in vivo and in vitro potency in MCL models," Nature Chemical Biology, 432-437, Apr. 27, 2015.
Alinari et al., "Selective inhibition of protein arginine methyltransferase 5 blocks initiation and maintenance of B-cell transformation," Blood First Edition Paper 125, 2530-43, Mar. 11, 2015.
Antonia, et al. "Immuno-oncology combinations: a review of clinical experience and future prospects," Clinical Cancer Research 20:6258-6268, Oct. 23, 2014.
Melero, et al. "Evolving synergistic combinations of targeted immunotherapies to combat cancer," Nature Reviews Cancer, vol. 15, 457-472, Aug. 2015.

SUBSTITUTED IMIDAZOLIDIN-2-ONE DERIVATIVES AS PRMT5 INHIBITORS

CROSS-REFERENCE TO RELATED APPLICATIONS

This is a 35 U.S.C. 371 National Stage Patent Application of International Application No. PCT/IB2019/052252, filed Mar. 20, 2019, which claims priority to Indian application 201841010656, filed Mar. 22, 2018, each of which is hereby incorporated by reference in its entirety.

RELATED APPLICATIONS

This application claims the benefit of Indian provisional application number 201841010656, filed on Mar. 22, 2018; the specifications of which are hereby incorporated by reference in their entirety.

FIELD OF THE INVENTION

The present invention relates to therapeutically active substituted imidazolidin-2-one derivatives or pharmaceutically acceptable salts thereof or stereoisomers thereof which are useful in the treatment of PRMT5 dependent conditions and disorders. The present invention also relates to pharmaceutical compositions containing such compounds.

BACKGROUND OF THE INVENTION

Methyltransferase is an enzyme which catalyses the transfer of methyl group from one molecule to other. Protein methyltransferases (PMTs) are regulatory systems that regulate gene expression by transferring methyl groups to substrates including protein, DNA, RNA and small molecules. The transfer of methyl group to arginine residue of protein is catalysed by PRMT enzyme family which facilitates the transfer of methyl ($-CH_3$) group to specific nucleophilic sites on proteins, nucleic acids or other biomolecules. Methylation is an essential transformation in small-molecule metabolism and it is a common modification of DNA and RNA carried out by PMTs. Broadly, PMTs fall into two major families—protein lysine methyltransferases (PKMTs) and protein arginine methyltransferases (PRMTs). PRMTs utilize S-adenosyl-1-methionine (SAM) as a ubiquitous cofactor to catalyze the transfer of highly specific methyl group from methyl donor SAM to the arginine residues on different biological targets. Further, based on the products of the enzymatic reactions, PRMTs can be classified as type I-IV enzymes. Type I enzymes catalyze the formation of ω-NG-monomethylarginine (ωMMA) and asymmetric ω-NG, NG-dimethylarginine (ω-aDMA). Type II enzymes catalyze the formation of ωMMA and symmetric ω-NG, NG-dimethylarginine (ω-sDMA). Type III enzymes catalyze the formation of ωMMA only and Type IV enzymes catalyze the formation of 6-NG-MMA. Type I-III exist in mammalian cells and type IV is only described in yeast and possibly in plants. To date, ten PRMTs have been found in mammalian cells. PRMT 1, 2, 3, 4, 6 and 8 display type-I activity. PRMT 5, 7 and 9 display type-II activity. In addition to type-II activity, PRMT 7 also displays type-III activity.

Protein arginine methyltransferase 5 (PRMT5) is a typical type II methyltransferase, transferring methyl groups from SAM to the two w-guanidino nitrogen atoms of arginine, leading to ω-NG, NG-di-symmetric methylation of a protein substrate. It is localized in both the nucleus and the cytoplasm and performs distinct functions by modifying either histones or non-histone proteins. PRMT5 was initially identified as Janus kinase (JAK)-binding protein 1 (JBP1). It can symmetrically methylate histones H2AR3, H3R2, H3R8 and H4R3. PRMT5 can also methylate many non-histone proteins and many of these events are involved in tumorigenesis. PRMT5 also plays an important role in cell cycle progression and the DNA repair process. PRMT5 has been implicated in the regulation of cell growth, apoptosis and inflammation. PRMT5 interacts with a number of binding partners that influence its substrate specificity. MEP50, a member of the WD40 family of proteins, is a critical PRMT5 cofactor which directly binds PRMT5 and increases histone methyltransferase activity of PRMT5. Nuclear PRMT5 forms complexes with the chromatin-remodeling complexes (hSWI/SNF, NuRD) and epigenetically controls genes involved in development, cell proliferation and differentiation, including tumor suppressor, through methylation of histones (Kharkhanis et al. *Trends Biochem Sci.* 36, 633-41, 2011). Fabbrizio, E. et al. showed that PRMT5 is a transcriptional repressor (Fabbrizio et al., *EMBO Rep.* 3, 641-645, 2002). H3R8me2s and H4R3me2s are keys in repressive histone methylation. Hence as a transcriptional repressor PRMT5 has oncogene-like properties because of its ability to repress the expression of tumour suppressor genes. It is shown that PRMT5 overexpression correlates with human glioblastoma cell proliferation and inversely correlates with patient survival (Yan et al., *Cancer Res.* 74, 1752-1765, 2014). It is reported that PRMT5 is unregulated in human malignant melanoma tumors compared to normal epidermis (Nicholas et al., *PLoS One,* 30, 8(9): e74710, 2013). It is shown that depletion of PRMT5 via siRNA modulates cellular proliferation in ovarian cancer cell line (Bao et al., *J. Histochem. Cytochem.,* 61, 206-217, 2013). Gu et al. showed that PRMT5 expression is essential for the growth of lung cancer cells (Gu et al. *Biochem.* 1, 446, 235-41, 2012). Pal et al. and Wang et al. reported that PRMT5 levels are elevated in various transformed cells and knockdown of PRMT5 is associated with a slowing of cell growth, whereas PRMT5 overexpression causes cellular hyperproliferation (Pal et al., *EMBO J.* 8, 26, 3558-69, 2007 and Wang et al., *Mol. Cell. Biol.,* 28, 6262-6277, 2008). Jansson et al. reported that PRMT5 overexpression in an orthotopic mouse model of breast cancer accelerates tumour growth (Jansson et al., *Nature Cell Biol,* 10, 1431-1439, 2008). PRMT5 suppresses the transcription of the Rb family of tumor suppressors in leukemia and lymphoma cells (Wang et al., *Mol. Cell. Biol.,* 28, 6262-6277, 2008). Several cell lines and patient samples in B-cell lymphoma and leukemia shows PRMT5 overexpression (Pal et al., *EMBO J.* 8, 26, 3558-69, 2007). Targeting methyltransferase PRMT5 eliminates leukemia stem cells in chronic myelogenous leukemia (Jin et al., *J. Clin. Invest.,* 126, 3961-3980, 2016; Yan et al., *Cancer Res.,* 74, 1752-1765, 2014 and Chan-Penebre et al., *Nature Chemical Biology,* 11, 432-437, 2015). Selective inhibition of PRMT5 blocks initiation and maintenance of B-cell transformation (Alinari et al., *Blood,* 125, 2530-43, 2015). In addition to glioblastoma, melanoma, ovarian and lung cancer, PRMT5 is also implicated in other solid tumors such as prostate cancer, breast cancer, colon cancer, gastric cancer, esophageal cancer and hepatocellular carcinoma. Additionally aberrant methylation of PRMT5 substrates has been implicated in other indications such as metabolic disorders, inflammation, autoimmune disease and hemoglobinopathies.

Few PRMT5 inhibitors have been described in e.g. WO2017/211958, WO 2017/153518, WO 2017/153513, WO 2016/034675, WO 2016/022605, WO 2015/200677, WO 2015/200680, WO 2014/145214, WO2014/128465, WO2014/100764, WO 2014/100734, WO 2014/100730, WO 2014/100719 and WO 2014/100716.

Nevertheless, there is a need for potent and selective PRMT5 inhibitors which are suitable for use as a medicament in the treatment of conditions and disorders, where PRMT5 inhibition is desired, such as cancer, metabolic disorders, inflammation, autoimmune disease and hemoglobinopathies.

SUMMARY OF THE INVENTION

It has been found that compounds of formula (I) are potent and selective PRMT5 inhibitors. The compounds of the invention are therefore useful as medicaments in the treatment of cancer, such as glioblastoma, melanoma, ovarian cancer, lung cancer, prostate cancer, breast cancer, colon cancer, gastric cancer, esophageal cancer, hepatocellular carcinoma, and other conditions and disorders mediated by PRMT5, such as metabolic disorders, inflammation, autoimmune disease and hemoglobinopathies.

In one aspect, the present invention provides compound of formula (I):

or a pharmaceutically acceptable salt thereof or a stereoisomer thereof;
wherein,
each $X_1$, $X_2$ and $X_3$ are independently $CR_5$ or N;
ring A is cycloalkyl, aryl, heterocycloalkyl or heteroaryl;
R is hydrogen, alkyl or halo;
$R_1$ is $R_2$ is hydrogen or alkyl;
alternatively, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more $R_6$;
$R_3$ is hydrogen or alkyl;
$R_4$ at each occurrence independently is hydrogen, halo, haloalkyl, cyano, alkyl, alkenyl, alkynyl, hydroxy, alkoxy, —C(O)$R_7$, -alkyl-C(O)$R_7$, —S(O)$_2R_7$; wherein the said alkyl, alkenyl and alkynyl are optionally substituted with 1 to 3 groups selected from hydroxyl, halo, heterocycloalkyl and heteroaryl;
alternatively, two $R_4$ on the same atom together form an oxo (=O) group;
$R_5$ at each occurrence independently is hydrogen, alkyl, halo, haloalkyl or alkoxy;
$R_6$ is alkyl, alkoxy, hydroxy, cyano, halo or haloalkyl;
$R_7$ is alkyl, hydroxy, alkoxy, —$NR_eR_f$, cycloalkyl, aryl, heterocycloalkyl or heteroaryl;
wherein each alkyl, cycloalkyl, aryl, heterocycloalkyl and heteroaryl is further optionally substituted by one or more $R_6$;
$R_a$ and $R_b$ each independently are hydrogen or alkyl;
$R_c$ and $R_d$ each independently are hydrogen or alkyl;
alternatively $R_c$ and $R_d$ together represent an oxo (=O) group;
$R_e$ and $R_f$ each independently are hydrogen or alkyl;
alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;
'm' is an integer from 1 to 3; and
'n' is 0 or 1.

In yet another aspect, the present invention provides a pharmaceutical composition comprising a compound of formula (I) or a pharmaceutically acceptable salt thereof and at least one pharmaceutically acceptable excipient (such as a pharmaceutically acceptable carrier or diluent).

In yet another aspect, the present invention relates to the preparation of compound of formula (I).

In yet another aspect of the present invention, provided herein are substituted imidazolidin-2-one derivatives of formula (I), which are useful as PRMT5 inhibitors and therapeutic use thereof.

DETAILED DESCRIPTION OF THE INVENTION

The present invention provides substituted imidazolidin-2-one derivatives as compounds of formula (I), which are useful as PRMT5 inhibitors. The present invention further provides pharmaceutical compositions comprising the said compounds and their derivatives as therapeutic agents.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus it is intended that the present invention include such modifications and variations and their equivalents. Other objects, features and aspects of the present invention are disclosed in or are obvious from the following detailed description. It is to be understood by one of ordinary skill in the art that the present invention is a description of exemplary embodiments only and is not to be construed as limiting the broader aspects of the invention.

In one aspect, the present invention provides compound of formula (I):

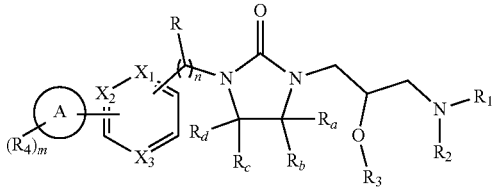

(I)

or a pharmaceutically acceptable salt thereof or a stereoisomer thereof;
wherein,
  each $X_1$, $X_2$ and $X_3$ are independently $CR_5$ or N;
  ring A is cycloalkyl, aryl, heterocycloalkyl or heteroaryl;
  R is hydrogen, alkyl or halo;
  $R_1$ is

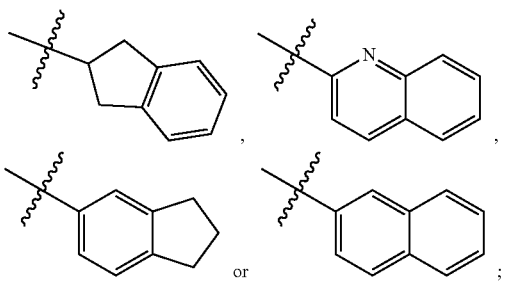

or ;

$R_2$ is hydrogen or alkyl;
alternatively, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more $R_6$;
$R_3$ is hydrogen or alkyl;
$R_4$ at each occurrence independently is hydrogen, halo, haloalkyl, cyano, alkyl, alkenyl, alkynyl, hydroxy, alkoxy, $-C(O)R_7$, -alkyl-$C(O)R_7$, $-S(O)_2R_7$; wherein the said alkyl, alkenyl and alkynyl are optionally substituted with 1 to 3 groups selected from hydroxyl, halo, heterocycloalkyl and heteroaryl;
alternatively, two $R_4$ on the same atom together form an oxo (=O) group;
$R_5$ at each occurrence independently is hydrogen, alkyl, halo, haloalkyl or alkoxy;
$R_6$ is alkyl, alkoxy, hydroxy, cyano, halo or haloalkyl;
$R_7$ is alkyl, hydroxy, alkoxy, $-NR_eR_f$, cycloalkyl, aryl, heterocycloalkyl or heteroaryl; wherein each alkyl, cycloalkyl, aryl, heterocycloalkyl and heteroaryl is further optionally substituted by one or more $R_6$;
$R_a$ and $R_b$ each independently are hydrogen or alkyl;
$R_c$ and $R_d$ each independently are hydrogen or alkyl; alternatively $R_c$ and $R_d$ together represent an oxo (=O) group;
$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;
'm' is an integer from 1 to 3; and
'n' is 0 or 1.

In another aspect, the present invention provides compound of formula (I'):

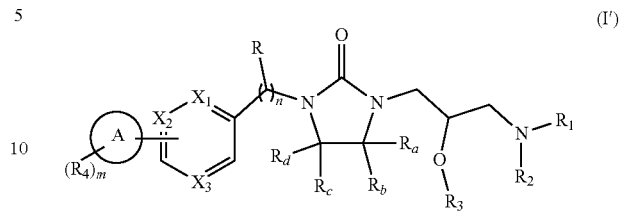

(I')

or a pharmaceutically acceptable salt thereof or a stereoisomer thereof;
wherein,
  each $X_1$, $X_2$ and $X_3$ are independently $CR_5$ or N;
  ring A is cycloalkyl, aryl, heterocycloalkyl or heteroaryl;
  R is hydrogen, alkyl or halo;
  $R_1$ is

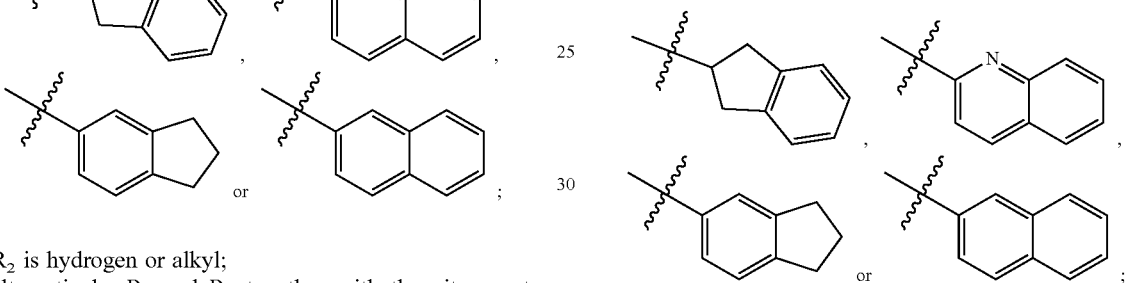

or ;

$R_2$ is hydrogen or alkyl;
alternatively, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more $R_6$;
$R_3$ is hydrogen or alkyl;
$R_4$ at each occurrence independently is hydrogen, halo, haloalkyl, cyano, alkyl, alkenyl, alkynyl, hydroxy, alkoxy, $-C(O)R_7$, -alkyl-$C(O)R_7$, $-S(O)_2R_7$; wherein the said alkyl, alkenyl and alkynyl are optionally substituted with 1 to 3 groups selected from hydroxyl, halo, heterocycloalkyl and heteroaryl;
alternatively, two $R_4$ on the same atom together form an oxo (=O) group;
$R_5$ at each occurrence independently is hydrogen, alkyl, halo, haloalkyl or alkoxy;
$R_6$ is alkyl, alkoxy, hydroxy, cyano, halo, or haloalkyl;
$R_7$ is alkyl, hydroxy, alkoxy, $-NR_eR_f$, cycloalkyl, aryl, heterocycloalkyl or heteroaryl; wherein each alkyl, cycloalkyl, aryl, heterocycloalkyl and heteroaryl is further optionally substituted by one or more $R_6$;
$R_a$ and $R_b$ each independently are hydrogen or alkyl;
$R_c$ and $R_d$ each independently are hydrogen or alkyl; alternatively $R_c$ and $R_d$ together represent an oxo (=O) group;
$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;

'm' is an integer from 1 to 3; and
'n' is 0 or 1.

In another aspect, the present invention provides compounds of formula (I) or a pharmaceutically acceptable salt thereof or a stereoisomer thereof; wherein, each $X_1$, $X_2$ and $X_3$ are independently $CR_5$ or N;

ring A is $C_3$-$C_{10}$ cycloalkyl, $C_6$-$C_{10}$ aryl, 5-12 membered heterocycloalkyl or 5-12 membered heteroaryl;

R is hydrogen, alkyl or halo;

$R_1$ is

[chemical structures]

or

[chemical structures];

$R_2$ is hydrogen or alkyl;

alternatively, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more $R_6$;

$R_3$ is hydrogen or alkyl;

$R_4$ at each occurrence independently is hydrogen, halo, haloalkyl, cyano, alkyl, alkenyl, alkynyl, hydroxy, alkoxy, —C(O)$R_7$, -alkyl-C(O)$R_7$, —S(O)$_2R_7$; wherein the said alkyl, alkenyl and alkynyl are optionally substituted with 1 to 3 groups selected from hydroxyl, halo, heterocycloalkyl and heteroaryl;

alternatively, two $R_4$ on the same atom together form an oxo (=O) group;

$R_5$ at each occurrence independently is hydrogen, alkyl, halo, haloalkyl or alkoxy;

$R_6$ is alkyl, alkoxy, hydroxy, cyano, halo, or haloalkyl;

$R_7$ is alkyl, hydroxy, alkoxy, —NR$_e$R$_f$, cycloalkyl, aryl, heterocycloalkyl or heteroaryl; wherein each alkyl, cycloalkyl, aryl, heterocycloalkyl and heteroaryl is further optionally substituted by one or more $R_6$;

$R_a$ and $R_b$ each independently are hydrogen or alkyl;

$R_c$ and $R_d$ each independently are hydrogen or alkyl; alternatively $R_c$ and $R_d$ together represent an oxo (=O) group;

$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;

'm' is an integer from 1 to 3; and
'n' is 0 or 1.

In certain embodiments, the present invention provides compound of formula (I), wherein, each $X_1$, $X_2$ and $X_3$ are independently $CR_5$ or N;

ring A is $C_3$-$C_{10}$ cycloalkyl, $C_6$-$C_{10}$ aryl, 5-12 membered heterocycloalkyl or 5-12 membered heteroaryl;

R is hydrogen, alkyl or halo;

The group

[chemical structures]

is

[chemical structures],

[chemical structures], or

[chemical structures];

wherein each bicyclic heterocyclyl ring is optionally substituted by one or more $R_6$;

$R_3$ is hydrogen or alkyl;

$R_4$ at each occurrence independently is hydrogen, halo, haloalkyl, cyano, alkyl, alkenyl, alkynyl, hydroxy, alkoxy, —C(O)$R_7$, -alkyl-C(O)$R_7$, —S(O)$_2R_7$; wherein the said alkyl, alkenyl and alkynyl are optionally substituted with 1 to 3 groups selected from hydroxyl, halo, heterocycloalkyl and heteroaryl;

alternatively, two $R_4$ on the same atom together form an oxo (=O) group;

$R_5$ at each occurrence independently is hydrogen, alkyl, halo, haloalkyl or alkoxy;

$R_6$ is alkyl, alkoxy, hydroxy, cyano, halo, or haloalkyl;

$R_7$ is alkyl, hydroxy, alkoxy, —NR$_e$R$_f$, cycloalkyl, aryl, heterocycloalkyl or heteroaryl; wherein each alkyl, cycloalkyl, aryl, heterocycloalkyl and heteroaryl is further optionally substituted by one or more $R_6$;

$R_a$ and $R_b$ each independently are hydrogen or alkyl;

$R_c$ and $R_d$ each independently are hydrogen or alkyl; alternatively $R_c$ and $R_d$ together represent an oxo (=O) group;

$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;

'm' is an integer from 1 to 3; and
'n' is 0 or 1.

In another aspect, the present invention provides compound of formula (I) or a pharmaceutically acceptable salt thereof or a stereoisomer thereof; wherein, ring A is a 3-10 membered monocyclic ring system or a 6- to 12-membered bicyclic ring selected from fused, bridged and spirocyclic ring systems.

In another aspect, the present invention provides compounds of formula (I) or a pharmaceutically acceptable salt thereof or a stereoisomer thereof; wherein, $R_4$ at each occurrence independently is hydrogen, halo, haloalkyl, cyano, alkyl, hydroxy, alkoxy, —C(O)$R_7$, -alkyl-C(O)$R_7$ or —S(O)$_2R_7$; wherein the said alkyl is further optionally substituted by heterocycloalkyl or heteroaryl.

In certain embodiments, the present invention provides compounds of formula (I), wherein, R is hydrogen and n is 1.

In certain embodiments, the present invention provides compounds of formula (IA),

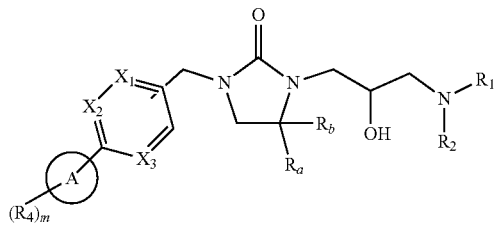

(IA)

or a pharmaceutically acceptable salt thereof or a stereoisomer thereof;
wherein, ring A, $X_1$, $X_2$, $X_3$, $R_1$, $R_2$, $R_4$, $R_a$, $R_b$ and m are same as defined in formula (I)

In certain embodiments, the present invention provides compounds of formula (TB),

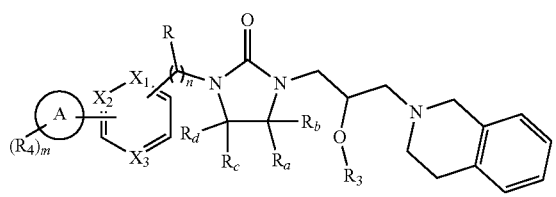

(IB)

or a pharmaceutically acceptable salt thereof or a stereoisomer thereof;
wherein, ring A, $X_1$, $X_2$, $X_3$, $R_3$, $R_4$, $R_a$, $R_b$, $R_c$, $R_d$, and m are same as defined in formula (I).

In certain embodiments, the present invention provides compounds of formula (IC),

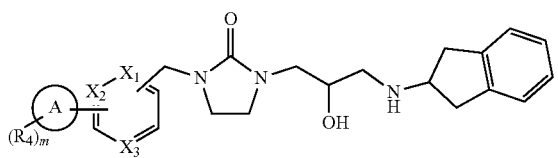

(IC)

or a pharmaceutically acceptable salt thereof or a stereoisomer thereof;
wherein, ring A, $X_1$, $X_2$, $X_3$, $R_4$ and m are same as defined in formula (I).

In certain embodiments, the present invention provides compounds of formula (ID),

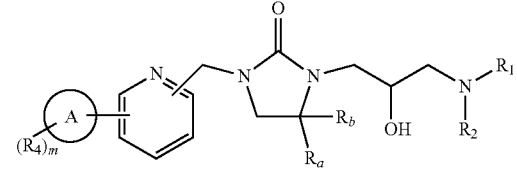

(ID)

or a pharmaceutically acceptable salt thereof or a stereoisomer thereof;
wherein, ring A, $R_1$, $R_2$, $R_4$, $R_a$, $R_b$ and m are same as defined in formula (I).

In certain embodiments, the present invention provides compounds of formula (IE),

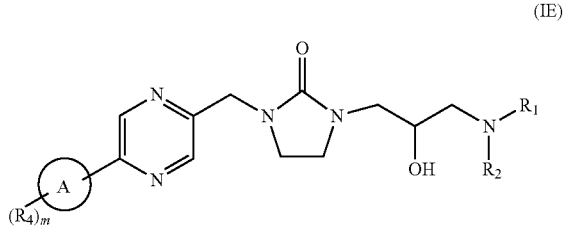

(IE)

or a pharmaceutically acceptable salt thereof or a stereoisomer thereof;
wherein, ring A, $R_1$, $R_2$, $R_4$ and m are same as defined in formula (I).

In certain embodiments, the present invention provides compounds of formula (IF),

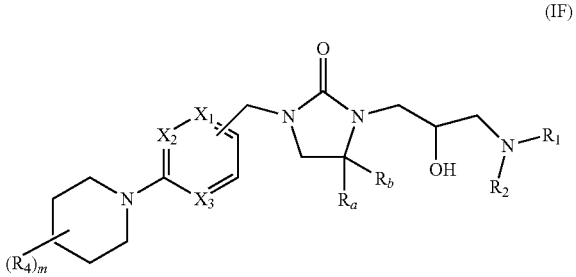

(IF)

or a pharmaceutically acceptable salt thereof or a stereoisomer thereof;
wherein, $X_1$, $X_2$, $X_3$, $R_1$, $R_2$, $R_4$, $R_a$, $R_b$ and m are same as defined in formula (I).

In certain embodiments, the present invention provides compounds of formula (IG),

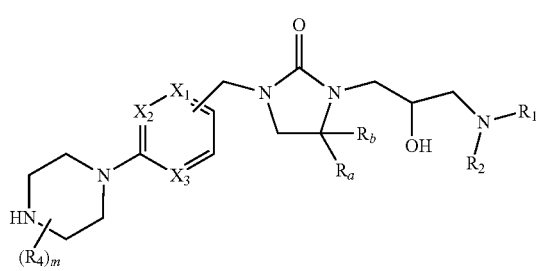

(IG)

or a pharmaceutically acceptable salt thereof or a stereoisomer thereof;
wherein, $X_1$, $X_2$, $X_3$, $R_1$, $R_2$, $R_4$, $R_a$, $R_b$ and m are same as defined in formula (I).

In certain embodiments, the present invention provides compounds of formula (IH),

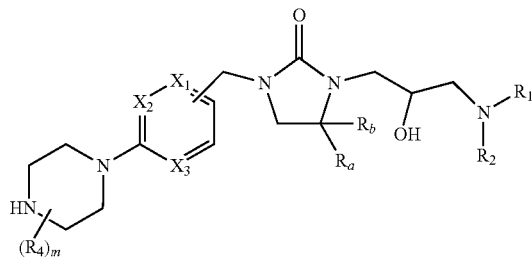

(IG)

or a pharmaceutically acceptable salt thereof or a stereoisomer thereof;

wherein, $X_1$, $X_2$, $X_3$, $R_1$, $R_2$, $R_4$, $R_a$, $R_b$ and m are same as defined in formula (I).

In certain embodiments, the present invention provides compounds of formula (Ii),

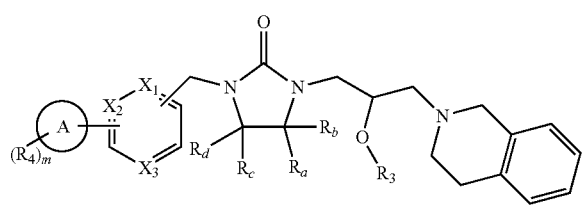

(Ii)

or a pharmaceutically acceptable salt thereof or a stereoisomer thereof; wherein, A, $X_1$, $X_2$, $X_3$, $R_a$, $R_b$, $R_c$, $R_d$, $R_3$, $R_4$ and m are same as defined in formula (I).

In certain embodiments, the present invention provides compounds of formula (Ii), wherein each $X_1$, $X_2$ and $X_3$ are independently $CR_5$ or N;

ring A is heterocycloalkyl or heteroaryl;

$R_3$ is hydrogen or alkyl;

$R_4$ at each occurrence independently is hydrogen, halo, haloalkyl, cyano, alkyl, —C(O)$R_7$, -alkyl-C(O)$R_7$, —S(O)$_2$$R_7$; wherein the said alkyl is optionally substituted with 1 to 3 groups selected from hydroxyl, halo, heterocycloalkyl and heteroaryl; alternatively, two $R_4$ on the same atom together form an oxo (=O) group;

$R_5$ at each occurrence independently is hydrogen, alkyl, or halo;

$R_6$ is alkyl, alkoxy, hydroxy, cyano, halo or haloalkyl;

$R_7$ is alkyl, hydroxy, alkoxy, —$NR_eR_f$, cycloalkyl, heterocycloalkyl or heteroaryl; wherein each alkyl, cycloalkyl, aryl, heterocycloalkyl and heteroaryl is further optionally substituted by one or more $R_6$;

$R_a$ and $R_b$ each independently are hydrogen or alkyl;

$R_c$ and $R_d$ each independently are hydrogen or alkyl; alternatively $R_c$ and $R_d$ together represent an oxo (=O) group;

$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;

'm' is an integer from 1 to 3.

In certain embodiments, the present invention provides compounds of formula (IJ),

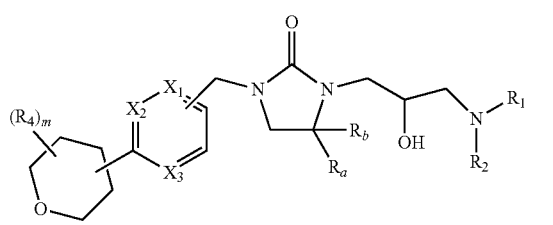

(IJ)

or a pharmaceutically acceptable salt thereof or a stereoisomer thereof;

wherein, $X_1$, $X_2$, $X_3$, $R_1$, $R_2$, $R_4$, $R_a$, $R_b$ and m are same as defined in formula (I).

In certain embodiments, the present invention provides compounds of formula (IK),

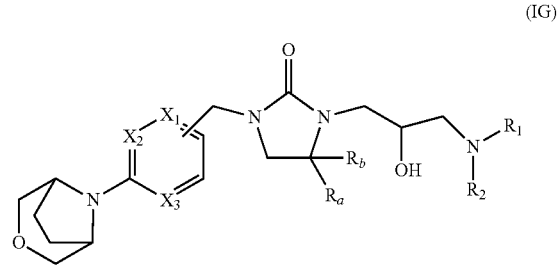

(IG)

or a pharmaceutically acceptable salt thereof or a stereoisomer thereof;

wherein, $X_1$, $X_2$, $X_3$, $R_1$, $R_2$, $R_a$ and $R_b$ are same as defined in formula (I).

In certain embodiments, the present invention provides compounds of formula (IL),

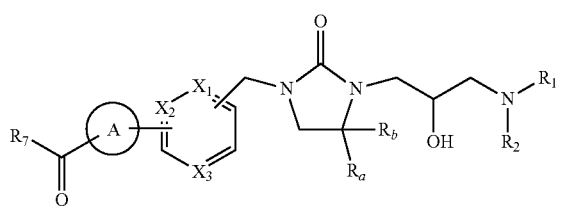

(IL)

or a pharmaceutically acceptable salt thereof or a stereoisomer thereof;

wherein, ring A, $X_1$, $X_2$, $X_3$, $R_1$, $R_2$, $R_7$, $R_a$ and $R_b$ are same as defined in formula (I).

In certain embodiments, the present invention provides compounds of formula (I), or a pharmaceutically acceptable salt thereof or a stereoisomer thereof;

wherein
each $X_1$, $X_2$ and $X_3$ are independently $CR_5$ or N;
ring A is 3- to 10-membered heterocycloalkyl or 3- to 10-membered heteroaryl;
R is hydrogen, alkyl or halo;
$R_1$ is

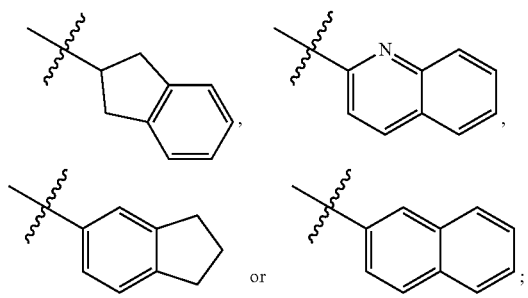

$R_2$ is hydrogen or alkyl; alternatively, $R_1$ and $R_2$ together with the nitrogen to which they are attached form a bicyclic heterocyclyl ring optionally containing 1 to 2 additional heteroatoms selected from N, O and S; wherein the bicyclic heterocyclyl ring is optionally substituted by one or more $R_6$;

$R_3$ is hydrogen or alkyl;

$R_4$ at each occurrence independently is hydrogen, halo, haloalkyl, cyano, alkyl, —C(O)$R_7$, -alkyl-C(O)$R_7$, —S(O)$_2$ $R_7$; wherein the said alkyl is optionally substituted with 1 to 3 groups selected from hydroxyl, halo, 3- to 10-membered heterocycloalkyl and 3- to 10-membered heteroaryl; alternatively, two $R_4$ on the same atom together form an oxo (=O) group;

$R_5$ at each occurrence independently is hydrogen, alkyl, or halo;

$R_6$ is alkyl, alkoxy, hydroxy, cyano, halo or haloalkyl;

$R_7$ is alkyl, hydroxy, alkoxy, —N$R_e R_f$ 3- to 10-membered cycloalkyl, 3- to 8-membered heterocycloalkyl or 3- to 10-membered heteroaryl; wherein each alkyl, cycloalkyl, aryl, heterocycloalkyl and heteroaryl is further optionally substituted by one or more $R_6$;

$R_a$ and $R_b$ each independently are hydrogen or alkyl;

$R_c$ and $R_d$ each independently are hydrogen or alkyl; alternatively $R_c$ and $R_d$ together represent an oxo (=O) group;

$R_e$ and $R_f$ each independently are hydrogen or alkyl; alternatively, $R_e$ and $R_f$ together with the nitrogen to which they are attached form an optionally substituted 3- to 7-membered heterocyclic ring with 1 to 2 additional heteroatoms selected from N, O and S; wherein the optional substituent is one or more $R_6$;

'm' is an integer from 1 to 3; and 'n' is 0 or 1.

In certain other embodiments, the present invention provides compounds of formula (I), wherein, ring

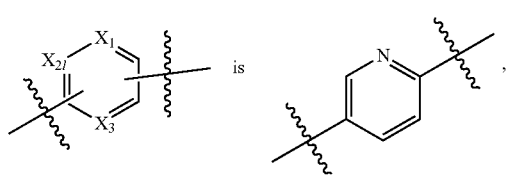

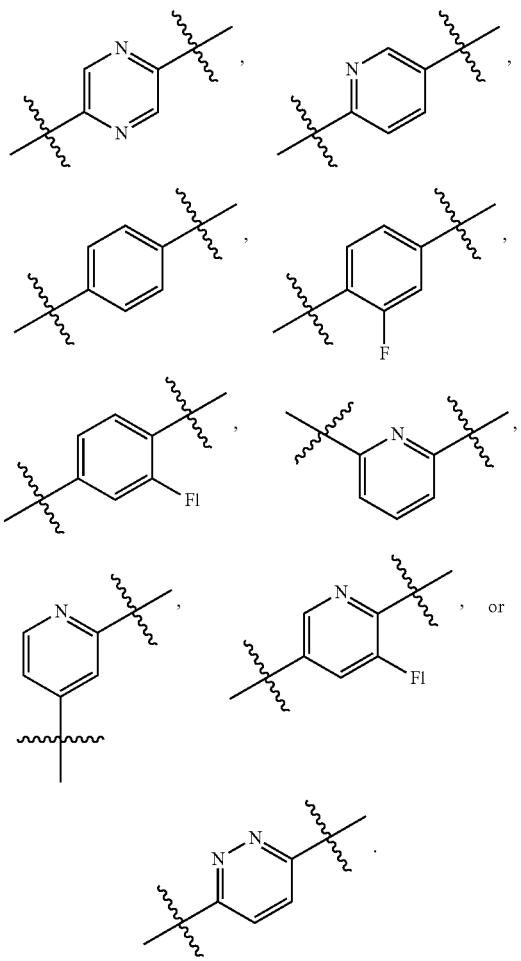

In certain embodiments, ring A is a 3-10 membered monocyclic ring system.

According to the preceding embodiment, the monocyclic ring system is a carbocyclyl or a heterocyclyl ring system.

In certain embodiments, ring A is a 6- to 12-membered bicyclic ring selected from fused, bridged and spirocyclic ring systems.

According to the preceding embodiment, the bicyclic ring system is a carbocyclyl or a heterocyclyl ring system.

In certain embodiments, ring A is

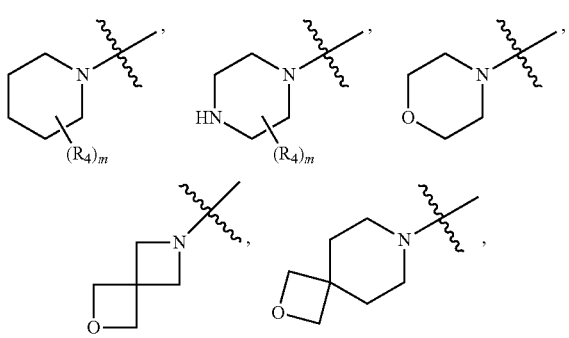

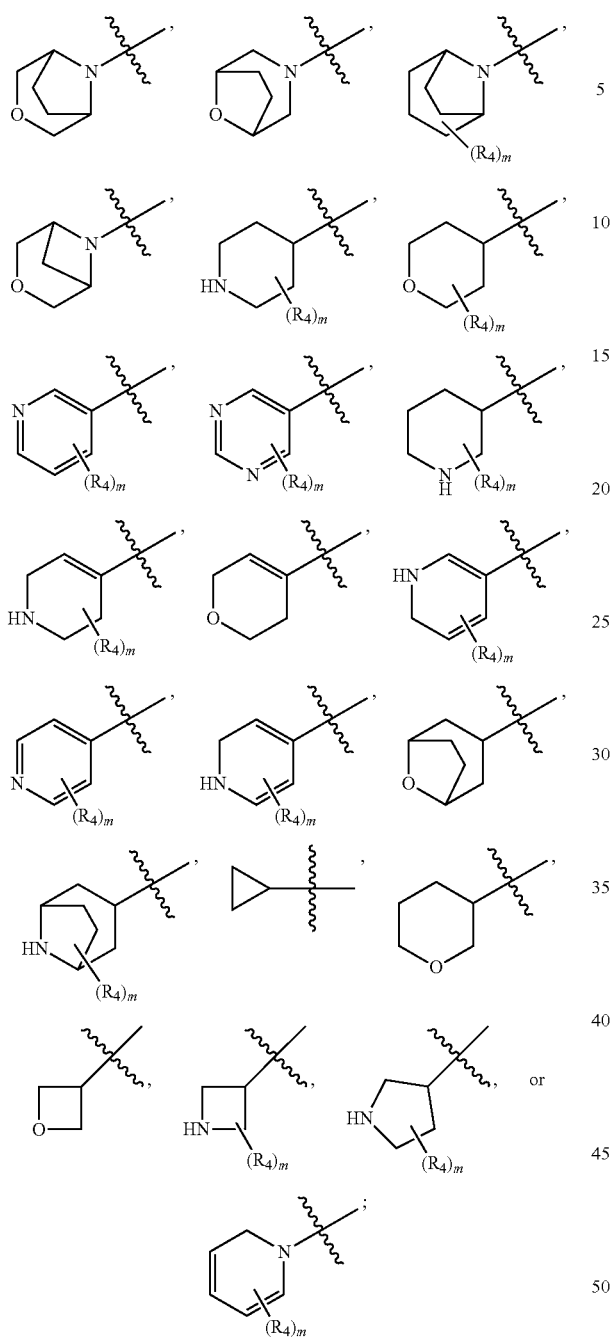
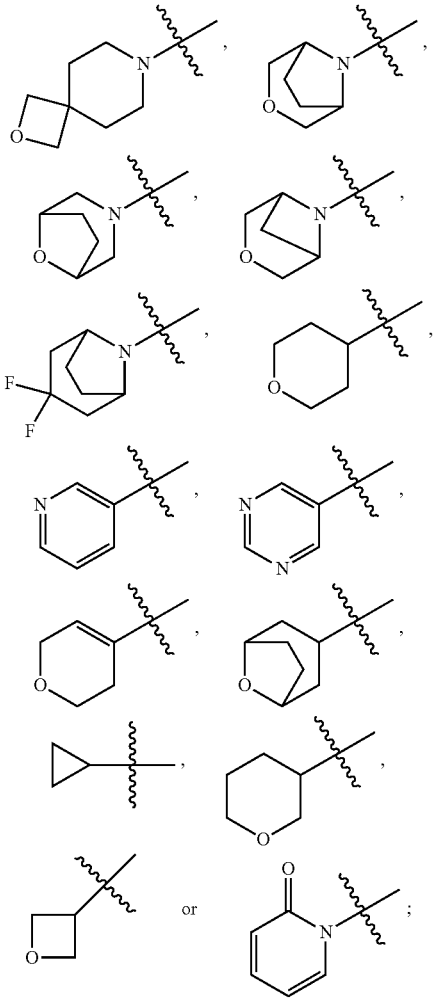
wherein 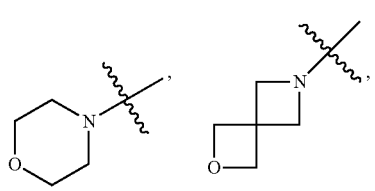 is the point of attachment with ring having $X_1$, $X_2$ and $X_3$.
In certain embodiments, ring A is
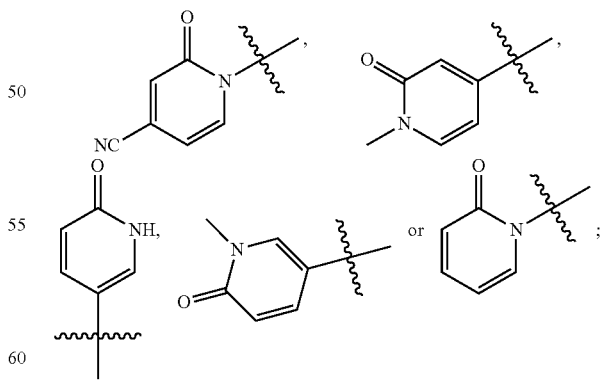
wherein 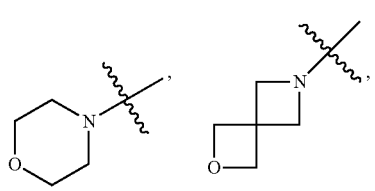 is the point of attachment with ring having $X_1$, $X_2$ and $X_3$.
In certain embodiments, each $X_1$, $X_2$ and $X_3$ are $CR_5$; or $X_1$ is N, $X_2$ and $X_3$ are $CR_5$; or $X_2$ is N, $X_1$ and $X_3$ are $CR_5$;

or $X_2$ is $CR_5$, $X_1$ and $X_3$ are N; or $X_1$ is $CR_5$, $X_2$ and $X_3$ are N; or each $X_1$, $X_2$ and $X_3$ are N; or $X_3$ is $CR_5$, $X_1$ and $X_2$ are N.

In certain embodiments, each $X_1$, $X_2$ and $X_3$ are $CR_5$; $X_1$ is N, $X_2$ and $X_3$ are $CR_5$; or $X_2$ is N, $X_1$ and $X_3$ are $CR_5$; or $X_1$ is $CR_5$, $X_2$ and $X_3$ are N; or $X_2$ is $CR_5$, $X_1$ and $X_3$ are N; or $X_3$ is $CR_5$, $X_1$ and $X_2$ are N.

In certain embodiments, each $X_1$, $X_2$ and $X_3$ are $CR_5$; wherein $R_5$ is hydrogen.

In certain embodiments, each $X_1$, $X_2$ and $X_3$ are $CR_5$; wherein $R_5$ independently is halo or alkoxy.

In certain embodiments, $R_1$ is

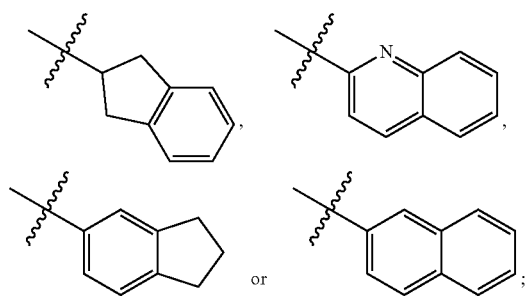

and $R_2$ is hydrogen.

In certain embodiments, the group

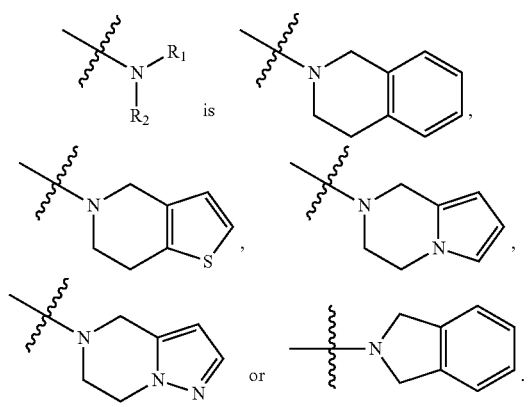

In certain embodiments, the group

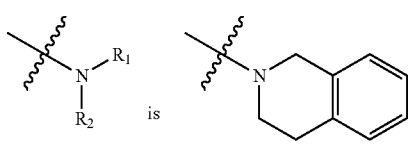

optionally substituted by one or more halo or alkoxy.

In certain embodiments, the group

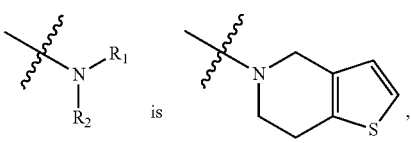

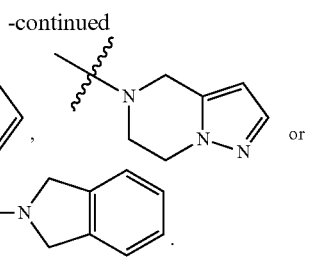

In certain embodiments, $R_3$, $R_a$, $R_b$, $R_c$ and $R_d$ are each hydrogen.

In certain embodiments, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more halo or alkoxy.

In certain embodiments, $R_2$ is hydrogen.
In certain embodiments, $R_3$ is hydrogen.
In certain embodiments, $R_4$ at each occurrence is hydrogen.
In certain embodiments, $R_4$ is acyl.
In certain embodiments, $R_4$ at each occurrence independently is hydrogen, halo, haloalkyl, cyano, alkyl, hydroxy or alkoxy; wherein the said alkyl is optionally substituted with 1 to 3 groups selected from hydroxyl, halo, heterocycloalkyl and heteroaryl.

In certain embodiments, $R_4$ at each occurrence independently is $-C(O)R_7$, -alkyl-$C(O)R_7$ or $-S(O)_2R_7$; wherein $R_7$ is selected from alkyl, alkoxy, $-NR_eR_f$, cycloalkyl or heterocycloalkyl; wherein each alkyl, cycloalkyl and heterocycloalkyl is further optionally substituted by one or more $R_6$.

In certain embodiments, $R_4$ at each occurrence independently is hydrogen, halo, $-C(O)R_7$, -alkyl-$C(O)R_7$ or $-S(O)_2R_7$,

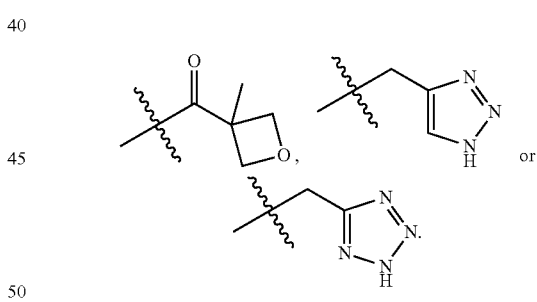

In certain embodiments, two $R_4$ on the same atom together form an oxo (=O) group.

In certain embodiments, $R_4$ is $-C(CH_3)_2-COOH$ or $-C(CH_3)_2-COOCH_2CH_3$.

In certain embodiments, $R_5$ at each occurrence independently is hydrogen, alkyl or halo.

In certain embodiments, $R_5$ independently is hydrogen or fluoro.

In certain embodiments, $R_6$ at each occurrence independently is alkyl, alkoxy or halo.

In certain embodiments, $R_7$ is alkyl, hydroxy, alkoxy or $-NR_eR_f$, each optionally substituted by one or more $R_6$.

In certain embodiments, $R_7$ is optionally substituted cycloalkyl or optionally substituted heterocycloalkyl; wherein the optional substituent is selected from one or more $R_6$.

In certain embodiments, $R_a$, $R_b$, $R_c$ and $R_d$ are each hydrogen.

In certain embodiments, $R_c$ and $R_d$ together represent an oxo (=O) group.

In certain embodiments, $R_e$ and $R_f$ together with the nitrogen to which they are attached form an optionally substituted 3 to 7 membered heterocyclic ring with 1 to 2 additional heteroatoms selected from N, O and S; wherein the optional substituent is independently selected from alkyl, alkoxy, hydroxy, cyano and halo.

In certain embodiments, $R_e$ and $R_f$ are each alkyl; wherein the alkyl is methyl.

In certain embodiments, 'n' is 0. In certain embodiments of the present invention, if 'n' is 0, then ring having $X_1$, $X_2$ and $X_3$ is directly attached to central imidazolidinone ring containing $R_a$ to $R_d$ as described in compound of formula (I).

In certain embodiments, m is at least 2 for an oxo substitution.

In certain embodiments, n is 1.

In certain embodiments, the present invention provides a compound or a pharmaceutically acceptable salt or a stereoisomer thereof, selected from:

| Comp. No | IUPAC Name |
|---|---|
| 1 | (R)-1-(3-(3,4-dihydroisoquinolin-2(1H)-yl)-2-hydroxypropyl)-3-((5-(4-(pyrrolidine-1-carbonyl)piperidin-1-yl)pyridin-2-yl)methyl)imidazolidin-2-one; |
| 2 | (R)-1-((5-(4-acetylpiperazin-1-yl)pyrazin-2-yl)methyl)-3-(3-(3,4-dihydroisoquinolin-2(1H)-yl)-2-hydroxypropyl)imidazolidin-2-one; |
| 3 | (R)-1-((5-(4-acetylpiperazin-1-yl)pyridin-2-yl)methyl)-3-(3-(3,4-dihydroisoquinolin-2(1H)-yl)-2-hydroxypropyl)imidazolidin-2-one; |
| 4 | (R)-1-(3-(3,4-dihydroisoquinolin-2(1H)-yl)-2-hydroxypropyl)-3-((5-morpholinopyridin-2-yl)methyl)imidazolidin-2-one; |
| 5 | (R)-1-((5-(2-oxa-6-azaspiro[3.3]heptan-6-yl)pyridin-2-yl)methyl)-3-(3-(3,4-dihydroisoquinolin-2(1H)-yl)-2-hydroxypropyl)imidazolidin-2-one; |
| 6 | (R)-1-((5-(4-(cyclopropanecarbonyl)piperazin-1-yl)pyridin-2-yl)methyl)-3-(3-(3,4-dihydroisoquinolin-2(1H)-yl)-2-hydroxypropyl)imidazolidin-2-one; |
| 7 | (R)-1-((5-(4-acetylpiperidin-1-yl)pyrazin-2-yl)methyl)-3-(3-(3,4-dihydroisoquinolin-2(1H)-yl)-2-hydroxypropyl)imidazolidin-2-one; |
| 8 | (R)-1-((5-(4-(cyclopropanecarbonyl)piperazin-1-yl)pyrazin-2-yl)methyl)-3-(3-(3,4-dihydroisoquinolin-2(1H)-yl)-2-hydroxypropyl)imidazolidin-2-one; |
| 9 | (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carbonitrile; |
| 10 | (R)-1-(5-((3-(3-(3,4-dihydroisoquinolin-2(1H)-yl)-2-hydroxypropyl)-2-oxoimidazolidin-1-yl)methyl)pyrazin-2-yl)piperidine-4-carbonitrile; |
| 11 | (R)-1-((5-(4-acetylpiperidin-1-yl)pyridin-2-yl)methyl)-3-(3-(3,4-dihydroisoquinolin-2(1H)-yl)-2-hydroxypropyl)imidazolidin-2-one; |
| 12 | (R)-1-((5-(2-oxa-7-azaspiro[3.5]nonan-7-yl)pyridin-2-yl)methyl)-3-(3-(3,4-dihydroisoquinolin-2(1H)-yl)-2-hydroxypropyl)imidazolidin-2-one; |
| 13 | ethyl(R)-2-(1-(6-((3-(3-(3,4-dihydroisoquinolin-2(1H)-yl)-2-hydroxypropyl)-2-oxoimidazolidin-1-yl)methyl)pyridin-3-yl)piperidin-4-yl)-2-methylpropanoate; |
| 14 | (R)-2-(1-(6-((3-(3-(3,4-dihydroisoquinolin-2(1H)-yl)-2-hydroxypropyl)-2-oxoimidazolidin-1-yl)methyl)pyridin-3-yl)piperidin-4-yl)-2-methylpropanoic acid; |
| 15 | (R)-1-(6-((3-(3-(3,4-dihydroisoquinolin-2(1H)-yl)-2-hydroxypropyl)-2-oxoimidazolidin-1-yl)methyl)pyridin-3-yl)-N,N-dimethylpiperidine-4-sulfonamide; |
| 16 | (R)-1-(5-((3-(3-(3,4-dihydroisoquinolin-2(1H)-yl)-2-hydroxypropyl)-2-oxoimidazolidin-1-yl)methyl)pyridin-2-yl)-N,N-dimethylpiperidine-4-sulfonamide; |
| 17 | (R)-1-(3-(3,4-dihydroisoquinolin-2(1H)-yl)-2-hydroxypropyl)-3-((6-(4-(pyrrolidine-1-carbonyl)piperidin-1-yl)pyridin-3-yl)methyl)imidazolidin-2-one; |
| 18 | 1-((5-(3-oxa-8-azabicyclo[3.2.1]octan-8-yl)pyridin-2-yl)methyl)-3-((R)-3-(3,4-dihydroisoquinolin-2(1H)-yl)-2-hydroxypropyl)imidazolidin-2-one; |
| 19 | 1-((5-(3-oxa-8-azabicyclo[3.2.1]octan-8-yl)pyridin-2-yl)methyl)-3-3-(3,4-dihydroisoquinolin-2(1H)-yl)-2-hydroxypropyl)imidazolidin-2-one; |
| 20 | 1-((5-((3R,5S)-4-acetyl-3,5-dimethylpiperazin-1-yl)pyridin-2-yl)methyl)-3-((R)-3-(3,4-dihydroisoquinolin-2(1H)-yl)-2-hydroxypropyl)imidazolidin-2-one; |
| 21 | 1-((5-(4-acetyl-2-methylpiperazin-1-yl)pyridin-2-yl)methyl)-3-((R)-3-(3,4-dihydroisoquinolin-2(1H)-yl)-2-hydroxypropyl)imidazolidin-2-one; |
| 22 | 1-((5-(8-oxa-3-azabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |
| 23 | 1-((6-(8-oxa-3-azabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 24 | 1-((5-(3-oxa-8-azabicyclo[3.2.1]octan-8-yl)pyrazin-2-yl)methyl)-3-((R)-3-(3,4-dihydroisoquinolin-2(1H)-yl)-2-hydroxypropyl)imidazolidin-2-one; |
| 25 | 1-((6-(3,3-difluoro-8-azabicyclo[3.2.1]octan-8-yl)pyridin-3-yl)methyl)-3-((R)-3-(3,4-dihydroisoquinolin-2(1H)-yl)-2-hydroxypropyl)imidazolidin-2-one; |
| 26 | 1-(4-(3-oxa-8-azabicyclo[3.2.1]octan-8-yl)benzyl)-3-((R)-3-(3,4-dihydroisoquinolin-2(1H)-yl)-2-hydroxypropyl)imidazolidin-2-one; |
| 27 | 1-((6-(3-oxa-6-azabicyclo[3.1.1]heptan-6-yl)pyridin-3-yl)methyl)-3-((R)-3-(3,4-dihydroisoquinolin-2(1H)-yl)-2-hydroxypropyl)imidazolidin-2-one; |
| 28 | 1-(4-(3-oxa-8-azabicyclo[3.2.1]octan-8-yl)-3-fluorobenzyl)-3-((R)-3-(3,4-dihydroisoquinolin-2(1H)-yl)-2-hydroxypropyl)imidazolidin-2-one; |
| 29 | 1-((5-(3-oxa-6-azabicyclo[3.1.1]heptan-6-yl)pyridin-2-yl)methyl)-3-((R)-3-(3,4-dihydroisoquinolin-2(1H)-yl)-2-hydroxypropyl)imidazolidin-2-one; |

-continued

| Comp. No | IUPAC Name |
|---|---|
| 30 | 1-((5-(3-oxa-8-azabicyclo[3.2.1]octan-8-yl)-3-fluoropyridin-2-yl)methyl)-3-((R)-3-(3,4-dihydroisoquinolin-2(1H)-yl)-2-hydroxypropyl)imidazolidin-2-one; |
| 31 | 1-(4-(3-oxa-8-azabicyclo[3.2.1]octan-8-yl)-2-fluorobenzyl)-3-((R)-3-(3,4-dihydroisoquinolin-2(1H)-yl)-2-hydroxypropyl)imidazolidin-2-one; |
| 32 | (R)-1-((6-(1-acetylpiperidin-4-yl)pyridin-3-yl)methyl)-3-(3-(3,4-dihydroisoquinolin-2(1H)-yl)-2-hydroxypropyl)imidazolidin-2-one; |
| 33 | (R)-1-((5-(1-acetylpiperidin-4-yl)pyridin-2-yl)methyl)-3-(3-(3,4-dihydroisoquinolin-2(1H)-yl)-2-hydroxypropyl)imidazolidin-2-one; |
| 34 | (R)-1-((5-(1-acetylpiperidin-4-yl)pyrazin-2-yl)methyl)-3-(3-(3,4-dihydroisoquinolin-2(1H)-yl)-2-hydroxypropyl)imidazolidin-2-one; |
| 35 | (R)-1-(3-(3,4-dihydroisoquinolin-2(1H)-yl)-2-hydroxypropyl)-3-((5-(tetrahydro-2H-pyran-4-yl)pyridin-2-yl)methyl)imidazolidin-2-one; |
| 36 | (R)-1-((5-(1-(cyclopropanecarbonyl)piperidin-4-yl)pyridin-2-yl)methyl)-3-(3-(3,4-dihydroisoquinolin-2(1H)-yl)-2-hydroxypropyl)imidazolidin-2-one; |
| 37 | (R)-1-(3-(3,4-dihydroisoquinolin-2(1H)-yl)-2-hydroxypropyl)-3-((5-(pyridin-3-yl)pyrazin-2-yl)methyl)imidazolidin-2-one; |
| 38 | (R)-1-((6-(1-acetylpiperidin-4-yl)pyridazin-3-yl)methyl)-3-(3-(3,4-dihydroisoquinolin-2(1H)-yl)-2-hydroxypropyl)imidazolidin-2-one; |
| 39 | 1-((5-(1-acetylpiperidin-4-yl)pyridin-2-yl)methyl)-3-(3-(3,4-dihydroisoquinolin-2(1H)-yl)-2-hydroxypropyl)-4,4-dimethylimidazolidin-2-one; |
| 40 | (R)-1-(3-(3,4-dihydroisoquinolin-2(1H)-yl)-2-hydroxypropyl)-3-((5-(tetrahydro-2H-pyran-4-yl)pyrazin-2-yl)methyl)imidazolidin-2-one; |
| 41 | (R)-1-((5-(1-(cyclopropanecarbonyl)piperidin-4-yl)pyrazin-2-yl)methyl)-3-(3-(3,4-dihydroisoquinolin-2(1H)-yl)-2-hydroxypropyl)imidazolidin-2-one; |
| 42 | (R)-1-(3-(3,4-dihydroisoquinolin-2(1H)-yl)-2-hydroxypropyl)-3-((5-(pyrimidin-5-yl)pyridin-2-yl)methyl)imidazolidin-2-one; |
| 43 | (R)-1-(3-(3,4-dihydroisoquinolin-2(1H)-yl)-2-hydroxypropyl)-3-((5-(1-(methylsulfonyl)piperidin-4-yl)pyridin-2-yl)methyl)imidazolidin-2-one; |
| 44 | (R)-1-(3-(3,4-dihydroisoquinolin-2(1H)-yl)-2-hydroxypropyl)-3-((5-(1-propionylpiperidin-4-yl)pyridin-2-yl)methyl)imidazolidin-2-one; |
| 45 | (S)-1-((5-(1-acetylpiperidin-4-yl)pyridin-2-yl)methyl)-3-(3-(3,4-dihydroisoquinolin-2(1H)-yl)-2-hydroxypropyl)imidazolidin-2-one; |
| 46 | 1-((5-(1-acetylpiperidin-3-yl)pyridin-2-yl)methyl)-3-((R)-3-(3,4-dihydroisoquinolin-2(1H)-yl)-2-hydroxypropyl)imidazolidin-2-one; |
| 47 | (R)-1-(3-(3,4-dihydroisoquinolin-2(1H)-yl)-2-hydroxypropyl)-3-((5-(1-methylpiperidin-4-yl)pyridin-2-yl)methyl)imidazolidin-2-one; |
| 48 | (R)-1-((1'-acetyl-1',2',3',6'-tetrahydro-[3,4'-bipyridin]-6-yl)methyl)-3-(3-(3,4-dihydroisoquinolin-2(1H)-yl)-2-hydroxypropyl)imidazolidin-2-one; |
| 49 | (R)-1-((5-(3,6-dihydro-2H-pyran-4-yl)pyridin-2-yl)methyl)-3-(3-(3,4-dihydroisoquinolin-2(1H)-yl)-2-hydroxypropyl)imidazolidin-2-one; |
| 50 | (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carbonitrile; |
| 51 | (R)-1-(3-(3,4-dihydroisoquinolin-2(1H)-yl)-2-hydroxypropyl)-3-((6-(tetrahydro-2H-pyran-4-yl)pyridazin-3-yl)methyl)imidazolidin-2-one; |
| 52 | (R)-6'-((3-(3-(3,4-dihydroisoquinolin-2(1H)-yl)-2-hydroxypropyl)-2-oxoimidazolidin-1-yl)methyl)-1-methyl-[3,3'-bipyridin]-6(1H)-one; |
| 53 | (R)-1-(3-(3,4-dihydroisoquinolin-2(1H)-yl)-2-hydroxypropyl)-3-((5-(1-(3-methyloxetane-3-carbonyl)piperidin-4-yl)pyridin-2-yl)methyl)imidazolidin-2-one; |
| 54 | (R)-5-(2-((3-(3-(3,4-dihydroisoquinolin-2(1H)-yl)-2-hydroxypropyl)-2-oxoimidazolidin-1-yl)methyl)pyridin-4-yl)pyrimidine-2-carbonitrile; |
| 55 | (R)-5-(6-((3-(3-(3,4-dihydroisoquinolin-2(1H)-yl)-2-hydroxypropyl)-2-oxoimidazolidin-1-yl)methyl)pyridin-2-yl)pyrimidine-2-carbonitrile; |
| 56 | (R)-1-(3-(3,4-dihydroisoquinolin-2(1H)-yl)-2-hydroxypropyl)-3-((2'-hydroxy-[3,4'-bipyridin]-6-yl)methyl)imidazolidin-2-one; |
| 57 | (R)-1-((6-(1-(cyclopropanecarbonyl)piperidin-4-yl)pyridin-3-yl)methyl)-3-(3-(3,4-dihydroisoquinolin-2(1H)-yl)-2-hydroxypropyl)imidazolidin-2-one; |
| 58 | (R)-1-(3-(3,4-dihydroisoquinolin-2(1H)-yl)-2-hydroxypropyl)-3-((2'-methoxy-[2,4'-bipyridin]-5-yl)methyl)imidazolidin-2-one; |
| 59 | (R)-1-(3-(3,4-dihydroisoquinolin-2(1H)-yl)-2-hydroxypropyl)-3-((2'-methoxy-[2,4'-bipyridin]-5-yl)methyl)imidazolidin-2-one; |
| 60 | (R)-1-(3-(3,4-dihydroisoquinolin-2(1H)-yl)-2-hydroxypropyl)-3-((6'-methoxy-[2,3'-bipyridin]-5-yl)methyl)imidazolidin-2-one; |
| 61 | (R)-6'-((3-(3-(3,4-dihydroisoquinolin-2(1H)-yl)-2-hydroxypropyl)-2-oxoimidazolidin-1-yl)methyl)-[3,3'-bipyridin]-6(1H)-one; |
| 62 | (R)-1-(3-(3,4-dihydroisoquinolin-2(1H)-yl)-2-hydroxypropyl)-3-((6'-methoxy-[3,3'-bipyridin]-6-yl)methyl)imidazolidin-2-one; |
| 63 | (R)-5-((3-(3-(3,4-dihydroisoquinolin-2(1H)-yl)-2-hydroxypropyl)-2-oxoimidazolidin-1-yl)methyl)-[2,3'-bipyridin]-6'(1'H)-one; |
| 64 | (R)-1-(3-(3,4-dihydroisoquinolin-2(1H)-yl)-2-hydroxypropyl)-3-((2'-isopropoxy-[3,4'-bipyridin]-6-yl)methyl)imidazolidin-2-one; |
| 65 | (R)-6-((3-(3-(3,4-dihydroisoquinolin-2(1H)-yl)-2-hydroxypropyl)-2-oxoimidazolidin-1-yl)methyl)-1'-methyl-[3,4'-bipyridin]-2'(1'H)-one; |
| 66 | 1-((5-(8-oxabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |

-continued

| Comp. No | IUPAC Name |
|---|---|
| 67 | (R)-1-(3-(3,4-dihydroisoquinolin-2(1H)-yl)-2-hydroxypropyl)-3-((2'-isopropoxy-[2,4'-bipyridin]-5-yl)methyl)imidazolidin-2-one; |
| 68 | 1-((R)-3-(3,4-dihydroisoquinolin-2(1H)-yl)-2-hydroxypropyl)-3-((5-(3-methyltetrahydro-2H-pyran-4-yl)pyridin-2-yl)methyl)imidazolidin-2-one; |
| 69 | (R)-5-((3-(3-(3,4-dihydroisoquinolin-2(1H)-yl)-2-hydroxypropyl)-2-oxoimidazolidin-1-yl)methyl)-1'-methyl-[2,4'-bipyridin]-2'(1'H)-one; |
| 70 | 1-((R)-3-(3,4-dihydroisoquinolin-2(1H)-yl)-2-hydroxypropyl)-3-((6-(3-methyltetrahydro-2H-pyran-4-yl)pyridin-3-yl)methyl)imidazolidin-2-one; |
| 71 | 1-((R)-3-(3,4-dihydroisoquinolin-2(1H)-yl)-2-hydroxypropyl)-3-((6-(3-methyltetrahydro-2H-pyran-4-yl)pyridin-3-yl)methyl)imidazolidin-2-one; |
| 72 | 1-((5-(8-acetyl-8-azabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |
| 73 | 1-((6-(8-acetyl-8-azabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 74 | 1-((6-(8-oxabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 75 | 1-((6-cyclopropylpyridin-3-yl)methyl)-3-(3-(3,4-dihydroisoquinolin-2(1H)-yl)-2-hydroxypropyl)imidazolidin-2-one; |
| 76 | 3-((6-cyclopropylpyridin-3-yl)methyl)-1-(3-(3,4-dihydroisoquinolin-2(1H)-yl)-2-hydroxypropyl)-5,5-dimethylimidazolidine-2,4-dione; |
| 77 | 1-((R)-3-(3,4-dihydroisoquinolin-2(1H)-yl)-2-hydroxypropyl)-3-((5-(tetrahydro-2H-pyran-3-yl)pyridin-2-yl)methyl)imidazolidin-2-one; |
| 78 | (R)-1-(3-(3,4-dihydroisoquinolin-2(1H)-yl)-2-hydroxypropyl)-3-((5-(oxetan-3-yl)pyridin-2-yl)methyl)imidazolidin-2-one; |
| 79 | (R)-1-((5-(1-acetylazetidin-3-yl)pyridin-2-yl)methyl)-3-(3-(3,4-dihydroisoquinolin-2(1H)-yl)-2-hydroxypropyl)imidazolidin-2-one; |
| 80 | 1-((5-(1-acetylpyrrolidin-3-yl)pyridin-2-yl)methyl)-3-((R)-3-(3,4-dihydroisoquinolin-2(1H)-yl)-2-hydroxypropyl)imidazolidin-2-one; |
| 81 | 1-((5-(4-acetylpiperazin-1-yl)pyridin-2-yl)methyl)-3-(3-(8-fluoro-3,4-dihydroisoquinolin-2(1H)-yl)-2-hydroxypropyl)imidazolidin-2-one; |
| 82 | 1-((5-(4-acetylpiperazin-1-yl)pyridin-2-yl)methyl)-3-(3-(6,7-dihydrothieno[3,2-c]pyridin-5(4H)-yl)-2-hydroxypropyl)imidazolidin-2-one; |
| 83 | 1-((5-(4-acetylpiperazin-1-yl)pyridin-2-yl)methyl)-3-(3-(3,4-dihydropyrrolo[1,2-a]pyrazin-2(1H)-yl)-2-hydroxypropyl)imidazolidin-2-one; |
| 84 | 1-((5-(4-acetylpiperazin-1-yl)pyridin-2-yl)methyl)-3-(2-hydroxy-3-(isoindolin-2-yl)propyl)imidazolidin-2-one; |
| 85 | 1-((5-(4-acetylpiperazin-1-yl)pyridin-2-yl)methyl)-3-(3-(6,7-dihydropyrazolo[1,5-a]pyrazin-5(4H)-yl)-2-hydroxypropyl)imidazolidin-2-one; |
| 86 | 1-((5-(3-oxa-8-azabicyclo[3.2.1]octan-8-yl)pyridin-2-yl)methyl)-3-(3-((2,3-dihydro-1H-inden-2-yl)amino)-2-hydroxypropyl)imidazolidin-2-one; |
| 87 | 1-((5-(3-oxa-8-azabicyclo[3.2.1]octan-8-yl)pyridin-2-yl)methyl)-3-(2-hydroxy-3-(quinolin-2-ylamino)propyl)imidazolidin-2-one; |
| 88 | 1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 89 | (R)-1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 90 | (S)-1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 91 | 5-(6-((3-(3-(6,7-dimethoxy-3,4-dihydroisoquinolin-2(1H)-yl)-2-hydroxypropyl)-2-oxoimidazolidin-1-yl)methyl)pyridin-3-yl)pyrimidine-2-carbonitrile; |
| 92 | 5-(6-((3-(3-((2,3-dihydro-1H-inden-2-yl)amino)-2-hydroxypropyl)-2-oxoimidazolidin-1-yl)methyl)pyridin-3-yl)pyrimidine-2-carbonitrile; |
| 93 | 1-(3-((2,3-dihydro-1H-inden-5-yl)amino)-2-hydroxypropyl)-3-((5-(tetrahydro-2H-pyran-4-yl)pyridin-2-yl)methyl)imidazolidin-2-one; |
| 94 | 1-(2-hydroxy-3-(naphthalen-2-ylamino)propyl)-3-((5-(tetrahydro-2H-pyran-4-yl)pyridin-2-yl)methyl)imidazolidin-2-one; |
| 95 | (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic acid; |
| 96 | (R)-1-((5-(4-(azetidine-1-carbonyl)piperidin-1-yl)pyridin-2-yl)methyl)-3-(3-(3,4-dihydroisoquinolin-2(1H)-yl)-2-hydroxypropyl)imidazolidin-2-one; |
| 97 | (R)-1-(6-((3-(3-(3,4-dihydroisoquinolin-2(1H)-yl)-2-hydroxypropyl)-2-oxoimidazolidin-1-yl)methyl)pyridin-3-yl)-N,N-dimethylpiperidine-4-carboxamide; |
| 98 | (R)-1-((5-(1-((1H-1,2,3-triazol-4-yl)methyl)piperidin-4-yl)pyridin-2-yl)methyl)-3-(3-(3,4-dihydroisoquinolin-2(1H)-yl)-2-hydroxypropyl)imidazolidin-2-one; |
| 99 | (R)-1-((5-(1-((2H-tetrazol-5-yl)methyl)piperidin-4-yl)pyridin-2-yl)methyl)-3-(3-(3,4-dihydroisoquinolin-2(1H)-yl)-2-hydroxypropyl)imidazolidin-2-one; |
| 100 | (R)-6'-((3-(3-(3,4-dihydroisoquinolin-2(1H)-yl)-2-hydroxypropyl)-2-oxoimidazolidin-1-yl)methyl)-2-oxo-2H-[1,3'-bipyridine]-4-carbonitrile |
| 101 | (R)-6'-((3-(3-(3,4-dihydroisoquinolin-2(1H)-yl)-2-hydroxypropyl)-2-oxoimidazolidin-1-yl)methyl)-2H-[1,3'-bipyridin]-2-one; |
| 102 | (R)-1-(3-(3,4-dihydroisoquinolin-2(1H)-yl)-2-hydroxypropyl)-3-((5-(2-(pyrrolidine-1-carbonyl)pyrimidin-5-yl)pyridin-2-yl)methyl)imidazolidin-2-one; |

| Comp. No | IUPAC Name |
|---|---|
| 103 | (R)-1-(3-(3,4-dihydroisoquinolin-2(1H)-yl)-2-hydroxypropyl)-3-((6-(2-(pyrrolidine-1-carbonyl)pyrimidin-5-yl)pyridin-3-yl)methyl)imidazolidin-2-one; and |
| 104 | (R)-1-(3-(3,4-dihydroisoquinolin-2(1H)-yl)-2-methoxypropyl)-3-((5-(tetrahydro-2H-pyran-4-yl)pyridin-2-yl)methyl)imidazolidin-2-one; | or a pharmaceutically acceptable salt or a stereoisomer thereof.

Pharmaceutical Compositions

In certain embodiments, present invention provides a pharmaceutical composition comprising a compound of formula (I) or a pharmaceutically acceptable salt or a stereoisomer thereof, and a pharmaceutically acceptable carrier or excipient.

In certain embodiments, the pharmaceutical composition of the invention further comprises at least one agent selected from an anticancer agent, a chemotherapy agent, and an antiproliferative compound.

In certain embodiments, an anticancer agent, a chemotherapy agent, and an antiproliferative compound is selected from 1) an aldosterone synthase inhibitor; 2) an ALK inhibitor; an apoptosis inducer; 3) an aromatase inhibitor; 4) a CART cell (e.g., a CART cell targeting CD19); 5) a BCR-ABL inhibitor; 6) a BRAF inhibitor; 7) a CDK inhibitor; 8) a CEACAM (e.g., CEACAM-1, -3 and/or -5) inhibitor; 9) a c-KIT inhibitor; 10) a c-MET inhibitor; 10) a cRAP inhibitor; 11) a CTLA4 inhibitor; 12) a cytochrome P450 inhibitor (e.g., a CYP17 inhibitor); 13) an EGF inhibitor; 14) an ERK1/2 ATP inhibitor; 15) an FGF inhibitor (e.g., a FGFR2 or FGFR4 inhibitor); 16) a Flt3 inhibitor (e.g., FLK2/STK1); 17) a P-Glycoprotein 1 inhibitor; 18) a HDAC inhibitor; 19) a HDM2 inhibitor; 20) a HER3 inhibitor; 21) a histamine release inhibitor; 22) an HSP90 inhibitor: 23) an IAP inhibitor; 24) an IDH inhibitor; 25) an IDO inhibitor 26) an IGF-1R inhibitor; 27) an iron chelating agent; 28) a Janus inhibitor; 29) a LAG-3 inhibitor; 30) an M-CSF inhibitor; 31) a MEK inhibitor; 32) an mTOR inhibitor; 33) a p53 inhibitor (e.g., an inhibitor of a p53/Mdm2 interaction); 34) a PDGFRβ inhibitor; 35) a PKC inhibitor; 36) a PI3K inhibitor; 37) a PIM inhibitor; 38) a PRLR inhibitor; 39) a Raf kinase C inhibitor; 40) a smoothened (SMO) receptor inhibitor; 41) a somatostatin agonist and/or a growth hormone release inhibitor; 42) a transduction modulator and/or angiogenesis inhibitor; 43) a VEGFR-2 inhibitor (e.g., FLK-1/KDR); 44) a tyrosine kinase inhibitor (e.g., CSF-1R tyrosine kinase); 45) a Wnt signaling inhibitor 46) a Bcl-2 inhibitor; 47) a Mcl-1 inhibitor; 48) a BTK inhibitor; 49) dual active molecules such as CUDC-907 (a dual PI3K/HDAC inhibitor); and 50) BET bromodomain inhibitor.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, water or aqueous solutions such as physiologically buffered saline or other solvents or vehicles such as glycols, glycerol, oils such as olive oil, or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers or finely divided solid carriers or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

In certain embodiments, present invention provides a combination comprising the compound of formula (I) or pharmaceutically acceptable salt or a stereoisomer thereof, and one or more therapeutically active co-agents.

Agents for Combination Therapies

In certain embodiments, a compound of Formula (I) can be conjointly administered with another therapeutic agent, e.g., 1) an aldosterone synthase inhibitor; 2) an ALK inhibitor; an apoptosis inducer; 3) an aromatase inhibitor; 4) a CART cell (e.g., a CART cell targeting CD19); 5) a BCR-ABL inhibitor; 6) a BRAF inhibitor; 7) a CDK inhibitor; 8) a CEACAM (e.g., CEACAM-1, -3 and/or -5) inhibitor; 9) a c-KIT inhibitor; 10) a c-MET inhibitor; 10) a cRAP inhibitor; 11) a CTLA4 inhibitor; 12) a cytochrome P450 inhibitor (e.g., a CYP17 inhibitor); 13) an EGF inhibitor; 14) an ERK1/2 ATP inhibitor; 15) an FGF inhibitor (e.g., a FGFR2 or FGFR4 inhibitor); 16) a Flt3 inhibitor (e.g., FLK2/STK1); 17) a P-Glycoprotein 1 inhibitor; 18) a HDAC inhibitor; 19) a HDM2 inhibitor; 20) a HER3 inhibitor; 21) a histamine release inhibitor; 22) an HSP90 inhibitor: 23) an IAP inhibitor; 24) an IDH inhibitor; 25) an IDO inhibitor 26) an IGF-1R inhibitor; 27) an iron chelating agent; 28) a Janus inhibitor; 29) a LAG-3 inhibitor; 30) an M-CSF inhibitor; 31) a MEK inhibitor; 32) an mTOR inhibitor; 33) a p53 inhibitor (e.g., an inhibitor of a p53/Mdm2 interaction); 34) a PDGFRβ inhibitor; 35) a PKC inhibitor; 36) a PI3K inhibitor; 37) a PIM inhibitor; 38) a PRLR inhibitor; 39) a Raf kinase C inhibitor; 40) a smoothened (SMO) receptor inhibitor; 41) a somatostatin agonist and/or a growth hormone release inhibitor; 42) a transduction modulator and/or angiogenesis inhibitor; 43) a VEGFR-2 inhibitor (e.g., FLK-1/KDR); 44) a tyrosine kinase inhibitor (e.g., CSF-1R tyrosine kinase); 45) a Wnt signaling inhibitor 46) a Bcl-2 inhibitor; 47) a Mcl-1 inhibitor; 48) a BTK inhibitor; 49) dual active molecules such as CUDC-907 (a dual PI3K/HDAC inhibitor); and 50) BET bromodomain inhibitor.

Additional therapeutic agents suitable for conjoint administration with the compounds and compositions disclosed herein have been described, for example, in the following publications: WO2016/100882; WO2016/054555; WO2016/040892; WO2015/097536; WO2015/088847; WO2015/069770; WO2015/026634; WO 2015/009856; EP 1377609 B1; Antonia, et al. Clin. Cancer Res. 2014 20:6258-6268; and Melero, et al. Nature Reviews Cancer 2015 15:457-472. Each publication is incorporated herein by reference in its entirety.

In certain embodiments, the present invention relates to a pharmaceutical composition comprising at least one compound of formula (I) or a pharmaceutically acceptable salt or a stereoisomer thereof, and a pharmaceutically acceptable carrier or excipient.

The compounds of the invention can be prepared by a variety of synthetic routes analogously to the methods known in the literature using suitable starting materials. The compounds according to formula (I) can be prepared e.g. analogously or according to the reaction schemes given in the experimental section of this application.

Methods of Treatment

In certain embodiments, the present invention provides compound of formula (I) or a pharmaceutically acceptable salt or a stereoisomer thereof, as described herein, for use as a medicament.

In certain embodiments, the present invention relates to use of a compound of formula (I) or a pharmaceutically acceptable salt or a stereoisomer thereof, in the manufacture of a medicament for inhibiting protein arginine methyltransferase 5 (PRMT5).

In certain embodiments, the invention provides the use of compound of formula (I) or a pharmaceutically acceptable salt or a stereoisomer thereof, as described herein, in the manufacture of medicament for the treatment of diseases or disorders mediated by PRMT5.

In certain embodiments, the invention provides a method of treating cancer or proliferative disorder, comprising administration of a therapeutically effective amount of a compound of formula (I) or a pharmaceutically acceptable salt or a stereoisomer thereof.

In certain embodiments, the present invention provides methods for inhibiting growth of tumour cells and/or metastasis by administering a therapeutically effective amount of a compound of formula (I) or a pharmaceutically acceptable salt or a stereoisomer thereof.

In certain embodiments, the present invention relates to a method for the treatment or prevention of diseases or disorders mediated by PRMT5, comprising administering to a subject in need thereof a therapeutically effective amount of a compound of formula (I) or a pharmaceutically acceptable salt or a stereoisomer thereof.

In certain embodiments, the present invention provides a method for the treatment or prevention of a cancer, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder, comprising administering to a subject in need thereof a therapeutically effective amount of a compound of formula (I) or a pharmaceutically acceptable salt or a stereoisomer thereof.

In another embodiments, the metabolic disorder is diabetes or obesity.

In certain embodiments, the use of a compound of formula (I) or a pharmaceutically acceptable salt or a stereoisomer thereof in the manufacture of a medicament for the treatment of cancer, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

In certain embodiments, compound of formula (I) or a pharmaceutically acceptable salt or a stereoisomer thereof use in the treatment of a cancer.

In certain embodiments, the invention provides use of compounds of the present invention in the manufacture of a medicament for the treatment and prevention of a proliferative disease. In certain embodiments, the proliferative disease is cancer. In certain embodiments, the proliferative disease is benign neoplasm, a disease associated with angiogenesis, an inflammatory disease, an autoinflammatory disease, or an autoimmune disease. In certain embodiments, the cancer is a lymphoma. In certain embodiments, the cancer is leukemia. In certain embodiments, the cancer is Hodgkin's lymphoma. In certain embodiments, the cancer is non-Hodgkin's lymphoma. In certain embodiments, the cancer is Burkitt's lymphoma. In certain embodiments, the cancer is diffuse large B-cell lymphoma (DLBCL). In certain embodiments, the cancer is MALT lymphoma. In some embodiments, the cancer is germinal center B-cell-like diffuse large B-cell lymphoma (GCB-DLBCL) or primary mediastinal B-cell lymphoma (PMBL). In some embodiments, the cancer is activated B-cell-like diffuse large B-cell lymphoma (ABC-DLBCL).

In any of the foregoing embodiments, the cancer or a proliferative disorder is selected from the group consisting of a solid tumor, benign or malignant tumor, carcinoma of the brain, kidney, liver, stomach, vagina, ovaries, gastric tumors, breast, bladder colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkin's and Non-Hodgkin's lymphoma, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In certain embodiments, the present invention relates to a method of inhibiting protein arginine methyltransferase 5 (PRMT5), comprising administering to a subject in need thereof a therapeutically effective amount of a compound of formula (I) or a pharmaceutically acceptable salt or a stereoisomer thereof.

In certain embodiments, the present invention relates to a compound of formula (I) or a pharmaceutically acceptable salt or a stereoisomer thereof, for use in the treatment or prevention of diseases or disorders mediated by PRMT5.

In certain embodiments, the diseases or disorders mediated by PRMT5 is cancer, a blood disorder, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease or a cardiovascular disorder.

In certain embodiments, compound of formula (I) or a pharmaceutically acceptable salt or a stereoisomer thereof, use in treating diseases or disorders mediated by PRMT5.

In certain embodiments, the diseases or disorders mediated by PRMT5 is cancer, a metabolic disorder, inflammation, autoimmune disease or hemoglobinopathy.

In certain embodiments, the diseases or disorders mediated by PRMT5 is cancer, a blood disorder, a metabolic disorder, inflammation, autoimmune disease or hemoglobinopathy.

In certain embodiments, the cancer as specified herein, is selected from glioblastoma, melanoma, ovarian cancer, lung cancer, prostate cancer, breast cancer, colon cancer, gastric cancer, esophageal cancer and hepatocellular carcinoma.

In certain embodiments, the cancer is solid tumor, benign or malignant tumor, carcinoma of the brain, kidney, lung, liver, stomach, vagina, ovaries, esophageal, gastric tumors, breast, bladder, colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, rectum adenocarcinoma, colon adenocarcinoma, lung adenocarcinoma keratoacanthoma, epidermoid carcinoma, hepatocellular carcinoma, large cell carcinoma, renal cell carcinoma, oligodendoglioma, ovarian clear cell carcinoma, ovarian serous crystadenocarcinoma, non-small-cell lung carcinoma, lymphomas, Hodgkins and Non-Hodgkins, a mammary carcinoma, follicular carcinoma, papillary carcinoma, seminoma, melanoma; hematopoietic carcinoma, hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In certain embodiments, cancer is medulloblastoma, glioblastoma, melanoma, ovarian cancer, lung cancer, prostate cancer, breast cancer, colon cancer, gastric cancer, esophageal cancer and hepatocellular carcinoma.

In certain embodiments, the present invention relates to use of a compound of formula (I) or a pharmaceutically acceptable salt or a stereoisomer thereof, in the manufacture of a medicament for the treatment or prevention of cancer.

In certain embodiments, the present invention relates to use of a compound of formula (I) or a pharmaceutically acceptable salt or a stereoisomer thereof, in the manufacture of a medicament for the treatment or prevention of diseases or disorders selected from glioblastoma, melanoma, ovarian cancer, lung cancer, prostate cancer, breast cancer, colon cancer, gastric cancer, esophageal cancer and hepatocellular carcinoma.

In certain embodiments, blood disorder is sickle cell anemia or beta-thalessemia.

In certain embodiments, the present invention relates to use of a compound of formula (I) or a pharmaceutically acceptable salt or a stereoisomer thereof, in the manufacture of a medicament for the treatment or prevention of beta-thalassemia.

In certain embodiments, the present invention comprises administering to the subject in need thereof a therapeutically effective amount of a compound of the present invention along with one or more additional chemotherapeutic agents independently selected from antiproliferative agents, anticancer agents, immunosuppressant agents and pain-relieving agents.

Definitions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, an alkyl, an alkenyl, an alkynyl, a carbonyl (such as a carboxyl, an alkoxycarbonyl, a formyl, or an acyl), a thiocarbonyl (such as a thioester, a thioacetate, or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl, a heterocycloalkyl, an aralkyl, or an aromatic or heteroaromatic moiety. It will be understood by those skilled in the art that substituents can themselves be substituted, if appropriate.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "alkenyl" refers to a carbon chain which contains at least one carbon-carbon double bond, and which may be linear or branched or combinations thereof. Examples of "alkenyl" include, but not limited to, vinyl, allyl, isopropenyl, pentenyl, hexenyl, heptenyl, 1-propenyl, 2-butenyl and 2-methyl-2-butenyl. The "alkenyl" group may be optionally substituted.

As used herein, the term "alkynyl" refers to straight or branched carbon chains with one or more triple bonds wherein the number of atoms is in the range $C_2$ to $C_6$. The "alkynyl" group may be optionally substituted.

As used herein, the term "halo" or "halogen" alone or in combination with other term(s) means fluorine, chlorine, bromine or iodine.

As used herein, the term "haloalkyl" means alkyl substituted with one or more halogen atoms, wherein the halo and alkyl groups are as defined above. The term "halo" is used herein interchangeably with the term "halogen" meaning F, Cl, Br or I. Examples of "haloalkyl" include, but are not limited to fluoromethyl, difluoromethyl, chloromethyl, trifluoromethyl and 2,2,2-trifluoroethyl.

As used herein, the term "hydroxy" or "hydroxyl" alone or in combination with other term(s) means —OH.

As used herein, the term "oxo" refers to =O group.

As used herein, the term "alkoxy" refers to the group —O-alkyl, where alkyl groups are as defined above. Exemplary $C_1$-$C_{10}$ alkoxy group include but are not limited to methoxy, ethoxy, n-propoxy, n-butoxy or t-butoxy. An alkoxy group can be optionally substituted with one or more suitable groups.

As used herein, the term "cyano" refers to —CN group.

As used herein, "amino" refers to an —NH$_2$ group.

As used herein the term "cycloalkyl" alone or in combination with other term(s) means $C_3$-$C_{10}$ saturated cyclic hydrocarbon ring. A cycloalkyl may be a single ring, which typically contains from 3 to 7 carbon ring atoms. Examples of single-ring cycloalkyls include but are not limited to cyclopropyl, cyclobutyl, cyclopentyl, cyclohexyl and cycloheptyl. A cycloalkyl may alternatively be polycyclic or contain more than one ring. Examples of polycyclic cycloalkyls include bridged, fused and spirocyclic carbocyclyls.

As used herein, the term "heterocycloalkyl" refers to a non-aromatic, saturated or partially saturated, bridged bicyclic, spirocyclic, monocyclic or polycyclic ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. The term "heterocycloalkyl" also refers to the bridged bicyclic ring system having at least one heteroatom or hetero group selected from O, N, S, S(O), S(O)$_2$, NH or C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl, 3-oxa-8-azabicyclo[3.2.1]octanyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl, oxetane, pyridin-2(1H)-one,3,6-dihydro-2H-pyran,1,2,3,6-tetrahydropyridine,3-oxa-6-azabicyclo[3.1.1]heptane, and piperidinyl. All heterocycloalkyl are optionally substituted by one or more aforesaid groups.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, pyrazolopyrimidyl, furopyridinyl, purinyl, benzothiadiazolyl, benzooxadiazolyl, benzotriazolyl, benzotriadiazolyl, carbazolyl, dibenzothienyl, 3-oxa-8-azabicyclo[3.2.1]octane, 2-oxa-6-azaspiro[3.3] heptane, 2-oxa-7-azaspiro[3.5]nonane, acridinyl and the like. Preferably "heteroaryl" refers to 5- to 6-membered ring selected from the group consisting of furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more groups selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido, and sulfonyl group.

As used herein, the term "heterocyclyl" alone or in combination with other term(s) includes both "heterocycloalkyl" and "heteroaryl" groups which are as defined above.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, fluorenyl, indanyl, biphenylenyl and acenaphthyl. Aryl group can be optionally substituted with one or more substituents selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido, and sulfonyl group The term "acyl" refers to a group R—CO— wherein R is an optionally substituted alkyl group defined above. Examples of 'acyl' groups are, but not limited to, $CH_3CO$—, $CH_3CH_2CO$—, $CH_3CH_2CH_2CO$— or $(CH_3)_2CHCO$—.

The term "monocyclic ring" refers to a saturated, partially saturated or aromatic, one ring system.

The term "bicyclic ring" refers to a saturated, partially saturated or aromatic, two ring system. Bicyclic ring comprises of fused, spiro and bridged rings as well.

The term "fused ring" refers to a ring which is part of a ring system with two rings having at least one bond and two atoms in common.

The term "spiro" refers to a ring system consisting of two rings having only one carbon atom in common.

The term "heteroatom" as used herein designates a sulfur, nitrogen or oxygen atom.

The term "bridged bicyclic" refers to two rings share three or more atoms, separating the two bridgehead atoms by a bridge containing at least one atom.

As used herein, the term 'compound(s)' comprises the compounds disclosed in the present invention.

As used herein, the term "comprise" or "comprising" is generally used in the sense of include, that is to say permitting the presence of one or more features or components As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective amount of at least one compound of formula (I) or a pharmaceutically acceptable salt thereof and a pharmaceutically acceptable carrier.

The pharmaceutical composition(s) usually contain(s) about 1% to 99%, for example, about 5% to 75%, or from about 10% to about 30% by weight of the compound of formula (I) or (II) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" that may be interchangeable with 'patient', refers to an animal, preferably a mammal, and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a diseases or disorder, in particular their use in diseases or disorder associated with cancer. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium or zinc salts.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The present invention also provides methods for formulating the disclosed compounds as for pharmaceutical administration.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The term "stereoisomers" refers to any enantiomers, diastereoisomers or geometrical isomers of the compounds of formula (I), wherever they are chiral or when they bear one or more double bonds. When the compounds of the formula (I) and related formulae are chiral, they can exist in racemic or in optically active form. It should be understood that the invention encompasses all stereochemical isomeric forms, including diastereomeric, enantiomeric and epimeric forms, as well as d-Isomers and l-Isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric Isomers. The present invention includes all cis, trans, syn, anti, entgegen (E) and zusammen (Z) Isomers as well as the appropriate mixtures thereof.

The compounds of the present invention may be used as single drug or as a pharmaceutical composition in which the compound is mixed with various pharmacologically acceptable materials.

Experimental Section

The following abbreviations refer respectively to the definitions herein: DMSO—Dimethylsulfoxide; DIPEA—N,N-Diisopropylethylamine; NaHCO$_3$—Sodium bicarbonate; KF—Potassium fluoride; EtOH—Ethanol; MeOH—Methanol; THF—Tetrahydrofuran; SOCl$_2$—Thionylchloride; NaH—Sodium hydride; IPA—Isopropyl alcohol; SiO$_2$—Silica; TFA—Trifluoro acetic acid; DMAP—4-Dimethylaminopyridine; BINAP—2,2'-bis(diphenylphosphino)-1,1'-binaphthyl; Pd(dppf)Cl$_2$—[1,1'-Bis(diphenylphosphino)ferrocene]palladium(II) dichloride; Pd$_2$(dba)$_3$-Tris(dibenzylideneacetone)dipalladium(O); dppf—1,1'-Bis(diphenylphosphino)ferrocene; NiI$_2$—Nickel(II) IodideMgCl$_2$—Magnesium chloride; DMA—Dimethyl acetamide; CuI—Copper Iodide; HATU—1-[Bis(dimethylamino)methylene]-1H-1,2,3-triazolo[4,5-b]pyridinium 3-oxid hexafluorophosphate; DME—Dimethoxy ethane; K$_3$PO$_4$—Tripotassium phosphate; CDI—1,1'-Carbonyldiimidazole; MeI—Methyl iodide; Na$_2$CO$_3$—Sodium carbonate; TMS-N$_3$—Trimethyl silyl azide; H$_2$O—water; br—Broad; A—Angstrom; ° C.—Degree Celsius; conc—Concentrated; CHCl$_3$—Chloroform; CDCl$_3$/chloroform-d-Deuterated Chloroform; DMSO-d$_6$—Deuterated dimethylsulfoxide; CH$_2$Cl$_2$—DCM—Dichloromethane; DMF—N,N-Dimethylformamide; Et$_2$O—Diethyl ether; g— Gram; h—Hours; $^1$H— Proton; Hz—Hertz; J—Coupling Constant; LC-MS—Liquid Chromatography— Mass Spectroscopy; HPLC—High-performance liquid chromatography; chiral HPLC—chiral high-performance liquid chromatography; M—Molar; MHz—Mega Hertz (frequency); MS—Mass Spectroscopy; mmol—Milli Mole; mL—Milli Litre; min—Minutes; mol—Moles; M+—Molecular ion; m/z—mass to charge ratio; N— Normality; NMR—Nuclear Magnetic Resonance; Et$_3$N/TEA—Triethyl amine; ppm—Parts per million; rt/RT—Room temperature; s—Singlet; d—Doublet, t—Triplet; q—Quartet; m—Multiplet; dd—doublet of doublets; td—triplet of doublets; qd—quartet of doublets; ddd—doublet of doublet of doublets; dt—doublet of triplets; ddt—doublet of doublet of triplets;

p—pentate; TLC—Thin Layer Chromatography; THF—Tetrahydrofuran; %—Percentage; µ—Micron; µL—Micro litre and δ—Delta; anh.—anhydrous; and ±—racemic mixture.

General Modes of Preparation:

Following general guidelines apply to all experimental procedures described here. Until otherwise stated, experiments are performed under positive pressure of nitrogen, temperature described is the external temperature (i.e. oil bath temperature). Reagents and solvents received from vendors are used as such without any further drying or purification. Molarities mentioned here for reagents in solutions are approximate as it was not verified by a prior titration with a standard. All reactions are stirred under magnetic stir bar. Cooling to minus temperature was done by acetone/dry ice or wet ice/salts. Magnesium sulfate and sodium sulfate were used as solvent drying agent after reaction work up and are interchangeable. Removing of solvents under reduced pressure or under vacuum means distilling of solvents in a rotary evaporator.

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

The specifics of the process for preparing compounds of the present invention are detailed in the experimental section.

The present invention shall be illustrated by means of some examples, which are not construed to be viewed as limiting the scope of the invention.

Unless otherwise stated, work-up includes distribution of the reaction mixture between the organic and aqueous phases, separation of layers and drying the organic layer over anhydrous sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase.

Analysis of the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention. Some of the intermediates were taken to next step based on TLC results, without further characterization, unless otherwise specified.

Synthesis of Intermediates

Intermediate-1: Synthesis of (R)-1-(2-((tert-butyldimethylsilyl)oxy)-3-(3,4-dihydroisoquinolin-2(1H)-yl)propyl)imidazolidin-2-one Step-a: Synthesis of (R)-2-(oxiran-2-ylmethyl)-1,2,3,4-tetrahydroisoquinoline To a stirred solution of 1,2,3,4-tetrahydroisoquinoline (100.0 g, 750.0 mmol) in 1500 mL of THF was added KF (218.07 g, 3750.0 mmol) under nitrogen atmosphere and the reaction mixture was allowed to stirred for 30 min at 0° C., to this reaction mixture was added (S)-oxiran-2-ylmethyl 3-nitrobenzenesulfonate in THF (500 mL) (213.86 g, 825.0 mmol) drop wise and stirred at RT for 12 h. After completion of reaction (monitored by TLC, eluent: 5% methanol in chloroform), the reaction mixture was filtered, and the filtrate was concentrated under reduced pressure to get 200 g of (R)-2-(oxiran-2-ylmethyl)-1,2,3,4-tetrahydroisoquinoline as a brown coloured liquid, which was carried forward to next step without further purification. $^1$H NMR (600 MHz, Chloroform-d) δ 7.17-7.08 (m, 3H), 7.07-7.02 (m, 1H), 3.80 (d, J=14.8 Hz, 1H), 3.70 (d, J=14.9 Hz, 1H), 3.21 (dq, J=6.7, 3.3, 3.3, 3.2 Hz, 1H), 3.01-2.86 (m, 4H), 2.86-2.76 (m, 2H), 2.56 (dd, J=5.1, 2.7 Hz, 1H), 2.45 (dd, J=13.3, 6.8 Hz, 1H).

Step-b: Synthesis of (S)-1-((2-aminoethyl)amino)-3-(3,4-dihydroisoquinolin-2(1H)-yl)propan-2-ol To a stirred solution of (R)-2-(oxiran-2-ylmethyl)-1,2,3,4-tetrahydroisoquinoline (200 g, 1058 mmol) in 1000 mL of ethanol, was added ethane-1,2-diamine (190.53 g, 3170 mmol), under nitrogen atmosphere and the reaction mixture was stirred for 12 h at 60° C. temperature. After completion of reaction (monitored by TLC, eluent: 5% methanol in DCM), the reaction mixture concentrated under reduced pressure and the residue was diluted with water and extracted with DCM and the combined organic layers were washed with water, brine solution, dried over anhydrous sodium sulphate and concentrated under reduced pressure to get 250.0 g of (S)-1-((2-aminoethyl)amino)-3-(3,4-dihydroisoquinolin-2(1H)-yl)propan-2-ol, which was carry forward to next step without further purification. LCMS: 250.1 [M+H]$^+$.

Step-c: Synthesis of (R)-1-(3-(3,4-dihydroisoquinolin-2(1H)-yl)-2-hydroxypropyl)imidazolidin-2-one To a stirred solution of (S)-1-((2-aminoethyl)amino)-3-(3,4-dihydroisoquinolin-2(1H)-yl)propan-2-ol (250.0 g, 1002.0 mmol) in 2500 mL of DCM, were added DMAP (24.5 g, 200.5 mmol) and CDI (243.8 g, 1503.0 mmol). The reaction mixture was stirred for 16 h at RT. After completion of reaction (monitored by TLC, eluent: 5% methanol in DCM), the reaction mixture was concentrated under reduced pressure to get (83.0 g, 30.08%) of (R)-1-(3-(3,4-dihydroisoquinolin-2(1H)-yl)-2-hydroxypropyl)imidazolidin-2-one as a pale yellow coloured sticky liquid. LCMS: 276.3 [M+H]$^+$.

Step-d: Synthesis (R)-1-(2-((tert-butyldimethylsilyl)oxy)-3-(3,4-dihydroisoquinolin-2(1H)-yl)propyl)imidazolidin-2-one To a stirred solution of (R)-1-(3-(3,4-dihydroisoquinolin-2(1H)-yl)-2-hydroxypropyl)imidazolidin-2-one (83.0 g, 301.0 mmol) in 2500.0 mL of DCM, were added DIPEA (116.8 g, 904.0 mmol) and tert-butyldimethylsilyl_trifluoromethanesulfonate (87.5 g, 331.0 mmol) at −78° C. The reaction mixture was stirred for 1 h at −78° C. and another 1 h at 0° C. temperature. After completion of reaction (monitored by TLC, eluent: 5% methanol in DCM), the reaction mixture was diluted with DCM and washed with water, brine solution, dried over anhydrous sodium sulphate and concentrated under reduced pressure. The obtained residue was purified by column chromatography (SiO$_2$, 30-100% ethyl acetate in hexane) to get (80.0 g, 68.21%) of (R)-1-(2-((tert-butyldimethylsilyl)oxy)-3-(3,4-dihydroisoquinolin-2(1H)-yl)propyl)imidazolidin-2-one as an off-white solid. $^1$H NMR (300 MHz, DMSO-d$_6$) δ 7.15-6.98 (m, 4H), 6.27 (s, 1H), 4.06-3.94 (m, 1H), 3.67-3.51 (m, 2H), 3.51-3.38 (m, 2H), 3.26-3.02 (m, 4H), 2.85-2.63 (m, 4H), 2.44 (dd, J=5.7, 3.3 Hz, 2H), 0.86 (s, 9H), 0.09-0.03 (m, 6H); LCMS: 390.3 [M+H]$^+$.

Intermediate-2: Synthesis of (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one To a stirred solution of (R)-1-(2-((tert-butyldimethylsilyl)oxy)-3-(3,4-dihydroisoquinolin-2(1H)-yl)propyl)imidazolidin-2-one (Intermediate-1) (5.0 g, 12.833 mmol) in 110.0 mL of THF was added NaH (60%) (0.616 g, 15.4 mmol) at 0° C. and the reaction mixture was allowed to stirred for 30 min at RT. Again the reaction mixture was cooled to 0° C. and added 5-bromo-2-(bromomethyl)pyridine (3.83 g, 1.15.40 mmol) in THF (40.0 ml) drop wise and stirred for 12 h at RT. After completion of reaction (monitored by TLC, eluent: 5% methanol in DCM), the reaction mixture was diluted with water and extracted with ethyl acetate. The combined organics were washed with water, brine solution, dried over anhydrous sodium sulphate and concentrated under reduced pressure. The obtained residue was purified by column chromatography (SiO$_2$, 1-2% MeOH in DCM) to get (4.6 g, 64.05%) of (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one. $^1$H NMR (400 MHz, DMSO-d$_6$) δ 8.63 (dd, J=2.4, 0.7 Hz, 1H), 8.02 (dd, J=8.4, 2.5 Hz, 1H), 7.29-7.22 (m, 1H), 7.13-6.98 (m, 4H), 4.32 (d, J=2.1 Hz, 2H), 4.08-4.00 (m, 1H), 3.65-3.54 (m, 2H), 3.45 (dd, J=8.8, 6.8 Hz, 1H), 3.27 (q, J=8.7, 7.9, 7.9 Hz, 3H), 2.79 (d, J=5.7 Hz, 2H), 3.23-3.13 (m, 2H), 2.71 (t, J=5.3, 5.3 Hz, 2H), 2.46 (t, J=6.0, 6.0 Hz, 1H) 2.35-2.30 (m, 1H), 0.84 (s, 9H), 0.08-0.02 (m, 6H).

Intermediate-3: Synthesis of (R)-1-((6-bromopyridin-3-yl)methyl)-3-(2-((tert-butyldimethylsilyl)oxy)-3-(3,4-dihydroisoquinolin-2(1H)-yl)propyl)imidazolidin-2-one To a stirred solution of (R)-1-(2-((tert-butyldimethylsilyl)oxy)-3-(3,4-dihydroisoquinolin-2(1H)-yl)propyl)imidazolidin-2-one (Intermediate-1) (30.0 g, 76.998 mmol) in 400.0 mL of THF was added NaH (60%) (4.61 g, 115.497 mmol) at 0° C. and the reaction mixture was allowed to stirred for 30 min at RT, again the reaction mixture was cooled to 0° C. and added 2-bromo-5-(bromomethyl)pyridine (22.98 g, 92.397 mmol) in THF (250.0 ml) drop wise and stirred for 12 h at RT. After completion of reaction (monitored by TLC, eluent: 5% methanol in DCM), the reaction mixture was diluted with water and extracted with ethyl acetate. The combined organics were washed with water, brine solution, dried over anhydrous sodium sulphate and concentrated under reduced pressure. The obtained residue was purified by column chromatography (SiO$_2$, 2-3% MeOH in DCM) to get (40.0 g, 93.0%) of (R)-1-((6-bromopyridin-3-yl)methyl)-3-(2-((tert-butyldimethylsilyl)oxy)-3-(3,4-dihydroisoquinolin-2(1H)-yl)propyl)imidazolidin-2-one. $^1$H NMR (300 MHz, DMSO-d$_6$) δ 8.29 (dd, J=2.1, 1.3 Hz, 1H), 7.62 (q, J=1.4, 1.3, 1.3 Hz, 2H), 7.13-7.06 (m, 3H), 7.05-6.97 (m, 1H), 4.26 (s, 2H), 4.03 (t, J=5.5, 5.5 Hz, 1H), 3.59 (d, J=4.2 Hz, 2H), 3.47-3.37 (m, 1H), 3.32-3.12 (m, 5H), 2.86-2.65 (m, 4H), 2.48-2.40 (m, 2H), 0.83 (d, J=1.7 Hz, 9H), 0.06-0.03 (m, 6H).

Intermediate-4: Synthesis of (R)-1-(2-((tert-butyldimethylsilyl)oxy)-3-(3,4-dihydroisoquinolin-2(1H)-yl)propyl)-3-((5-(piperidin-4-yl)pyridin-2-yl)methyl)imidazolidin-2-one Step-a: Synthesis of tert-butyl (R)-6-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[3,4'-bipyridine]-1'(2'H)-carboxylate To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (Intermediate-2) (3.0 g, 5.36 mmol), DME/H$_2$O (4:1) (100 mL), tert-butyl 4-(4,4,5,5-tetramethyl-1,3,2-dioxaborolan-2-yl)-3,6-dihydropyridine-1(2H)-carboxylate (3.3 g, 10.7 mmol), Sodium carbonate (1.98 g, 18.7 mmol) and Pd(dppf)Cl$_2$ (1.02 g, 1.34 mmol) and the reaction mixture was degassed with argon gas for 10 minutes, and the reaction mixture was stirred for 12 h at 70° C. After completion of reaction (monitored by TLC, eluent: 5% methanol in DCM), the reaction mixture was diluted with water and extracted with ethyl acetate and the combined organics were washed with brine solution and dried over anhydrous sodium sulphate and concentrated under reduced pressure. The obtained residue was purified by column chromatography (SiO$_2$, 1% MeOH in DCM) to get (2.8 g, 79.09%) of tert-butyl (R)-6-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[3,4'-bipyridine]-1'(2'H)-carboxylate. LCMS: 662.1 [M+H]$^+$.

Step-b: Synthesis of tert-butyl (R)-4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-1-carboxylate A mixture of tert-butyl (R)-6-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[3,4'-bipyridine]-1'(2'H)-carboxylate (1.5 g, 2.26 mmol) and 10% Pd—C (0.3 g) in 70 mL of ethanol was taken in parr shaker vessel and hydrogenated at 60 psi pressure for 12 h at RT. After completion of reaction (monitored by TLC, eluent: 5% Methanol in DCM), the reaction mixture was filtered through celite bed and filtrate was concentrated under reduced pressure. The obtained residue was purified by column chromatography (SiO$_2$, 2% MeOH in DCM) to get (1.06 g, 70.66%) of tert-butyl (R)-4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-1-carboxylate. LCMS: 664.6 [M+H]$^+$.

Step-c: Synthesis of (R)-1-(2-((tert-butyldimethylsilyl)oxy)-3-(3,4-dihydroisoquinolin-2(1H)-yl)propyl)-3-((5-(piperidin-4-yl)pyridin-2-yl)methyl)imidazolidin-2-one To a stirred solution of tert-butyl (R)-4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-1-carboxylate (1.06 g, 1.596 mmol) in 20.0 mL of DCM, was added TFA (3.0 mL) at 0° C. temperature and stirred for 12 h at RT. After completion of reaction (monitored by TLC, eluent: 10% methanol in DCM), the reaction mixture was concentrated under reduced pressure. The obtained residue was diluted with water and basified with sodium carbonate and extracted with DCM. The combined organics were washed with brine solution, dried over anhydrous sodium sulphate and concentrated under reduced pressure to get 0.875 g of (R)-1-(2-((tert-butyldimethylsilyl)oxy)-3-(3,4-dihydroisoquinolin-2(1H)-yl)propyl)-3-((5-(piperidin-4-yl)pyridin-2-yl)methyl)imidazolidin-2-one. LCMS: 564.5 [M+H]$^+$.

EXAMPLES

The present invention is further exemplified, but not limited, by the following examples that illustrate the preparation of compounds according to the invention.

Example-I: Synthesis of (R)-1-(3-(3,4-dihydroisoquinolin-2(1H)-yl)-2-hydroxypropyl)-3-((5-(4-(pyrrolidine-1-carbonyl)piperidin-1-yl)pyridin-2-yl)methyl)imidazolidin-2-one Compound-1

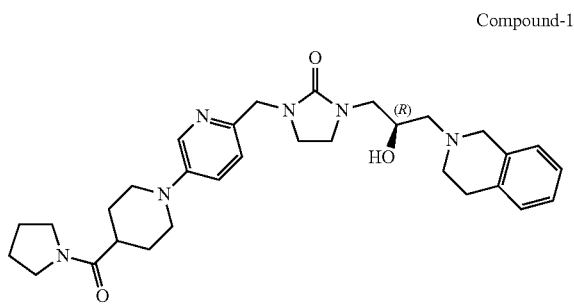

Step-a: Synthesis of (R)-1-(2-((tert-butyldimethylsilyl)oxy)-3-(3,4-dihydroisoquinolin-2(1H)-yl)propyl)-3-((5-(4-(pyrrolidine-1-carbonyl)piperidin-1-yl)pyridin-2-yl)methyl)imidazolidin-2-one To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (Intermediate-2) (15.0 g, 26.8 mmol), 1,4-Di-Oxane (300 mL), the reaction mixture was degassed with argon gas for 10 minutes. To this reaction mixture were added piperidin-4-yl (pyrrolidin-1-yl)methanone (5.58 g, 32.2 mmol), Sodium tert-Butoxide (3.8 g, 40.0 mmol), Pd$_2$(dba)$_3$ (2.45 g, 2.6 mmol) and BINAP (3.29 g, 5.3 mmol) and stirred for 12 h at 100° C. After completion of reaction (monitored by TLC, eluent: 5% Methanol in CHCl$_3$), the reaction mixture was filtered through celite bed and filtrate was concentrated under reduced pressure. The residue was purified with column chromatography (SiO$_2$, 1-2% MeOH in DCM) to get (9.0 g, 50.84%) of (R)-1-(2-((tert-butyldimethylsilyl)oxy)-3-(3,4-dihydroisoquinolin-2(1H)-yl)propyl)-3-((5-(4-(pyrrolidine-1-carbonyl)piperidin-1-yl)pyridin-2-yl)methyl)imidazolidin-2-one. LCMS: 660.5 [M+H]$^+$.

Step-b: Synthesis of (R)-1-(3-(3,4-dihydroisoquinolin-2(1H)-yl)-2-hydroxypropyl)-3-((5-(4-(pyrrolidine-1-carbonyl)piperidin-1-yl)pyridin-2-yl)methyl)imidazolidin-2-one To a stirred solution of (R)-1-(2-((tert-butyldimethylsilyl)oxy)-3-(3,4-dihydroisoquinolin-2(1H)-yl)propyl)-3-((5-(4-(pyrrolidine-1-carbonyl)piperidin-1-yl)pyridin-2-yl)methyl)imidazolidin-2-one (15.0 g, 22.6 mmol) in 200.0 mL of THF was added TBAF (1M solution in THF) (68.0 mL, 68.0 mmol) at 0° C. and the reaction mixture was stirred for 12 h at RT. After completion of reaction (monitored by TLC, eluent: 5% methanol in CHCl$_3$), the reaction mixture was concentrated under reduced pressure and residue was diluted with water and extracted with ethyl acetate. The combined extracts were washed with brine solution and dried over anhydrous sodium sulphate. The obtained residue was purified by column chromatography (SiO$_2$, 6% MeOH in CHCl$_3$) to get (R)-1-(3-(3,4-dihydroisoquinolin-2(1H)-yl)-2-hydroxypropyl)-3-((5-(4-(pyrrolidine-1-carbonyl)piperidin-1-yl)pyridin-2-yl)methyl)imidazolidin-2-one as an off-white solid. $^1$H NMR (400 MHz, Methanol-d$_4$) δ 9.24 (dd, J=2.3, 0.9 Hz, 1H), 9.13 (d, J=1.6 Hz, 1H), 8.71 (d, J=1.5 Hz, 1H), 8.64 (dd, J=5.0, 1.6 Hz, 1H), 8.52 (ddd, J=8.0, 2.3, 1.6 Hz, 1H), 7.59 (ddd, J=8.1, 5.0, 0.9 Hz, 1H), 7.11-7.05 (m, 3H), 7.04-6.99 (m, 1H), 4.58 (s, 2H), 4.08 (tt, J=7.2, 4.6 Hz, 1H), 3.73 (s, 2H), 3.63-3.54 (m, 2H), 3.48 (td, J=7.8, 1.4 Hz, 2H), 3.37 (dd, J=14.2, 4.4 Hz, 1H), 3.21 (dd, J=14.2, 7.1 Hz, 1H), 2.90 (d, J=5.5 Hz, 2H), 2.88-2.81 (m, 2H), 2.65-2.55 (m, 2H), 2.009-1.992 (m, 2H). LCMS: 547.2 [M+H]$^+$.

The compounds listed in below Table-1 were prepared by procedure similar to the one described in Example-1 with appropriate variations in reactants, quantities of reagents, protections and deprotections, solvents and reaction conditions. The characterization data of the compounds are summarized herein the below table.

TABLE 1

| Comp. No | Structure | Characterization Data |
| --- | --- | --- |
| 2 | 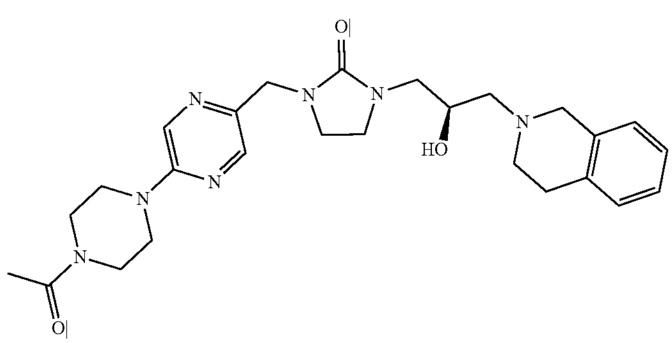 | $^1$H NMR (400 MHz, Methanol-d4) δ 8.18 (d, J = 1.5 Hz, 1H), 8.11-8.07 (m, 1H), 7.13-7.07 (m, 3H), 7.03 (dd, J = 7.6, 2.3 Hz, 1H), 5.36-5.30 (m, 1H), 4.35 (d, J = 1.6 Hz, 2H), 4.07 (tt, J = 7.1, 4.6 Hz, 1H), 3.77 (d, J = 2.7 Hz, 1H), 3.73-3.64 (m, 5H), 3.61 (dd, J = 6.7, 3.7 Hz, 2H), 3.57-3.45 (m, 2H), 3.39-3.32 (m, 1H), 3.18 (dd, J = 14.2, 6.9 Hz, 1H), 2.91 (dq, J = 8.9, 4.7 Hz, 3H), 2.63 (dd, J = 6.1, 3.6 Hz, 1H), 2.21-2.12 (m, 4H), 2.02 (q, J = 6.5 Hz, 2H), 1.59 (t, J = 7.3 Hz, 2H). |

TABLE 1-continued

| Comp. No | Structure | Characterization Data |
|---|---|---|
| 3 | 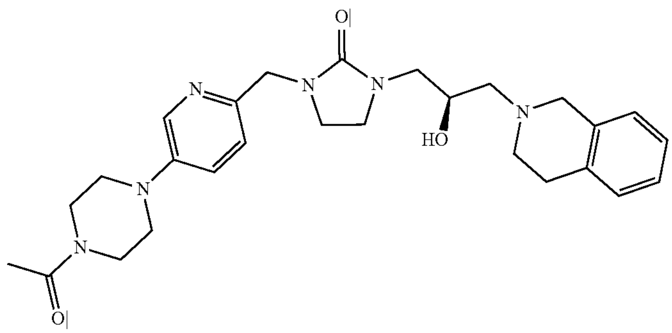 | ¹H NMR (400 MHz, DMSO-d6) δ 8.23 (d, J = 2.9 Hz, 1H), 7.34 (dd, J = 8.6, 3.0 Hz, 1H), 7.14-7.06 (m, 4H), 7.05-7.00 (m, 1H), 4.74 (d, J = 4.8 Hz, 1H), 4.25 (s, 2H), 3.86 (s, 1H), 3.64-3.54 (m, 5H), 3.46-3.39 (m, 1H), 2.91-2.86 (m, 1H), 3.27 (dd, J = 13.9, 4.1 Hz, 1H), 3.20 (t, J = 6.5 Hz, 4H), 3.12 (t, J = 5.3 Hz, 2H), 3.01 (dd, J = 13.9, 7.2 Hz, 1H), 2.80 (t, J = 5.8 Hz, 2H), 2.75-2.65 (m, 3H), 2.43 (d, J = 6.0 Hz, 2H), 2.03 (s, 3H). LCMS: 493.4 [M + H]⁺. |
| 4 | 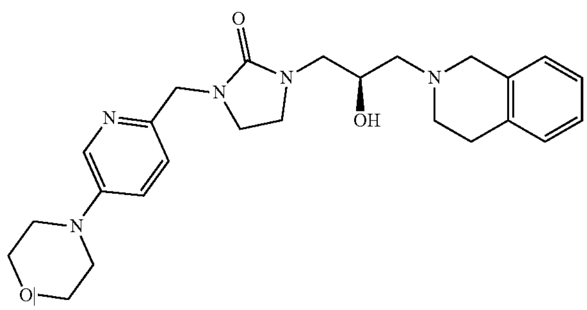 | ¹H NMR (400 MHz, Chloroform-d) δ 8.20 (dd, J = 2.9, 0.7 Hz, 1H), 7.23 (dd, J = 8.6, 0.7 Hz, 1H), 7.20-7.09 (m, 4H), 7.04-6.97 (m, 1H), 4.48-4.38 (m, 2H), 3.99 (dddd, J = 9.4, 6.5, 4.5, 3.2 Hz, 1H), 3.89-3.77 (m, 5H), 3.65-3.42 (m, 4H), 3.31 (t, J = 8.1 Hz, 2H), 3.20-3.12 (m, 5H), 2.96-2.86 (m, 3H), 2.79-2.69 (m, 1H), 2.62-2.49 (m, 2H). LCMS: LCMS: 452 [M + H]⁺. |
| 5 | 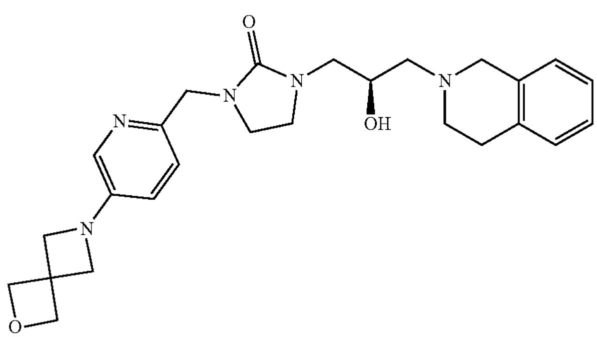 [SMILES: O=C1N(Cc2ccc(N3CC4(COC4)C3)cn2)CCN1C[C@H](O)CN1CCc2ccccc2C1] | ¹H NMR (400 MHz, DMSO-d6) δ 7.74 (dd, J = 2.9, 0.7 Hz, 1H), 7.13-7.00 (m, 5H), 6.84-6.79 (m, 1H), 4.70 (s, 4H), 4.21 (s, 2H), 4.01 (d, J = 0.6 Hz, 4H), 3.86 (s, 1H), 3.60 (s, 2H), 3.40 (dd, J = 9.1, 7.5 Hz, 2H), 3.31-3.21 (m, 2H), 3.16 (t, J = 7.9 Hz, 2H), 3.00 (dd, J = 13.9, 7.2 Hz, 1H), 2.80 (t, J = 5.8 Hz, 2H), 2.71 (s, 2H), 2.43 (d, J = 6.3 Hz, 2H). LCMS: 464.4 [M + H]⁺. |
| 6 | 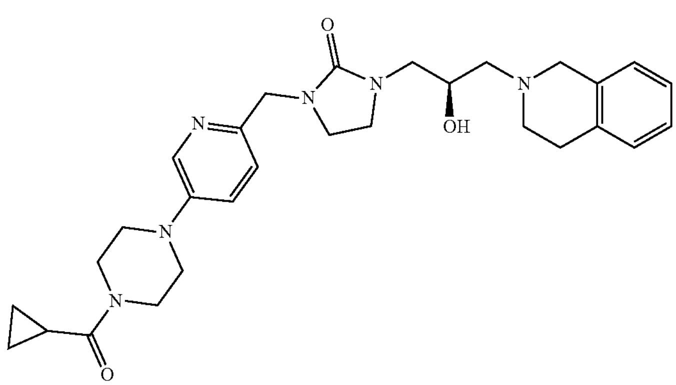 [SMILES: O=C(C1CC1)N1CCN(c2ccc(CN3CCN(C[C@H](O)CN4CCc5ccccc5C4)C3=O)nc2)CC1] | ¹H NMR (400 MHz, DMSO-d6) δ 8.24 (d, J = 2.9 Hz, 1H), 7.35 (dd, J = 8.6, 2.9 Hz, 1H), 7.15-7.06 (m, 4H), 7.02 (dd, J = 6.6, 2.6 Hz, 1H), 4.73 (d, J = 4.8 Hz, 1H), 4.25 (s, 2H), 3.84 (d, J = 15.8 Hz, 3H), 3.60 (s, 4H), 3.45-3.37 (m, 1H), 3.28-3.09 (m, 8H), 3.01 (dd, J = 13.9, 7.2 Hz, 1H), 2.80 (t, J = 5.8 Hz, 2H), 2.75-2.64 (m, 2H), 2.44 (dd, J = 6.1, 3.5 Hz, 2H), 2.03 (tt, J = 7.7, 4.9 Hz, 1H), 0.77-0.68 (m, 4H). LCMS: 519.5 |

TABLE 1-continued

| Comp. No | Structure | Characterization Data |
|---|---|---|
| 7 | 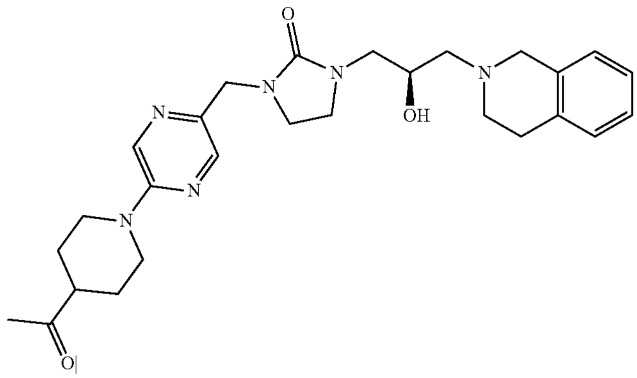 | $^1$H NMR (400 MHz, DMSO-d6) δ 8.26 (s, 1H), 7.98 (s, 1H), 7.09 (d, J = 4.2 Hz, 3H), 7.02 (d, J = 6.0 Hz, 1H), 4.73 (s, 1H), 4.33-4.20 (m, 3H), 3.86 (s, 1H), 3.60 (s, 2H), 2.05-1.94 (m, 3H), 3.28-3.16 (m, 3H), 3.07-2.87 (m, 3H), 2.78 (d, J = 6.1 Hz, 2H), 2.68 (s, 4H), 2.42 (s, 1H), 2.13 (s, 3H), 1.88 (d, J = 13.2 Hz, 2H), 1.40 (d, J = 11.5 Hz, 2H). LCMS: 493.5 [M + H]$^+$. |
| 8 | 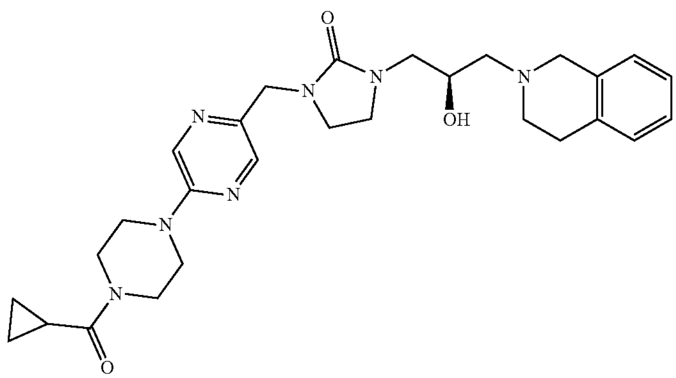 | $^1$H NMR (400 MHz, DMSO-d6) δ 8.30 (d, J = 1.5 Hz, 1H), 8.05 (d, J = 1.6 Hz, 1H), 7.39-7.02 (m, 4H), 4.57 (t, J = 12.9, 12.9 Hz, 1H), 4.37 (dt, J = 22.7, 10.1, 10.1 Hz, 2H), 4.30-4.19 (m, 3H), 3.80 (s, 5H), 3.56 (s, 3H), 3.41 (t, J = 7.6, 7.6 Hz, 2H), 3.30-3.21 (m, 3H), 3.18 (d, J = 5.6 Hz, 2H), 3.02 (t, J = 16.6, 16.6 Hz, 1H), 2.72-2.63 (m, 2H), 2.42-2.26 (m, 1H), 2.11-1.87 (m, 2H), 0.74 (tt, J = 7.9, 7.9, 2.8, 2.8 Hz, 4H). LCMS: 520.5 [M + H]$^+$. |
| 9 | 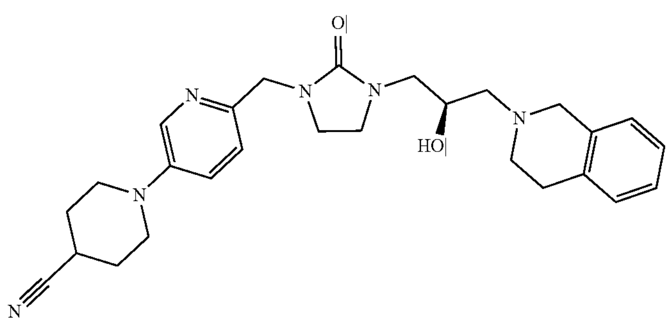 | $^1$H NMR (400 MHz, DMSO-d6) δ 8.21 (d, J = 2.9 Hz, 1H), 7.32 (dd, J = 8.6, 3.0 Hz, 1H), 7.08 (qd, J = 3.8, 1.5 Hz, 4H), 7.03-6.97 (m, J = 3.4 Hz, 1H), 4.72 (d, J = 4.7 Hz, 1H), 4.22 (s, 2H), 3.85 (h, J = 6.0 Hz, 1H), 3.62-3.56 (m, 2H), 3.44-3.35 (m, 3H), 3.28-3.15 (m, 4H), 3.09-2.95 (m, 4H), 2.78 (t, J = 5.8 Hz, 2H), 2.73-2.64 (m, 2H), 2.42 (dd, J = 6.1, 3.5 Hz, 2H), 1.96 (ddt, J = 13.7, 7.1, 3.7 Hz, 2H), 1.79 (dtd, J = 12.4, 8.5, 3.5 Hz, 2H); LCMS: LCMS: 475.4 [M + H]$^+$. |
| 10 | 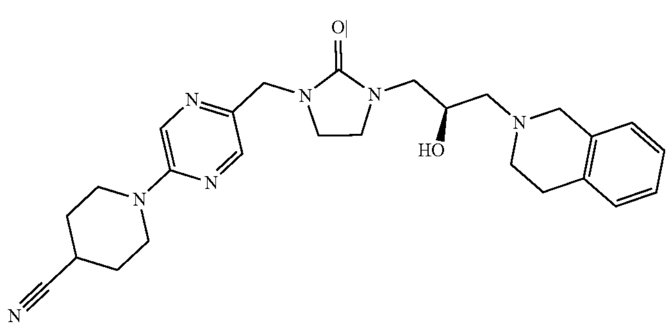 | $^1$H NMR (400 MHz, DMSO-d6) δ 8.29 (d, J = 1.6 Hz, 1H), 8.01 (d, J = 1.5 Hz, 1H), 7.12-7.06 (m, 3H), 7.05-7.00 (m, 1H), 4.72 (d, J = 4.8 Hz, 1H), 4.23 (s, 2H), 3.85 (ddd, J = 13.6, 6.3, 3.7 Hz, 3H), 3.60 (s, 2H), 3.40 (td, J = 9.0, 4.5 Hz, 3H), 3.29-3.19 (m, 4H), 3.13 (tt, J = 8.4, 3.9 Hz, 1H), 3.00 (dd, J = 13.7, 7.2 Hz, 1H), 2.79 (d, J = 5.8 Hz, 2H), 2.70 (dd, J = 5.9, 3.7 Hz, 2H), 2.43 (dd, J = 6.1, 2.5 Hz, 2H), 1.93 (ddt, J = 13.6, 7.3, 3.6 Hz, 2H), 1.79-1.63 (m, 2H); LCMS: LCMS: 476.4 [M + H]$^+$. |

TABLE 1-continued

| Comp. No | Structure | Characterization Data |
|---|---|---|
| 11 | 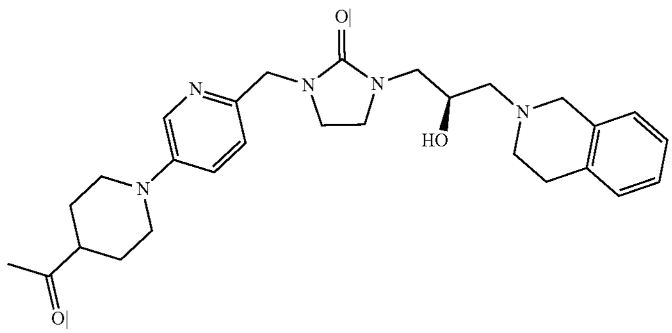 | ¹H NMR (400 MHz, Methanol-d4) δ 8.17 (d, J = 2.9 Hz, 1H), 7.41 (dd, J = 8.7, 3.0 Hz, 1H), 7.25 (d, J = 8.7 Hz, 1H), 7.16-7.10 (m, 3H), 7.06 (dd, J = 7.8, 2.2 Hz, 1H), 4.38 (s, 2H), 4.11 (tt, J = 7.1, 4.5 Hz, 1H), 3.85-3.72 (m, 4H), 3.60-3.49 (m, 2H), 3.41-3.34 (m, 1H), 3.22 (dd, J = 14.2, 6.9 Hz, 1H), 2.96 (s, 4H), 2.84 (td, J = 12.2, 2.7 Hz, 2H), 2.73-2.55 (m, 3H), 2.21 (s, 3H), 2.09-1.96 (m, 2H), 1.77-1.60 (m, 4H); LCMS: 492.4 [M + H]⁺. |
| 12 | 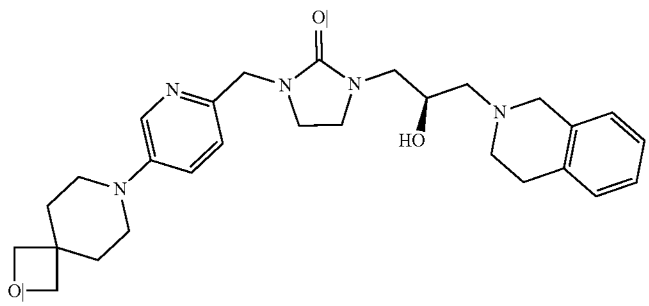 | ¹H NMR (400 MHz, DMSO-d6) δ 8.21 (d, J = 2.9 Hz, 1H), 7.34-7.28 (m, 1H), 7.08 (tt, J = 8.6, 4.2 Hz, 4H), 7.04-7.00 (m, 1H), 4.72 (d, J = 4.8 Hz, 1H), 4.33 (s, 4H), 4.22 (s, 2H), 3.86 (s, 1H), 3.60 (s, 2H), 3.46-3.39 (m, 1H), 3.18 (t, J = 7.9 Hz, 2H), 3.13-3.08 (m, 3H), 3.05-2.96 (m, 4H), 2.79 (t, J = 5.9 Hz, 2H), 2.71 (t, J = 5.2 Hz, 2H), 2.45-2.39 (m, 2H), 1.91-1.81 (m, 4H); LCMS: 492.5 [M + H]⁺. |
| 13 | 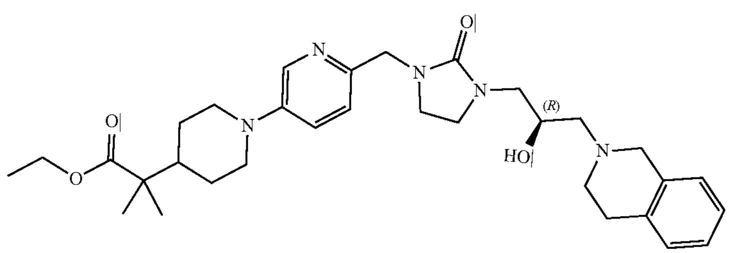 | ¹H NMR (400 MHz, DMSO-d6) δ 8.22 (d, J = 2.9 Hz, 1H), 7.42-7.36 (m, 1H), 7.31-7.23 (m, 3H), 7.18 (dd, J = 19.1, 7.7 Hz, 2H), 5.84 (s, 1H), 4.55 (d, J = 11.7 Hz, 1H), 4.40 (s, 2H), 4.28 (d, J = 1.8 Hz, 2H), 4.23 (d, J = 12.9 Hz, 1H), 4.07 (q, J = 7.1, 7.1, 7.1 Hz, 3H), 3.81 (d, J = 12.6 Hz, 3H), 3.43 (t, J = 7.8, 7.8 Hz, 1H), 3.33-3.16 (m, 6H), 3.13-2.98 (m, 2H), 2.70-2.59 (m, 2H), 1.72-1.56 (m, 3H), 1.35 (td, J = 12.5, 12.5, 3.9 Hz, 2H), 1.17 (t, J = 7.1, 7.1 Hz, 3H), 1.08 (s, 6H). LCMS: 564.5 [M + H]⁺. |
| 14 | 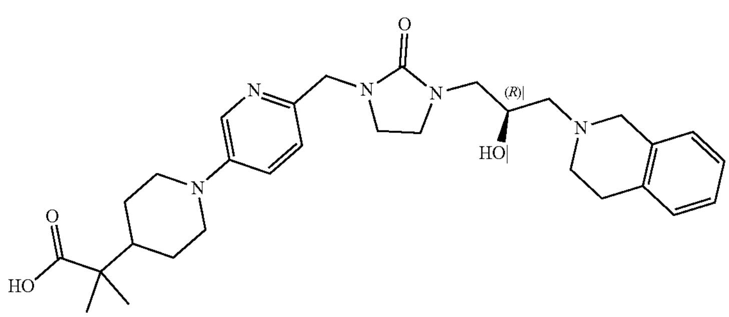 | ¹H NMR (400 MHz, DMSO-d6) δ 8.19 (d, J = 2.9 Hz, 1H), 7.29 (dd, J = 8.7, 3.0 Hz, 1H), 7.12-7.05 (m, 4H), 7.04-7.00 (m, 1H), 4.73 (s, 1H), 4.22 (s, 2H), 3.86 (p, J = 5.9 Hz, 1H), 3.78 (d, J = 12.2 Hz, 2H), 3.60 (s, 2H), 3.47-3.38 (m, 1H), 3.27 (dd, J = 13.8, 4.0 Hz, 1H), 2.35-2.31 (m, 1H), 3.19 (t, J = 8.0 Hz, 2H), 3.00 (dd, J = 13.9, 7.2 Hz, 1H), 2.79 (t, J = 6.1 Hz, 2H), 2.75-2.66 (m, 2H), 2.64-2.54 (m, 2H), 2.46-2.39 (m, 3H), 1.63 (td, J = 13.8, 12.0, 7.5 Hz, 3H), 1.44-1.28 (m, 2H), 1.04 (s, 6H); LCMS: 536.5 [M + H]⁺. |
| 15 | 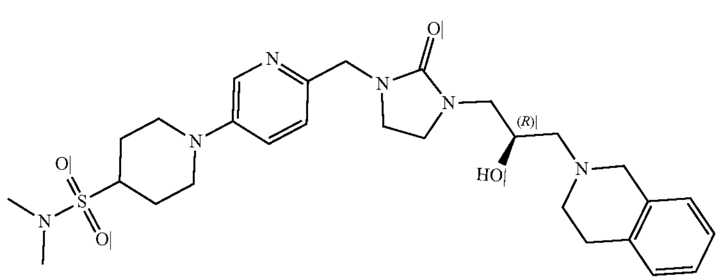 | ¹H NMR (400 MHz, DMSO-d6) δ 8.22 (d, J = 2.9 Hz, 1H), 7.33 (dd, J = 8.7, 3.0 Hz, 1H), 7.12-7.06 (m, 4H), 7.05-7.00 (m, 1H), 4.73 (d, J = 4.7 Hz, 1H), 4.24 (s, 2H), 3.83 (d, J = 13.2 Hz, 2H), 3.60 (s, 2H), 3.52-3.37 (m, 3H), 3.31-3.17 (m, 3H), 3.01 (dd, J = 13.9, 7.2 Hz, 1H), 2.85 (s, 6H), 2.82-2.76 (m, 5H), 2.76-2.64 (m, 3H), 2.44 (s, 2H), 1.97 (d, J = 11.9 Hz, 2H), 1.70 (qd, J = 12.4, 4.1 Hz, 2H); LCMS: 557.4 [M + H]⁺. |

TABLE 1-continued

| Comp. No | Structure | Characterization Data |
|---|---|---|
| 16 | 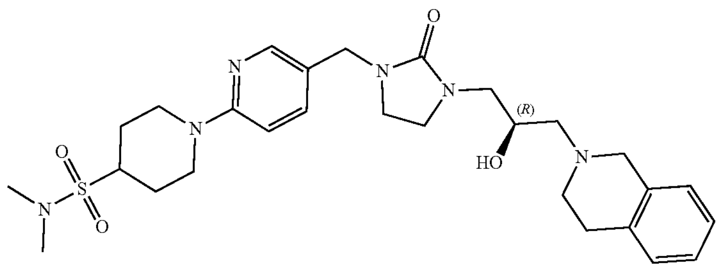 | ¹H NMR (400 MHz, DMSO-d6) δ 7.99 (d, J = 2.4 Hz, 1H), 7.40 (dd, J = 8.7, 2.5 Hz, 1H), 7.13-7.05 (m, 3H), 7.04-6.99 (m, 1H), 6.84 (d, J = 8.7 Hz, 1H), 4.73 (d, J = 4.8 Hz, 1H), 4.37 (d, J = 13.4 Hz, 2H), 4.12 (s, 2H), 3.85 (d, J = 6.6 Hz, 1H), 3.59 (s, 2H), 3.55-3.46 (m, 1H), 3.32-3.22 (m, 3H), 3.09 (t, J = 7.9 Hz, 3H), 2.99 (dd, J = 13.9, 7.1 Hz, 2H), 2.83 (s, 8H), 2.73-2.64 (m, 2H), 2.42 (dd, J = 6.1, 2.9 Hz, 2H), 1.93 (d, J = 11.9 Hz, 2H), 1.54 (qd, J = 12.4, 4.1 Hz, 2H); LCMS: 557.4 [M + H]⁺. |
| 17 | 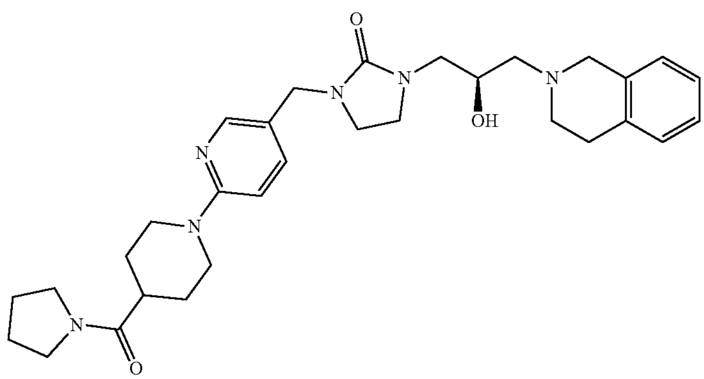 [SMILES: O=C(C1CCN(c2ccc(CN3CCN(C[C@H](O)CN4CCc5ccccc5C4)C3=O)cn2)CC1)N1CCCC1] | ¹H NMR (400 MHz, Methanol-d4) δ 7.99 (d, J = 2.4 Hz, 1H), 7.48 (dd, J = 8.8, 2.5 Hz, 1H), 7.15-7.06 (m, 3H), 7.03 (dd, J = 5.4, 2.2 Hz, 1H), 6.82 (d, J = 8.9 Hz, 1H), 4.31 (dt, J = 13.2, 3.3 Hz, 2H), 4.21 (dd, J = 8.4, 1.9 Hz, 2H), 4.05 (tt, J = 7.2, 4.6 Hz, 1H), 3.74 (d, J = 2.2 Hz, 2H), 3.61 (t, J = 6.8 Hz, 2H), 3.54-3.45 (m, 2H), 3.43-3.34 (m, 3H), 3.28-3.11 (m, 4H), 2.95-2.84 (m, 5H), 2.78 (ddt, J = 11.4, 7.2, 4.0 Hz, 1H), 2.66-2.56 (m, 2H), 2.00 (p, J = 6.8 Hz, 2H), 1.93-1.85 (m, 2H), 1.82-1.64 (m, 4H). LCMS: 547.5 [M + H]⁺. |
| 18 | 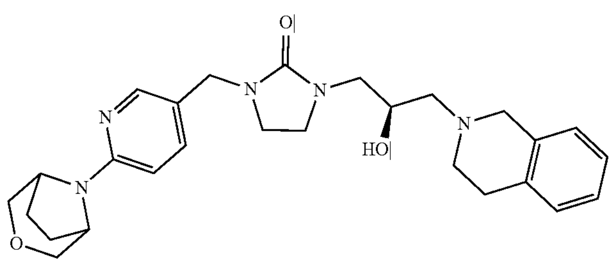 | ¹H NMR (400 MHz, DMSO-d6) δ 7.99 (dd, J = 2.3, 0.7 Hz, 1H), 7.40 (dd, J = 8.6, 2.4 Hz, 1H), 7.16-7.06 (m, 3H), 7.03 (d, J = 5.0 Hz, 1H), 6.77 (dd, J = 8.7, 0.8 Hz, 1H), 4.73 (s, 1H), 4.42 (s, 2H), 4.12 (s, 2H), 3.85 (s, 1H), 3.61 (d, J = 10.8 Hz, 3H), 3.51-3.46 (m, 2H), 3.44-3.36 (m, 1H), 3.31-3.22 (m, 3H), 3.19-3.08 (m, 3H), 3.00 (dd, J = 13.8, 7.1 Hz, 1H), 2.79 (s, 2H), 2.70 (s, 2H), 2.44 (d, J = 9.5 Hz, 1H), 1.98-1.89 (m, 2H), 1.81 (dd, J = 8.1, 4.2 Hz, 2H). LCMS: 478.8 [M + H]⁺. |
| 19 | 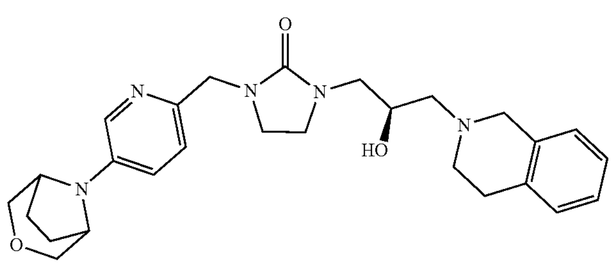 [SMILES: O=C1N(Cc2ccc(N3C4CCC3COC4)cn2)CCN1C[C@H](O)CN1CCc2ccccc2C1] | ¹H NMR (400 MHz, Methanol-d4) δ 8.07 (dd, J = 2.9, 0.7 Hz, 1H), 7.29 (dd, J = 8.7, 2.9 Hz, 1H), 7.25-7.20 (m, 1H), 7.13-7.06 (m, 3H), 7.05-7.00 (m, 1H), 4.35 (s, 2H), 4.22-4.14 (m, 2H), 4.07 (tt, J = 7.3, 7.3, 4.6, 4.6 Hz, 1H), 3.82 (d, J = 10.9 Hz, 2H), 3.73 (s, 2H), 3.58-3.47 (m, 4H), 3.41-3.32 (m, 3H), 3.19 (dd, J = 14.2, 7.1 Hz, 1H), 2.95-2.81 (m, 4H), 2.67-2.53 (m, 2H), 2.13-1.95 (m, 4H); LCMS: 478.3 [M + H]⁺. |
| 20 | 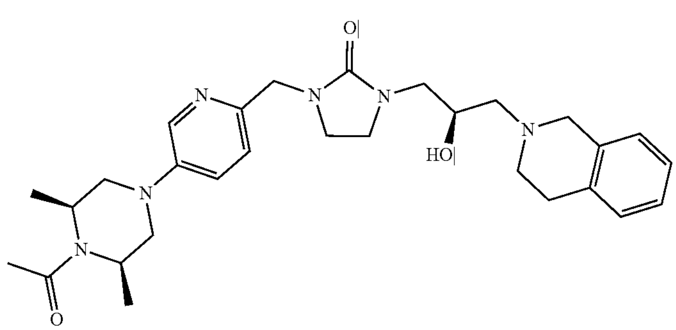 | ¹H NMR (400 MHz, DMSO-d6) δ 7.99 (d, J = 2.4 Hz, 1H), 7.42 (dd, J = 8.8, 2.4 Hz, 1H), 7.09 (dd, J = 5.4, 3.6 Hz, 3H), 7.05-7.00 (m, 1H), 6.90 (d, J = 8.7 Hz, 1H), 4.73 (d, J = 4.8 Hz, 1H), 4.20 (d, J = 12.9 Hz, 2H), 4.13 (s, 2H), 3.85 (s, 1H), 3.60 (s, 2H), 3.39 (d, J = 7.9 Hz, 1H), 2.36-2.31 (m, 2H), 3.26 (dd, J = 13.9, 4.1 Hz, 1H), 3.10 (t, J = 7.9, 7.9 Hz, 2H), 3.00 (dd, J = 13.9, 7.2 Hz, 1H), 2.91 (s, 3H), 2.79 (t, J = 5.9, 5.9 Hz, 2H), 2.70 (dd, J = 5.7, 3.5 Hz, 1H), 2.43 (dd, J = 6.1, 2.6 Hz, 2H), 2.05 (s, 3H), 2.00 (q, J = 6.8, 6.8, 6.1 Hz, 1H), 1.24 (s, 6H); LCMS: 521.3 [M + H]⁺. |

TABLE 1-continued

| Comp. No | Structure | Characterization Data |
|---|---|---|
| 21 | 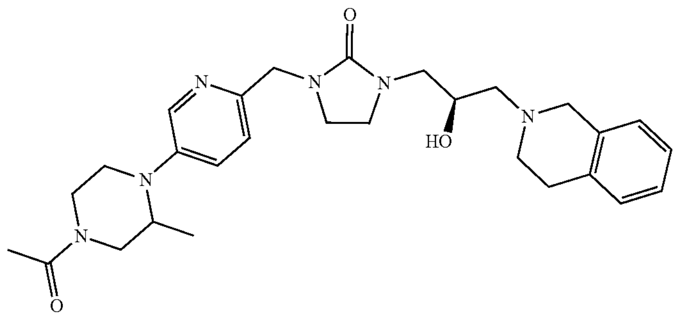 [SMILES: CC(=O)N1CCN(c2ccc(CN3CCN(C[C@H](O)CN4CCc5ccccc5C4)C3=O)nc2)C(C)C1] | ¹H NMR (400 MHz, Methanol-d4) δ 8.04 (t, J = 2.1, 2.1 Hz, 1H), 7.51 (dd, J = 8.8, 2.5 Hz, 1H), 7.14-7.01 (m, 4H), 6.80-6.74 (m, 1H), 5.37-5.30 (m, 1H), 4.60-4.41 (m, 2H), 4.39-4.28 (m, 1H), 4.24 (d, J = 1.7 Hz, 2H), 4.13-3.92 (m, 2H), 3.82 (d, J = 11.7 Hz, 2H), 3.57-3.45 (m, 2H), 3.38-3.33 (m, 2H), 3.27-3.14 (m, 4H), 3.11-3.02 (m, 2H), 2.94 (s, 4H), 2.66 (dd, J = 8.8, 2.7 Hz, 2H), 2.24-2.16 (m, 2H), 2.12 (s, 1H), 2.02 (d, J = 6.5 Hz, 2H); LCMS: 507.3 [M + H]⁺. |
| 22 | 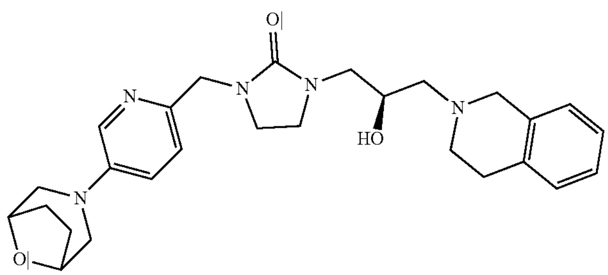 | ¹H NMR (400 MHz, DMSO-d6) δ 8.11 (d, J = 2.9 Hz, 1H), 7.20 (dd, J = 8.7, 3.0 Hz, 1H), 7.14-7.00 (m, 5H), 4.73 (d, J = 4.8 Hz, 1H), 4.42 (d, J = 3.3 Hz, 2H), 4.23 (s, 2H), 4.12 (q, J = 5.3, 5.3, 5.3 Hz, 1H), 3.85 (p, J = 5.7, 5.7, 5.7, 5.7 Hz, 1H), 3.60 (s, 2H), 3.47-3.37 (m, 4H), 3.27 (dd, J = 13.9, 4.1 Hz, 1H), 3.22-3.14 (m, 3H), 3.00 (dd, J = 13.9, 7.2 Hz, 1H), 2.81 (dt, J = 11.7, 3.7, 3.7 Hz, 2H), 2.71 (p, J = 5.9, 5.9, 5.8, 5.8 Hz, 2H), 2.46-2.38 (m, 2H), 1.83 (t, J = 2.7, 2.7 Hz, 4H); LCMS: 478.1 [M + H]⁺. |
| 23 | 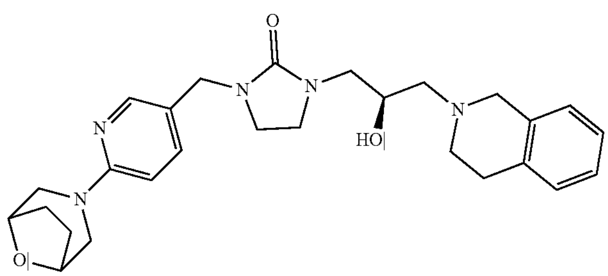 | ¹H NMR (300 MHz, DMSO-d6) δ7.98 (d, J = 2.4 Hz, 1H), 7.40 (dd, J = 8.7, 2.5 Hz, 1H), 7.13-6.98 (m, 4H), 6.69 (d, J = 8.7 Hz, 1H), 4.72 (s, 1H), 4.41 (s, 2H), 4.12 (s, 2H), 3.85 (s, 1H), 3.81-3.71 (m, 2H), 3.64-3.56 (m, 2H), ), 3.37 (dq, J = 1.7, 0.6, 0.6, 0.6 Hz, 1H), 3.32-3.20 (m, 2H), 3.04 (dt, J = 21.6, 7.2, 7.2 Hz, 3H), 2.89 (dd, J = 12.4, 2.6 Hz, 2H), 2.79 (d, J = 5.6 Hz, 2H), 2.75-2.67 (m, 2H), 2.46-2.37 (m, 2H), 1.89-1.66 (m, 4H). LCMS: 478.1 [M + H]⁺. |
| 24 | 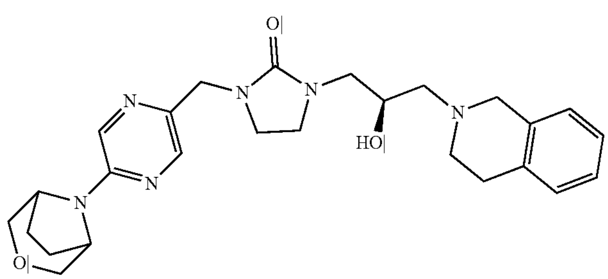 | ¹H NMR (400 MHz, Methanol-d4) δ 8.11 (d, J = 1.4 Hz, 1H), 8.08 (d, J = 1.4 Hz, 1H), 7.36-7.17 (m, 1H), 7.14-7.00 (m, 3H), 4.52 (d, J = 4.5 Hz, 2H), 4.35 (s, 2H), 4.07 (tt, J = 6.9, 6.9, 4.6, 4.6 Hz, 1H), 3.81-3.70 (m, 4H), 3.64-3.47 (m, 4H), 3.44-3.35 (m, 3H), 3.19 (dd, J = 14.2, 7.0 Hz, 1H), 2.92 (t, J = 6.0, 6.0 Hz, 2H), 2.85 (dd, J = 6.6, 4.2 Hz, 2H), 2.65-2.54 (m, 2H), 2.15-1.96 (m, 4H); LCMS: 479.0 [M + H]⁺. |
| 25 | 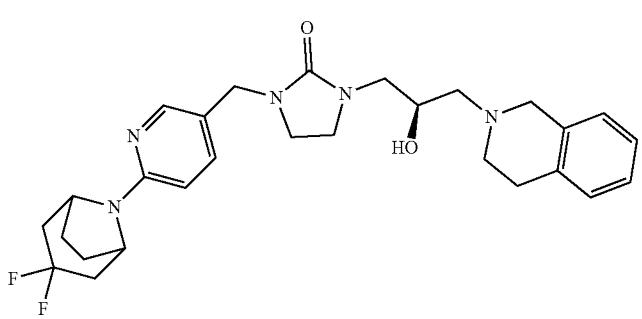 [SMILES: O=C1N(Cc2ccc(N3C4CCC3CC(F)(F)C4)nc2)CCN1C[C@H](O)CN1CCc2ccccc2C1] | ¹H NMR (300 MHz, DMSO-d6) δ 8.04 (d, J = 2.3 Hz, 1H), 7.45 (dd, J = 8.6, 2.4 Hz, 1H), 7.07 (d, J = 17.3 Hz, 4H), 6.84 (d, J = 8.6 Hz, 1H), 4.73 (s, 1H), 4.61 (s, 2H), 4.14 (s, 2H), 3.93-3.81 (m, 1H), 3.69-3.55 (m, 2H), 3.45-3.39 (m, 2H), 3.30-3.20 (m, 2H), 3.15-3.09 (m, 2H), 3.07-2.95 (m, 2H), 2.80 (s, 2H), 2.75-2.70 (m, 1H), 2.44 (dq, J = 3.7, 1.8, 1.8, 1.8 Hz, 2H), 2.09 (d, J = 3.6 Hz, 2H), 1.95 (dt, J = 19.8, 10.4, 10.4 Hz, 5H); LCMS: 512.1 [M + H]⁺. |

TABLE 1-continued

| Comp. No | Structure | Characterization Data |
|---|---|---|
| 26 | 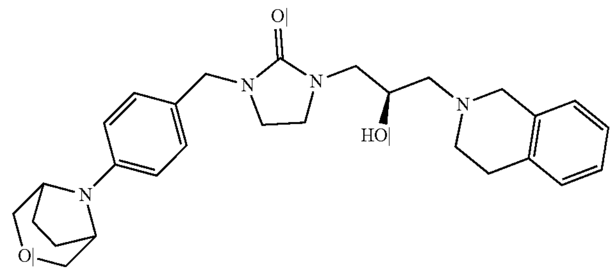 | $^1$H NMR (400 MHz, DMSO-d6) δ 7.14-6.99 (m, 6H), 6.81 (s, 1H), 6.79 (s, 1H), 4.73 (s, 1H), 4.12 (s, 3H), 3.85 (s, 2H), 3.68 (d, J = 10.7 Hz, 2H), 3.60 (s, 2H), 2.37-2.31 (m, 2H), 3.41 (d, J = 10.2 Hz, 2H), 3.31-3.23 (m, 2H), 3.09 (t, J = 7.9, 7.9 Hz, 3H), 3.00 (dd, J = 13.8, 7.0 Hz, 1H), 2.79 (d, J = 5.8 Hz, 2H), 2.70 (s, 1H), 2.43 (s, 1H), 1.96-1.82 (m, 4H); LCMS: 477.3 [M + H]$^+$. |
| 27 | 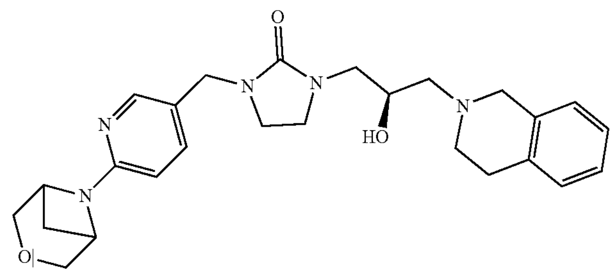 | $^1$H NMR (400 MHz, DMSO-d6) δ 8.00 (dd, J = 2.4, 0.8 Hz, 1H), 7.41 (dd, J = 8.5, 2.4 Hz, 1H), 7.15-6.98 (m, 4H), 6.53 (dd, J = 8.4, 0.8 Hz, 1H), 4.73 (d, J = 4.8 Hz, 1H), 4.29 (d, J = 6.1 Hz, 2H), 4.14 (d, J = 9.6 Hz, 3H), 3.85 (d, J = 5.4 Hz, 1H), 3.67-3.58 (m, 4H), 3.46-3.38 (m, 2H), 3.30-3.22 (m, 2H), 3.12 (t, J = 7.9, 7.9 Hz, 2H), 3.00 (dd, J = 13.9, 7.2 Hz, 1H), 2.79 (t, J = 5.8, 5.8 Hz, 2H), 2.73-2.60 (m, 3H), 2.47-2.38 (m, 2H), 1.78 (d, J = 8.1 Hz, 1H); LCMS: 464.3 [M + H]$^+$. |
| 28 | 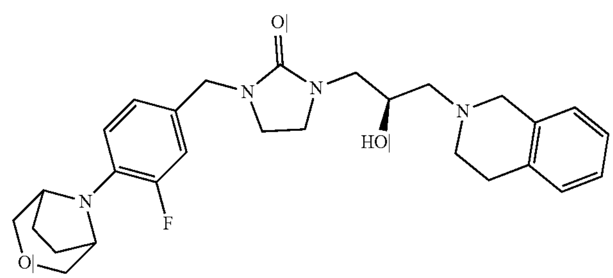 | $^1$H NMR (400 MHz, DMSO-d6) δ 7.13-7.06 (m, 3H), 7.02 (d, J = 5.1 Hz, 1H), 7.00-6.88 (m, 3H), 4.73 (s, 1H), 4.15 (s, 2H), 3.95 (s, 1H), 3.86 (s, 1H), 3.71 (d, J = 10.6 Hz, 2H), 3.60 (s, 2H), 2.37-2.27 (m, 2H), 3.50 (dd, J = 10.9, 1.9 Hz, 2H), 3.40 (dd, J = 8.8, 7.5 Hz, 1H), 3.31-3.21 (m, 2H), 3.11 (t, J = 7.9, 7.9 Hz, 2H), 3.01 (dd, J = 13.8, 7.1 Hz, 1H), 2.80 (s, 2H), 2.70 (s, 2H), 2.44 (d, J = 6.4 Hz, 1H), 1.86 (dt, J = 11.6, 8.2, 8.2 Hz, 4H); LCMS: 495.2 [M + H]$^+$. |
| 29 | 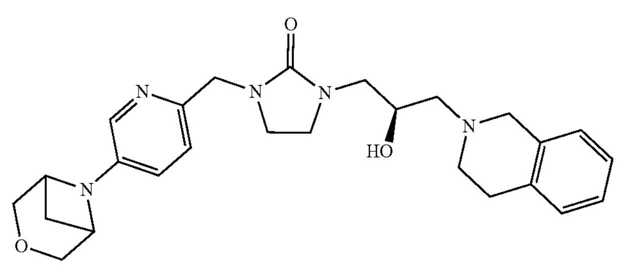 [SMILES: O=C1N(Cc2ccc(N3C4COCC3C4)cn2)CCN1C[C@H](O)CN1CCc2ccccc2C1] | $^1$H NMR (400 MHz, DMSO-d6) δ 7.88 (d, J = 2.7 Hz, 1H), 7.19-6.91 (m, 6H), 4.73 (d, J = 4.7 Hz, 1H), 4.30 (d, J = 6.1 Hz, 2H), 4.23 (s, 2H), 4.11 (d, J = 10.7 Hz, 2H), 3.87 (d, J = 6.5 Hz, 1H), 3.66-3.58 (m, 3H), 3.47-3.35 (m, 2H), 3.30-3.20 (m, 3H), 3.01 (dd, J = 13.9, 7.2 Hz, 1H), 2.79 (d, J = 5.7 Hz, 2H), 2.69 (d, J = 7.5 Hz, 3H), 2.43 (d, J = 6.2 Hz, 3H), 1.82 (d, J = 8.1 Hz, 1H); LCMS: 464.2 [M + H]$^+$. |
| 30 | 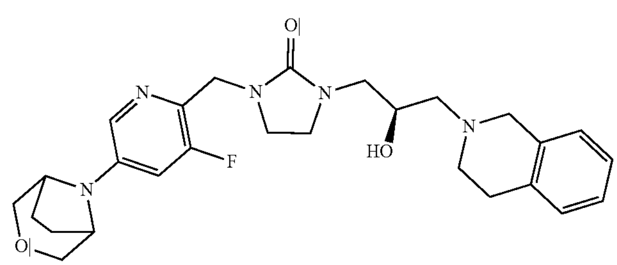 | $^1$H NMR (400 MHz, DMSO-d6) δ 8.00 (t, J = 1.9, 1.9 Hz, 1H), 7.16 (dd, J = 13.1, 2.3 Hz, 1H), 7.12-7.03 (m, 3H), 6.99 (dd, J = 6.7, 2.4 Hz, 1H), 4.71 (s, 1H), 4.24 (dd, J = 23.3, 3.0 Hz, 3H), 3.82 (s, 1H), 3.61 (t, J = 11.1, 11.1 Hz, 3H), 3.43-3.36 (m, 3H), 3.26-3.09 (m, 4H), 2.95 (dd, J = 13.9, 7.1 Hz, 1H), 2.76 (d, J = 5.6 Hz, 2H), 2.69 (s, 2H), 2.41 (d, J = 6.0 Hz, 2H), 1.96-1.82 (m, 4H), 1.52 (q, J = 8.1, 7.6, 7.6 Hz, 1H), 1.28 (dt, J = 14.8, 7.2, 7.2 Hz, 1H); LCMS: 496.3 [M + H]$^+$. |

TABLE 1-continued

| Comp. No | Structure | Characterization Data |
|---|---|---|
| 31 | 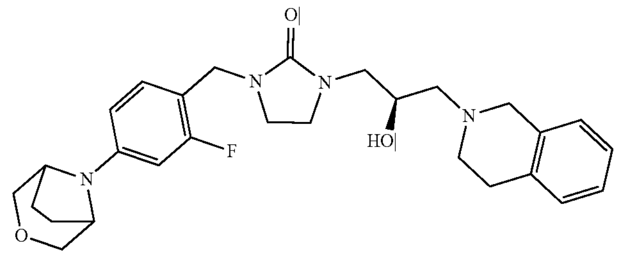 | ¹H NMR (400 MHz, Methanol-d4) δ 7.18-7.07 (m, 4H), 7.04-7.00 (m, 1H), 6.65-6.56 (m, 2H), 4.29 (d, J = 1.6 Hz, 2H), 4.12-4.01 (m, 3H), 3.82 (d, J = 10.9 Hz, 2H), 3.74 (s, 2H), 3.53-3.45 (m, 3H), 3.34 (d, J = 4.6 Hz, 1H), 3.26 (d, J = 8.4 Hz, 2H), 3.16 (dd, J = 14.2, 6.9 Hz, 2H), 2.89 (dd, J = 15.1, 5.0 Hz, 4H), 2.66-2.55 (m, 2H), 2.06-1.94 (m, 4H); LCMS: 495.2 [M + H]⁺. |

Example-II: Synthesis of (R)-1-((6-(1-acetylpiperidin-4-yl)pyridin-3-yl)methyl)-3-(3-(3,4-dihydroisoquinolin-2(1H)-yl)-2-hydroxypropyl)imidazolidin-2-one Compound-32

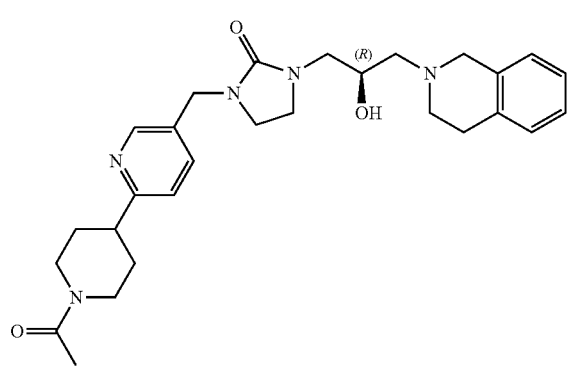

Step-a: Synthesis of tert-butyl (R)-5-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[2,4'-bipyridine]-1'(2'H)-carboxylate To a sealed tube, were added (R)-1-((6-bromopyridin-3-yl)methyl)-3-(2-((tert-butyldimethylsilyl)oxy)-3-(3,4-dihydroisoquinolin-2(1H)-yl)propyl)imidazolidin-2-one (Intermediate-3) (10.0 g, 17.869 mmol), DME/H₂O (4:1) (250 mL), the reaction mixture was degassed with argon gas for 10 minutes. To this reaction mixture were added tert-butyl 4-(4,4,5,5-tetramethyl-1,3,2-dioxaborolan-2-yl)-3,6-dihydropyridine-1(2H)-carboxylate (6.63 g, 21.443 mmol), Sodium carbonate (4.73 g, 44.673 mmol) and Pd(dppf)Cl₂ (1.459 g, 1.787 mmol) and stirred for 12 h at 70° C. After completion of reaction (monitored by TLC, eluent: 5% methanol in DCM), the reaction mixture was diluted with water and extracted with ethyl acetate and the combined organics were washed with brine solution, dried over anhydrous sodium sulphate and concentrated under reduced pressure. The obtained residue was purified by column chromatography (SiO₂, 3-5% MeOH in DCM) to get (11.0 g, 93.37%) of tert-butyl (R)-5-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[2,4'-bipyridine]-1'(2'H)-carboxylate. LCMS: 662.6 [M+H]⁺.

Step-b: Synthesis of tert-butyl (R)-4-(5-((3-(2-((tert-butyldimethylsilyl)oxy)-3-(3,4-dihydroisoquinolin-2(1H)-yl)propyl)-2-oxoimidazolidin-1-yl)methyl)pyridin-2-yl)piperidine-1-carboxylate A mixture of tert-butyl (R)-5-((3-(2-((tert-butyldimethylsilyl)oxy)-3-(3,4-dihydroisoquinolin-2(1H)-yl)propyl)-2-oxoimidazolidin-1-yl)methyl)-3',6'-dihydro-[2,4'-bipyridine]-1'(2'H)-carboxylate (11.0 g, 16.617 mmol) and 10% Pd—C (3.3 g) in 300 mL of ethanol was taken in parr shaker vessel and hydrogenated at 60 psi pressure for 12 h at RT. After completion of reaction (monitored by TLC, eluent: 5% methanol in DCM), the reaction mixture was filtered through celite bed and filtrate was concentrated under reduced pressure. The obtained residue was purified by column chromatography (SiO₂, 3-5% MeOH in DCM) to get (9.5 g, 86.36%) of tert-butyl (R)-4-(5-((3-(2-((tert-butyldimethylsilyl)oxy)-3-(3,4-dihydroisoquinolin-2(1H)-yl)propyl)-2-oxoimidazolidin-1-yl)methyl)pyridin-2-yl)piperidine-1-carboxylate. LCMS: 664.2 [M+H]⁺.

Step-c: Synthesis of (R)-1-(2-((tert-butyldimethylsilyl)oxy)-3-(3,4-dihydroisoquinolin-2(1H)-yl)propyl)-3-((6-(piperidin-4-yl)pyridin-3-yl)methyl)imidazolidin-2-one To a stirred solution of tert-butyl (R)-4-(5-((3-(2-((tert-butyldimethylsilyl)oxy)-3-(3,4-dihydroisoquinolin-2(1H)-yl)propyl)-2-oxoimidazolidin-1-yl)methyl)pyridin-2-yl)piperidine-1-carboxylate (9.5 g, 14.308 mmol) in 200.0 mL of DCM, was added TFA (8.15 g, 71.54 mmol) at 0° C. temperature and stirred for 12 h at RT. After completion of reaction (monitored by TLC, eluent: 10% methanol in DCM), the reaction mixture was concentrated under reduced pressure. The obtained residue was diluted with water and basified with sodium carbonate and extracted with DCM. The combined organics were washed with brine solution, anhydrous sodium sulphate and concentrated under reduced pressure to get 6.0 g of (R)-1-(2-((tert-butyldimethylsilyl)oxy)-3-(3,4-dihydroisoquinolin-2(1H)-yl)propyl)-3-((6-(piperidin-4-yl)pyridin-3-yl)methyl)imidazolidin-2-one. LCMS: 564.5 [M+H]⁺.

Step-d: Synthesis of (R)-1-((6-(1-acetylpiperidin-4-yl)pyridin-3-yl)methyl)-3-(2-((tert-butyldimethylsilyl)oxy)-3-(3,4-dihydroisoquinolin-2(1H)-yl)propyl)imidazolidin-2-one To a stirred solution of (R)-1-(2-((tert-butyldimethylsilyl)oxy)-3-(3,4-dihydroisoquinolin-2(1H)-yl)propyl)-3-((6-(piperidin-4-yl)pyridin-3-yl)methyl)imidazolidin-2-one (6.0 g, 10.614 mmol) in 180 mL of DCM were added TEA (3.23 g, 31.923 mmol) and acetic anhydride (1.086 g, 10.641 mmol) at 0° C. and allowed to stirred for 12 h at same temperature. After completion of reaction (monitored by TLC, eluent: 10% methanol in DCM), the reaction mixture was diluted with DCM and washed with saturated sodium bicarbonate solution, water, brine solution and anhydrous sodium sulphate and concentrated under reduced pressure. The obtained residue was purified by column chromatography (SiO$_2$, 3-5% MeOH in DCM) to get (4.5 g, 74.3%) of (R)-1-((6-(1-acetylpiperidin-4-yl)pyridin-3-yl)methyl)-3-(2-((tert-butyldimethylsilyl)oxy)-3-(3,4-dihydroisoquinolin-2(1H)-yl)propyl)imidazolidin-2-one. LCMS: 606.8 [M+H]$^+$.

Step-e: Synthesis of (R)-1-((6-(1-acetylpiperidin-4-yl)pyridin-3-yl)methyl)-3-(3-(3,4-dihydroisoquinolin-2(1H)-yl)-2-hydroxypropyl)imidazolidin2-one To a stirred solution of (R)-1-((6-(1-acetylpiperidin-4-yl)pyridin-3-yl)methyl)-3-(2-((tert-butyldimethylsilyl)oxy)-3-(3,4-dihydroisoquinolin-2(1H)-yl)propyl)imidazolidin-2-one (4.5 g, 7.427 mmol) in 90.0 mL of THF was added TBAF (1M solution in THF) (22.3 mL, 22.281 mmol) at 0° C. and the reaction mixture was stirred for 12 h at RT. After completion of reaction (monitored by TLC, eluent: 5% methanol in DCM), the reaction mixture was concentrated under reduced pressure and obtained residue was diluted with water and extracted with ethyl acetate. The combined organics were washed with brine solution and dried over anhydrous sodium sulphate. The obtained residue was purified by column chromatography (SiO$_2$, 3-5% MeOH in DCM) to get (3.0 g, 82.6%) of (R)-1-((6-(1-acetylpiperidin-4-yl)pyridin-3-yl)methyl)-3-(3-(3,4-dihydroisoquinolin-2(1H)-yl)-2-hydroxypropyl)imidazolidin-2-one. $^1$H NMR (600 MHz, DMSO-d$_6$) δ 8.42 (t, J=1.8 Hz, 1H), 7.66 (dt, J=8.1, 1.9 Hz, 1H), 7.19 (d, J=8.0 Hz, 1H), 7.09 (p, J=4.8, 4.4 Hz, 3H), 7.03 (d, J=6.6 Hz, 1H), 4.74 (s, 1H), 4.53 (d, J=13.0 Hz, 1H), 4.38 (d, J=13.3 Hz, 1H), 4.32 (d, J=1.5 Hz, 2H), 3.88 (s, 1H), 3.61 (s, 2H), 3.49-3.37 (m, 2H), 3.31-3.24 (m, 3H), 1.12-1.06 (m, 1H), 3.17 (t, J=13.1 Hz, 1H), 3.02 (dd, J=13.9, 7.1 Hz, 1H), 2.83 (ddt, J=23.3, 10.8, 4.5 Hz, 3H), 2.71 (s, 2H), 2.61 (q, J=15.5, 14.2 Hz, 1H), 2.46-2.37 (m, 2H), 2.00 (dt, J=9.4, 6.2 Hz, 1H), 1.84 (d, J=13.0 Hz, 1H), 1.76 (d, J=12.9 Hz, 1H), 1.59 (d, J=13.3 Hz, 1H), 1.46 (d, J=13.4 Hz, 1H), 1.23 (s, 1H). LCMS: 492.4 [M+H]$^+$.

The compounds listed in below Table-2 were prepared by procedure similar to the one described in Example-II with appropriate variations in reactants, quantities of reagents, protections and deprotections, solvents and reaction conditions. The characterization data of the compounds are summarized herein the below table.

TABLE 2

| Comp. No | Structure | Characterization Data |
|---|---|---|
| 33 | 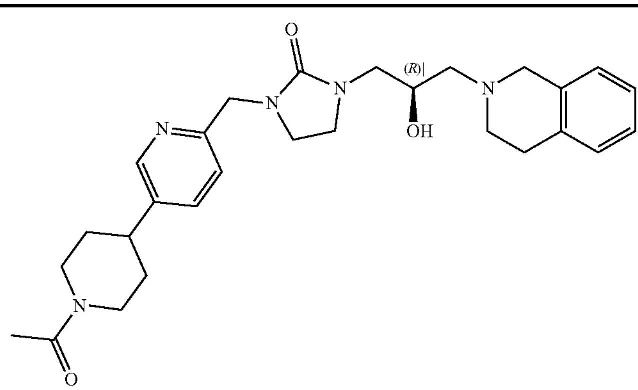 | $^1$H NMR (400 MHz, DMSO-d6) δ 8.42-8.39 (m, 1H), 7.65 (dd, J = 8.1, 2.4 Hz, 1H), 7.21-7.17 (m, 1H), 7.09 (dd, J = 5.2, 3.5 Hz, 3H), 7.05-6.99 (m, 1H), 4.74 (d, J = 4.8 Hz, 1H), 4.56-4.48 (m, 1H), 4.31 (s, 2H), 3.89 (dd, J = 17.2, 10.3 Hz, 2H), 3.60 (s, 2H), 3.50-3.36 (m, 2H), 3.31-3.21 (m, 3H), 3.11 (td, J = 13.5, 13.1, 2.6 Hz, 1H), 3.01 (dd, J = 13.8, 7.2 Hz, 1H), 2.80 (t, J = 5.7 Hz, 3H), 2.70 (q, J = 6.0, 5.5 Hz, 2H), 2.62-2.52 (m, 1H), 2.46-2.39 (m, 2H), 2.02 (s, 3H), 1.76 (t, J = 13.7 Hz, 2H), 1.61 (td, J = 12.5, 4.2 Hz, 1H), 1.50-1.38 (m, 1H); LCMS: 492.4 [M + H]$^+$. |
| 34 | 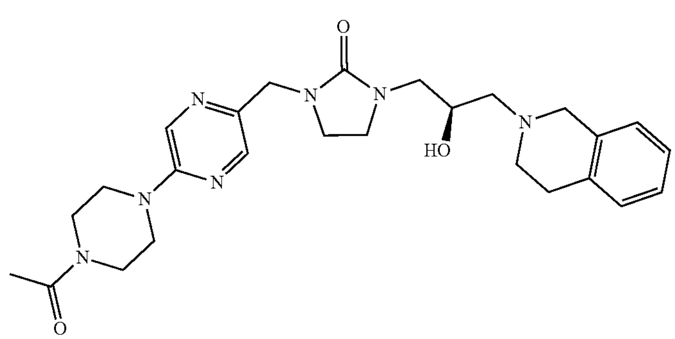 [SMILES: CC(=O)N1CCN(c2cnc(CN3CCN(C[C@H](O)CN4CCc5ccccc5C4)C3=O)cn2)CC1] | $^1$H NMR (600 MHz, DMSO-d6) δ 8.55 (d, J = 1.7 Hz, 1H), 8.48 (d, J = 1.6 Hz, 1H), 7.13-7.05 (m, 3H), 7.02 (d, J = 6.2 Hz, 1H), 4.75 (d, J = 4.7 Hz, 1H), 4.49 (dq, J = 12.8, 2.3 Hz, 1H), 4.39 (s, 2H), 3.94-3.82 (m, 2H), 3.60 (s, 2H), 3.44 (td, J = 16.1, 15.6, 7.9 Hz, 1H), 3.31-3.23 (m, 4H), 3.15 (td, J = 13.0, 2.4 Hz, 1H), 3.06-2.97 (m, 2H), 2.78 (d, J = 5.9 Hz, 2H), 2.70 (h, J = 5.4, 5.0 Hz, 2H), 2.62 (td, J = 13.0, 2.4 Hz, 1H), 2.43 (t, J = 5.6 Hz, 2H), 2.02 (d, J = 1.5 Hz, 3H), 1.89-1.80 (m, 2H), 1.68 (qd, J = 12.4, 4.1 Hz, 1H), 1.53 (qd, J = 12.5, 4.2 Hz, 1H); LCMS: 493.4 [M + H]$^+$. |

TABLE 2-continued

| Comp. No | Structure | Characterization Data |
|---|---|---|
| 35 | 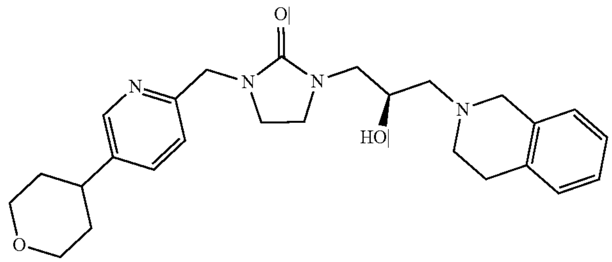 | ¹H NMR (600 MHz, DMSO-d6) δ 8.42 (d, J = 1.9 Hz, 1H), 7.66 (dt, J = 8.0, 1.9 Hz, 1H), 7.23-7.18 (m, 1H), 7.13-7.07 (m, 3H), 7.05-7.01 (m, 1H), 4.75 (s, 1H), 4.32 (d, J = 1.7 Hz, 2H), 3.94 (dt, J = 13.3, 2.8 Hz, 2H), 3.88 (q, J = 5.8, 5.1 Hz, 1H), 3.61 (s, 2H), 3.47-3.37 (m, 4H), 3.30-3.22 (m, 3H), 3.02 (ddd, J = 13.7, 7.2, 1.5 Hz, 1H), 2.84-2.77 (m, 3H), 2.72 (dq, J = 16.0, 8.6, 7.9 Hz, 2H), 2.44 (q, J = 11.6, 8.7 Hz, 2H), 1.67 (tt, J = 5.9, 2.1 Hz, 4H); LCMS: 451.6 [M + H]⁺. |
| 36 | 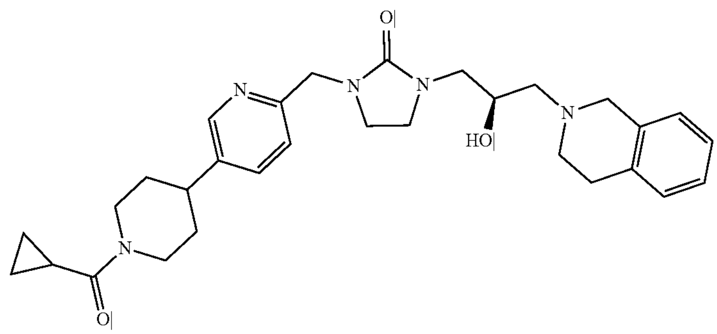 | ¹H NMR (600 MHz, DMSO-d6) δ 8.42 (t, J = 1.8 Hz, 1H), 7.66 (dt, J = 8.1, 1.9 Hz, 1H), 7.19 (d, J = 8.0 Hz, 1H), 7.09 (p, J = 4.8, 4.4 Hz, 3H), 7.03 (d, J = 6.6 Hz, 1H), 4.74 (s, 1H), 4.53 (d, J = 13.0 Hz, 1H), 4.38 (d, J = 13.3 Hz, 1H), 4.32 (d, J = 1.5 Hz, 2H), 3.88 (s, 1H), 3.61 (s, 2H), 3.49-3.37 (m, 2H), 3.31-3.24 (m, 3H), 1.12-1.06 (m, 1H), 3.17 (t, J = 13.1 Hz, 1H), 3.02 (dd, J = 13.9, 7.1 Hz, 1H), 2.83 (ddt, J = 23.3, 10.8, 4.5 Hz, 3H), 2.71 (s, 2H), 2.61 (q, J = 15.5, 14.2 Hz, 1H), 2.00 (dt, J = 9.4, 6.2 Hz, 1H), 1.84 (d, J = 13.0 Hz, 1H), 1.76 (d, J = 12.9 Hz, 1H), 1.59 (d, J = 13.3 Hz, 1H), 1.46 (d, J = 13.4 Hz, 1H), 1.23 (s, 1H), 0.79-0.66 (m, 4H); LCMS: 518.4 [M + H]⁺. |
| 37 | 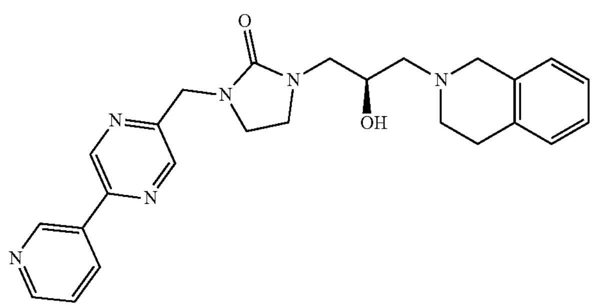 [SMILES: O=C1N(Cc2cnc(-c3cccnc3)cn2)CCN1C[C@H](O)CN1CCc2ccccc2C1] | ¹H NMR (400 MHz, Methanol-d4) δ 9.24 (dd, J = 2.3, 0.9 Hz, 1H), 9.13 (d, J = 1.6 Hz, 1H), 8.71 (d, J = 1.5 Hz, 1H), 8.64 (dd, J = 5.0, 1.6 Hz, 1H), 8.52 (ddd, J = 8.0, 2.3, 1.6 Hz, 1H), 7.59 (ddd, J = 8.1, 5.0, 0.9 Hz, 1H), 7.11-7.05 (m, 3H), 7.04-6.99 (m, 1H), 4.58 (s, 2H), 4.08 (tt, J = 7.2, 4.6 Hz, 1H), 3.73 (s, 2H), 3.63-3.54 (m, 2H), 3.48 (td, J = 7.8, 1.4 Hz, 2H), 3.37 (dd, J = 14.2, 4.4 Hz, 1H), 3.21 (dd, J = 14.2, 7.1 Hz, 1H), 2.90 (d, J = 5.5 Hz, 2H), 2.88-2.81 (m, 2H), 2.65-2.55 (m, 2H); LCMS: 493.4 [M + H]⁺. |
| 38 | 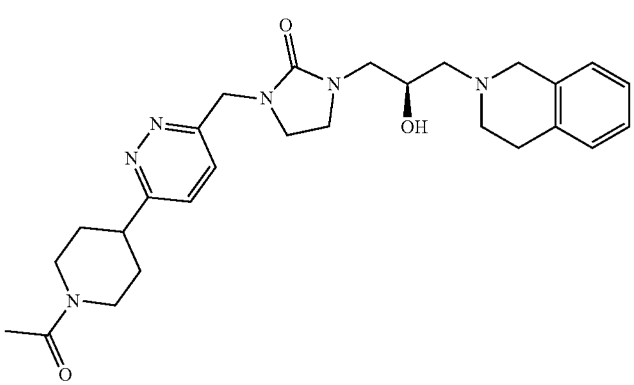 [SMILES: CC(=O)N1CCC(c2ccc(CN3CCN(C[C@H](O)CN4CCc5ccccc5C4)C3=O)nn2)CC1] | ¹H NMR (400 MHz, Methanol-d4) δ 7.67-7.60 (m, 2H), 7.19-7.11 (m, 3H), 7.09-7.04 (m, 1H), 4.71-4.64 (m, 1H), 4.63 (s, 2H), 4.14 (ddd, J = 11.6, 7.2, 4.5 Hz, 1H), 4.06 (ddd, J = 11.3, 4.5, 2.3 Hz, 1H), 3.95 (s, 2H), 3.60-3.55 (m, 2H), 3.45-3.39 (m, 2H), 3.38-3.32 (m, 1H), 3.28-3.16 (m, 3H), 3.08 (t, J = 6.1 Hz, 2H), 3.00 (d, J = 6.0 Hz, 2H), 2.86-2.72 (m, 3H), 2.13 (s, 3H), 2.07-1.93 (m, 2H), 1.78 (dqd, J = 49.3, 12.6, 4.3 Hz, 2H); LCMS: 493.4 [M + H]⁺. |

TABLE 2-continued

| Comp. No | Structure | Characterization Data |
|---|---|---|
| 39 | 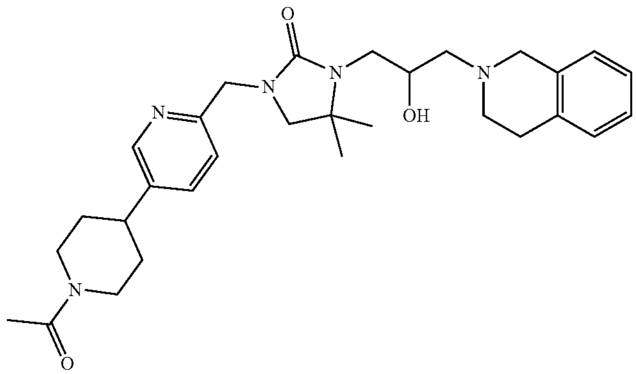 [SMILES: CC(=O)N1CCC(c2ccc(CN3CC(C)(C)N(CC(O)CN4CCc5ccccc5C4)C3=O)nc2)CC1] | ¹H NMR (400 MHz, DMSO-d6) δ 8.43-8.39 (m, 1H), 7.65 (dd, J = 8.1, 2.3 Hz, 1H), 7.18 (d, J = 8.1 Hz, 1H), 7.12-7.00 (m, 4H), 5.32 (s, 1H), 4.87 (s, 1H), 4.52 (d, J = 13.3 Hz, 1H), 4.39-4.27 (m, 2H), 4.05 (dq, J = 1.7, 0.9, 0.9, 0.9 Hz, 3H), 3.91 (d, J = 11.2 Hz, 2H), 3.60 (d, J = 8.4 Hz, 1H), 2.72-2.62 (m, 2H), 3.19 (ddd, J = 17.7, 12.9, 5.6 Hz, 1H), 3.09 (dd, J = 13.5, 5.0 Hz, 2H), 2.90 (dd, J = 14.2, 7.0 Hz, 1H), 2.79 (s, 2H), 2.40 (s, 1H), 2.02 (s, 3H), 1.76 (t, J = 13.7, 13.7 Hz, 2H), 1.64-1.54 (m, 1H), 1.47-1.38 (m, 2H), 1.20 (s, 3H), 1.16 (s, 3H). LCMS: 520.5 [M + H]⁺. |
| 40 | 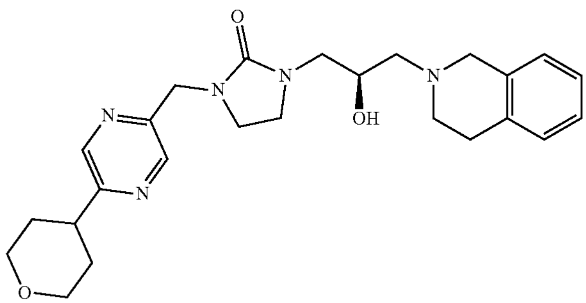 [SMILES: O=C1N(Cc2cnc(C3CCOCC3)cn2)CCN1C[C@H](O)CN1CCc2ccccc2C1] | ¹H NMR (600 MHz, DMSO-d6) δ 8.54 (t, J = 1.5 Hz, 1H), 8.49 (d, J = 1.5 Hz, 1H), 7.13-7.05 (m, 3H), 7.05-6.98 (m, 1H), 4.75 (d, J = 4.8 Hz, 1H), 4.42-4.36 (m, 2H), 3.95 (dt, J = 10.8, 3.0 Hz, 2H), 3.87 (h, J = 5.8 Hz, 1H), 3.60 (s, 2H), 3.49-3.39 (m, 4H), 3.33-3.22 (m, 3H), 3.07-2.99 (m, 2H), 2.79 (t, J = 6.0 Hz, 2H), 2.70 (hept, J = 5.4 Hz, 2H), 2.46-2.38 (m, 2H), 1.81-1.73 (m, 4H); LCMS: 452.5 [M + H]⁺. |
| 41 | 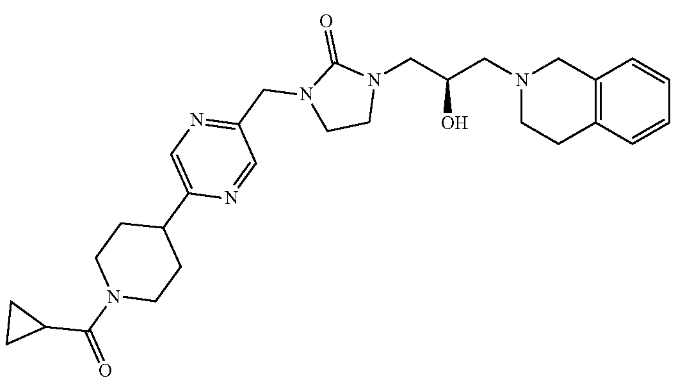 [SMILES: O=C(C1CC1)N1CCC(c2cnc(CN3CCN(C[C@H](O)CN4CCc5ccccc5C4)C3=O)cn2)CC1] | ¹H NMR (600 MHz, DMSO-d6) δ 8.55 (d, J = 1.4 Hz, 1H), 8.48 (s, 1H), 7.09 (dq, J = 9.5, 5.3, 4.6 Hz, 3H), 7.05-7.00 (m, 1H), 4.75 (s, 1H), 4.49 (d, J = 12.7 Hz, 1H), 4.39 (s, 2H), 3.91-3.82 (m, 1H), 3.60 (s, 2H), 3.52-3.41 (m, 2H), 3.33-3.25 (m, 3H), 3.18 (ddd, J = 27.8, 10.9, 6.2 Hz, 3H), 3.04 (ddt, J = 24.8, 13.8, 7.6 Hz, 2H), 2.79 (d, J = 5.8 Hz, 2H), 2.75-2.64 (m, 3H), 2.44 (s, 2H), 2.00 (td, J = 8.2, 7.6, 3.8 Hz, 1H), 1.95-1.89 (m, 1H), 1.83 (d, J = 13.1 Hz, 1H), 1.68 (d, J = 13.4 Hz, 1H), 1.56 (dp, J = 17.1, 6.2, 4.9 Hz, 2H), 1.35-1.21 (m, 2H), 0.78-0.66 (m, 4H); LCMS: 519.4 [M + H]⁺. |
| 42 | 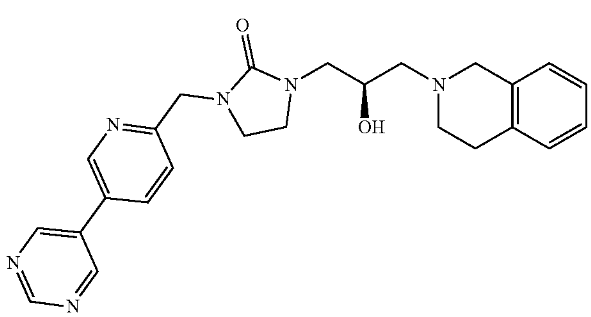 [SMILES: O=C1N(Cc2ccc(-c3cncnc3)cn2)CCN1C[C@H](O)CN1CCc2ccccc2C1] | ¹H NMR (400 MHz, Methanol-d4) δ 9.19 (d, J = 1.0 Hz, 1H), 9.12 (d, J = 1.0 Hz, 2H), 8.86 (dd, J = 2.4, 0.9 Hz, 1H), 8.17 (ddd, J = 8.1, 2.4, 0.9 Hz, 1H), 7.55 (dd, J = 8.1, 0.9 Hz, 1H), 7.09 (dq, J = 4.4, 2.8, 2.2 Hz, 3H), 7.05-6.99 (m, 1H), 4.55 (s, 2H), 4.09 (tt, J = 7.4, 4.6 Hz, 1H), 3.74 (d, J = 1.7 Hz, 2H), 3.63-3.54 (m, 2H), 3.47-3.34 (m, 3H), 3.25-3.18 (m, 1H), 2.91 (d, J = 5.6 Hz, 2H), 2.86 (dd, J = 6.7, 3.6 Hz, 2H), 2.64-2.59 (m, 2H); LCMS: 445.4 [M + H]⁺. |

TABLE 2-continued

| Comp. No | Structure | Characterization Data |
|---|---|---|
| 43 | 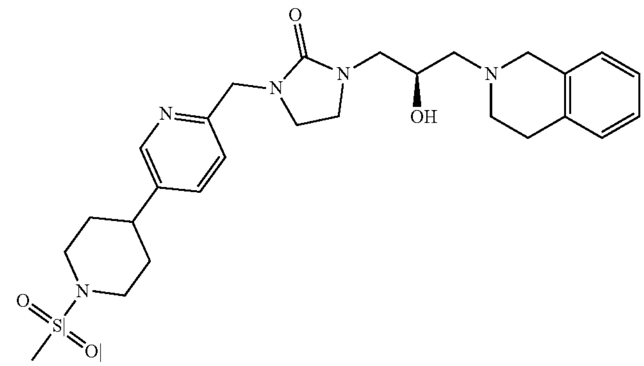 | $^1$H NMR (400 MHz, DMSO-d6) δ 8.45-8.42 (m, 1H), 7.69 (dd, J = 8.1, 2.3 Hz, 1H), 7.20 (d, J = 8.0 Hz, 1H), 7.12-7.06 (m, 3H), 7.05-6.98 (m, 1H), 4.74 (d, J = 4.8 Hz, 1H), 4.32 (s, 2H), 3.87 (s, 1H), 3.67 (d, J = 11.9 Hz, 2H), 3.60 (s, 2H), 3.48-3.37 (m, 2H), 3.31-3.20 (m, 3H), 3.02 (dd, J = 13.9, 7.2 Hz, 1H), 2.90 (d, J = 0.5 Hz, 3H), 2.86-2.77 (m, 4H), 2.74-2.64 (m, 3H), 2.44 (dd, J = 6.1, 3.5 Hz, 2H), 1.86 (d, J = 12.7 Hz, 2H), 1.70 (tt, J = 12.5, 6.3 Hz, 2H); LCMS: 528.4 [M + H]$^+$. |
| 44 | 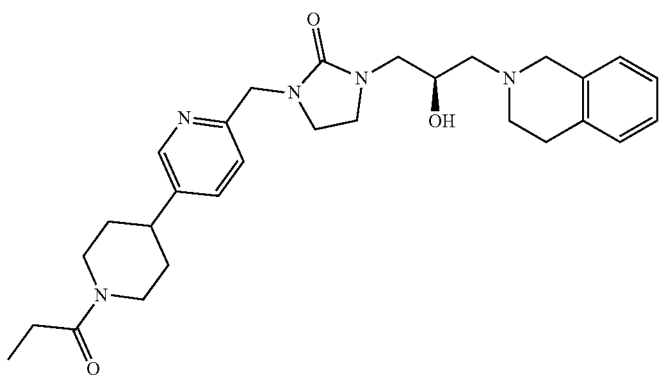 [SMILES: CCC(=O)N1CCC(c2ccc(CN3CCN(C[C@H](O)CN4CCc5ccccc5C4)C3=O)nc2)CC1] | $^1$H NMR (400 MHz, DMSO-d6) δ 8.41 (d, J = 2.3 Hz, 1H), 7.64 (dd, J = 8.1, 2.3 Hz, 1H), 7.19 (d, J = 8.0 Hz, 1H), 7.09 (dd, J = 5.1, 3.4 Hz, 3H), 7.05-6.99 (m, 1H), 4.73 (d, J = 4.8 Hz, 1H), 4.55 (d, J = 13.4 Hz, 1H), 4.31 (s, 2H), 3.96 (d, J = 13.5 Hz, 1H), 3.87 (s, 1H), 3.60 (s, 2H), 3.49-3.37 (m, 3H), 3.25 (dd, J = 9.8, 6.0 Hz, 2H), 3.13-2.96 (m, 2H), 2.80 (t, J = 5.9 Hz, 3H), 2.75-2.65 (m, 2H), 2.44 (d, J = 6.9 Hz, 3H), 2.34 (q, J = 7.4 Hz, 2H), 1.75 (d, J = 12.9 Hz, 2H), 1.57 (d, J = 11.3 Hz, 1H), 1.44 (d, J = 9.1 Hz, 1H), 1.00 (t, J = 7.4 Hz, 3H); LCMS: 506.5 [M + H]$^+$. |
| 45 | 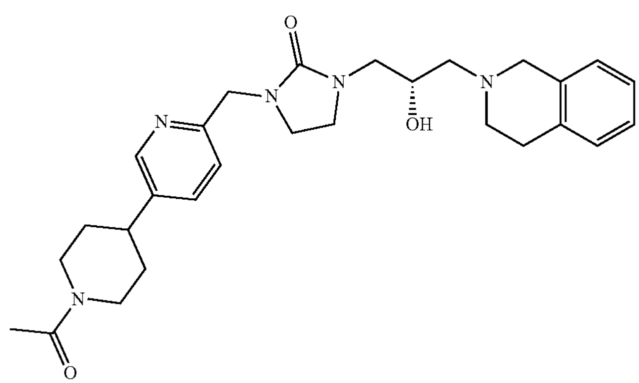 [SMILES: CC(=O)N1CCC(c2ccc(CN3CCN(C[C@@H](O)CN4CCc5ccccc5C4)C3=O)nc2)CC1] | $^1$H NMR (400 MHz, DMSO-d6) δ 8.42-8.39 (m, 1H), 7.67-7.62 (m, 1H), 7.19 (d, J = 8.0 Hz, 1H), 7.09 (dd, J = 5.2, 3.5 Hz, 3H), 7.02 (d, J = 4.5 Hz, 1H), 4.73 (d, J = 4.8 Hz, 1H), 4.52 (d, J = 13.1 Hz, 1H), 4.31 (s, 2H), 3.91 (d, J = 16.2 Hz, 2H), 3.60 (s, 2H), 3.47-3.38 (m, 2H), 3.26-3.21 (m, 4H), 3.11 (s, 1H), 3.05-2.95 (m, 2H), 2.79 (d, J = 6.0 Hz, 2H), 2.75-2.65 (m, 2H), 2.02 (s, 3H), 1.76 (t, J = 13.9 Hz, 2H), 1.65-1.54 (m, 2H), 1.51-1.39 (m, 2H); LCMS: 492.4 [M + H]$^+$. |
| 46 | 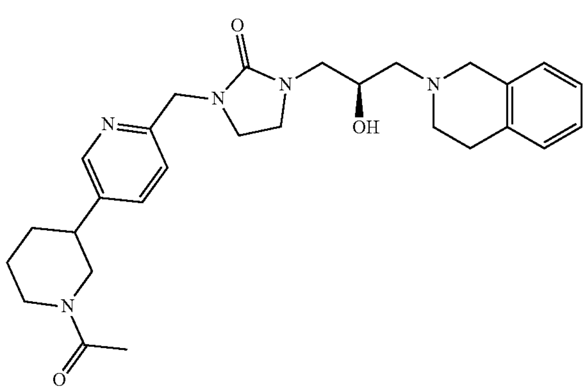 [SMILES: CC(=O)N1CCCC(c2ccc(CN3CCN(C[C@H](O)CN4CCc5ccccc5C4)C3=O)nc2)C1] | $^1$H NMR (400 MHz, DMSO-d6) δ 8.45 (dd, J = 22.9, 2.2 Hz, 1H), 7.69 (ddd, J = 17.4, 8.1, 2.3 Hz, 1H), 7.21 (dd, J = 8.1, 4.1 Hz, 1H), 7.15-6.97 (m, 4H), 4.73 (d, J = 4.8 Hz, 1H), 4.46-4.29 (m, 3H), 3.95-3.75 (m, 2H), 3.61 (s, 2H), 3.44 (dt, J = 24.2, 8.1, 8.1 Hz, 3H), 3.25 (dd, J = 9.6, 6.2 Hz, 3H), 3.18-2.97 (m, 3H), 2.80 (t, J = 5.9, 5.9 Hz, 2H), 2.75-2.62 (m, 3H), 2.44 (dd, J = 6.1, 3.6 Hz, 2H), 2.02 (d, J = 6.8 Hz, 3H), 1.89 (d, J = 12.2 Hz, 1H), 1.79-1.66 (m, 2H); LCMS: 492.4 [M + H]$^+$. |

TABLE 2-continued

| Comp. No | Structure | Characterization Data |
|---|---|---|
| 47 | 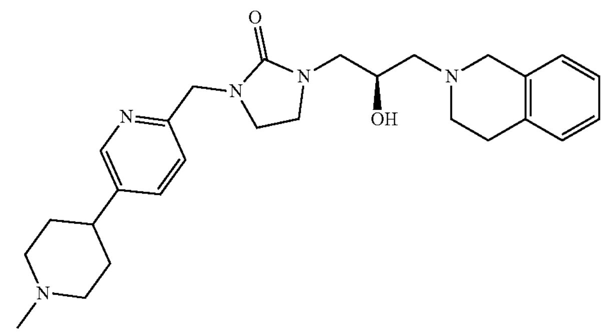 [SMILES: CN1CCC(c2ccc(CN3CCN(C[C@H](O)CN4CCc5ccccc5C4)C3=O)nc2)CC1] | $^1$H NMR (400 MHz, DMSO-d6) δ 8.42-8.38 (m, 1H), 7.64 (dd, J = 8.1, 2.3 Hz, 1H), 7.18 (d, J = 8.0 Hz, 1H), 7.12-7.06 (m, 3H), 7.04-7.00 (m, 1H), 4.73 (d, J = 4.8 Hz, 1H), 4.31 (s, 2H), 3.87 (s, 1H), 3.60 (s, 2H), 3.43 (dt, J = 24.6, 8.2 Hz, 2H), 3.31-3.21 (m, 3H), 3.01 (dd, J = 13.8, 7.2 Hz, 1H), 2.85 (d, J = 11.3 Hz, 3H), 2.79 (d, J = 5.7 Hz, 2H), 2.74-2.65 (m, 2H), 2.45-2.39 (m, 2H), 2.18 (s, 3H), 2.00-1.89 (m, 2H), 1.75-1.59 (m, 4H); LCMS: 464.4 [M + H]$^+$. |
| 48 | 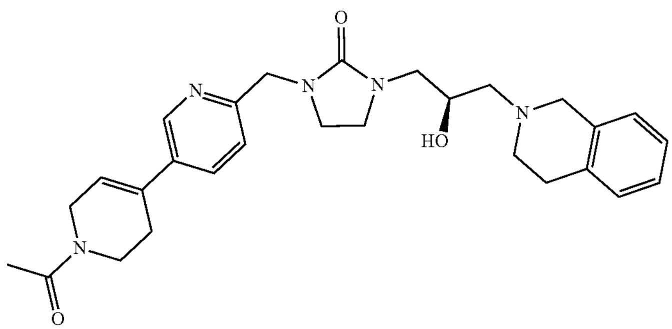 [SMILES: CC(=O)N1CC=C(c2ccc(CN3CCN(C[C@H](O)CN4CCc5ccccc5C4)C3=O)nc2)CC1] | $^1$H NMR (400 MHz, Methanol-d4) δ 8.56 (t, J = 2.8 Hz, 1H), 7.86 (dd, J = 8.2, 2.4 Hz, 1H), 7.36 (d, J = 8.2 Hz, 1H), 7.09 (dd, J = 5.3, 3.3 Hz, 3H), 7.02 (dd, J = 7.5, 2.5 Hz, 1H), 6.23 (ddd, J = 7.1, 3.6, 1.9 Hz, 1H), 4.46 (s, 2H), 4.22 (dq, J = 6.2, 2.9 Hz, 2H), 4.11-4.03 (m, 1H), 3.81 (t, J = 5.8 Hz, 1H), 3.77-3.69 (m, 4H), 3.61-3.51 (m, 2H), 3.41-3.32 (m, 3H), 3.20 (dd, J = 14.2, 7.1 Hz, 1H), 2.94-2.88 (m, 2H), 2.84 (dd, J = 6.6, 3.9 Hz, 2H), 2.66-2.52 (m, 4H), 2.19-2.13 (m, 3H); LCMS: 490.4 [M + H]$^+$. |
| 49 | 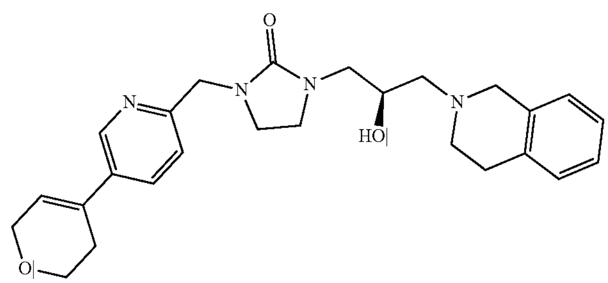 | $^1$H NMR (400 MHz, Methanol-d4) δ 8.55 (dd, J = 2.3, 0.8 Hz, 1H), 7.86 (dd, J = 8.2, 2.4 Hz, 1H), 7.36 (dd, J = 8.2, 0.8 Hz, 1H), 7.12-7.06 (m, 3H), 7.05-7.00 (m, 1H), 6.30 (tt, J = 2.9, 1.6 Hz, 1H), 4.46 (s, 2H), 4.30 (q, J = 2.9 Hz, 2H), 4.08 (ddd, J = 7.2, 4.5, 2.6 Hz, 1H), 3.92 (t, J = 5.5 Hz, 2H), 3.73 (s, 2H), 3.61-3.51 (m, 2H), 3.41-3.33 (m, 3H), 3.20 (dd, J = 14.2, 7.1 Hz, 1H), 2.91 (d, J = 5.6 Hz, 2H), 2.89-2.84 (m, 2H), 2.61 (dd, J = 6.0, 4.3 Hz, 2H), 2.51 (ttd, J = 5.5, 2.8, 1.6 Hz, 2H); LCMS: 449.4 [M + H]$^+$. |
| 50 | 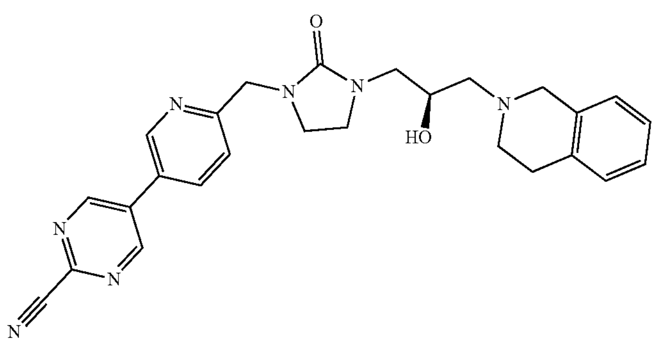 [SMILES: N#Cc1ncc(-c2ccc(CN3CCN(C[C@H](O)CN4CCc5ccccc5C4)C3=O)nc2)cn1] | $^1$H NMR (400 MHz, Methanol-d4) δ 9.26 (d, J = 1.9 Hz, 2H), 8.95-8.91 (m, 1H), 8.24 (dd, J = 8.2, 2.4 Hz, 1H), 7.57 (d, J = 8.2 Hz, 1H), 7.12-7.07 (m, 3H), 7.06-7.01 (m, 1H), 4.56 (s, 2H), 4.09 (tt, J = 7.2, 4.5 Hz, 1H), 3.77-3.72 (m, 2H), 3.63-3.55 (m, 2H), 3.48-3.34 (m, 3H), 3.22 (dd, J = 14.2, 7.2 Hz, 1H), 2.92 (d, J = 5.2 Hz, 2H), 2.87 (dd, J = 6.7, 3.4 Hz, 2H), 2.62 (dd, J = 6.1, 4.1 Hz, 2H); LCMS: 470.4 [M + H]$^+$. |
| 51 | 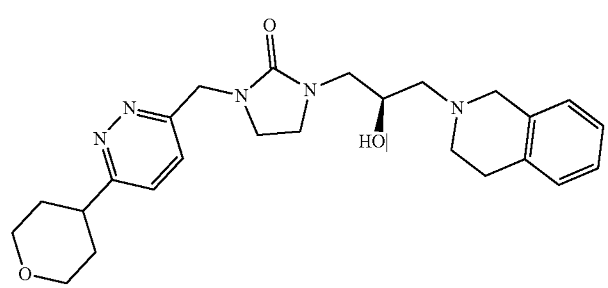 | $^1$H NMR (400 MHz, Methanol-d4) δ 7.67-7.61 (m, 2H), 7.15-7.07 (m, 3H), 7.06-7.01 (m, 1H), 4.63 (s, 2H), 4.12-4.01 (m, 2H), 3.78 (s, 2H), 3.65-3.54 (m, 4H), 3.48-3.34 (m, 2H), 3.20 (ddd, J = 15.8, 7.2, 3.8 Hz, 2H), 2.99-2.87 (m, 4H), 2.68-2.59 (m, 2H), 1.99-1.79 (m, 4H), 1.44-1.26 (m, 3H); LCMS: 452.4 [M + H]$^+$. |

TABLE 2-continued

| Comp. No | Structure | Characterization Data |
|---|---|---|
| 52 | 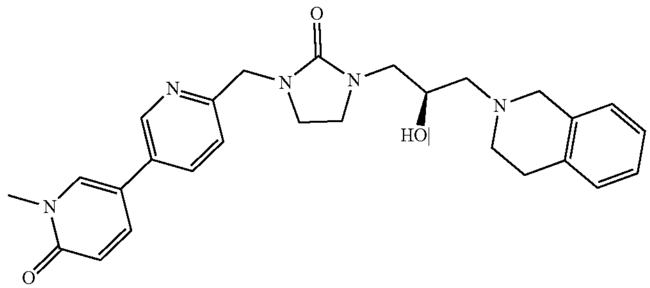 | $^1$H NMR (300 MHz, Chloroform-d) δ 8.60 (d, J = 2.4 Hz, 1H), 7.69 (dd, J = 8.1, 2.5 Hz, 1H), 7.58 (dd, J = 9.4, 2.7 Hz, 1H), 7.51 (d, J = 2.7 Hz, 1H), 7.38 (d, J = 8.1 Hz, 1H), 7.20-7.08 (m, 3H), 7.04-6.98 (m, 1H), 6.70 (d, J = 9.4 Hz, 1H), 4.54 (d, J = 2.9 Hz, 2H), 4.03 (dp, J = 11.6, 3.7 Hz, 1H), 3.85 (d, J = 15.0 Hz, 1H), 3.68 (s, 1H), 3.61-3.43 (m, 4H), 3.38 (t, J = 8.1 Hz, 3H), 3.18 (dd, J = 14.3, 6.5 Hz, 1H), 3.01-2.87 (m, 4H), 2.78 (t, J = 7.6 Hz, 1H), 2.64-2.55 (m, 2H); LCMS: 474.8 [M + H]$^+$. |
| 53 | 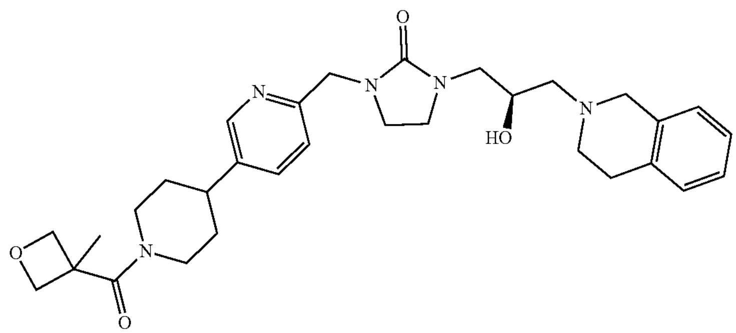 [SMILES: CC1(C(=O)N2CCC(c3ccc(CN4CCN(C[C@H](O)CN5CCc6ccccc6C5)C4=O)nc3)CC2)COC1] | $^1$H NMR (300 MHz, DMSO-d6) δ 8.40 (d, J = 2.3 Hz, 1H), 7.66 (dd, J = 8.2, 2.3 Hz, 1H), 7.17 (d, J = 8.1 Hz, 1H), 7.12-6.97 (m, 4H), 4.85-4.67 (m, 3H), 4.49 (d, J = 13.3 Hz, 1H), 4.37-4.20 (m, 4H), 3.86 (s, 1H), 3.58 (td, J = 6.4, 3.2 Hz, 2H), 3.53-3.38 (m, 2H), 3.29-3.20 (m, 3H), 3.20-3.09 (m, 2H), 3.09-2.96 (m, 2H), 2.82-2.65 (m, 3H), 1.74 (p, J = 3.2 Hz, 1H), 1.54 (s, 4H), 1.41-1.20 (m, 3H), 0.91 (t, J = 7.3 Hz, 3H); LCMS: 548.8 [M + H]$^+$. |
| 54 | 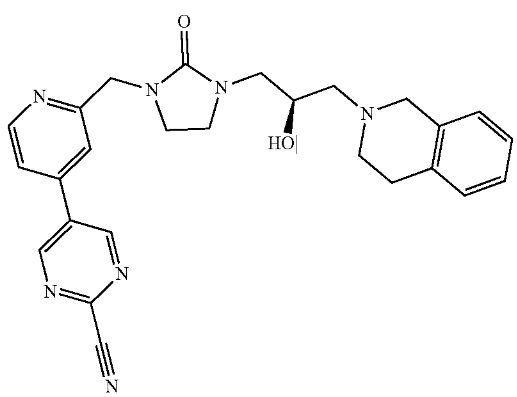 | $^1$H NMR (400 MHz, Methanol-d4) δ 9.32 (s, 2H), 8.69 (dd, J = 5.2, 0.8 Hz, 1H), 7.83-7.74 (m, 2H), 7.18-7.09 (m, 3H), 7.08-7.03 (m, 1H), 4.63-4.52 (m, 2H), 4.13 (tt, J = 7.1, 7.1, 4.5, 4.5 Hz, 1H), 3.87 (s, 2H), 3.63-3.55 (m, 2H), 3.51-3.42 (m, 2H), 3.41-3.33 (m, 1H), 3.26 (dd, J = 14.2, 6.9 Hz, 1H), 2.98 (h, J = 5.3, 5.3, 5.1, 5.1, 5.1 Hz, 4H), 2.81-2.70 (m, 2H); LCMS: 470.8 [M + H]$^+$. |
| 55 | 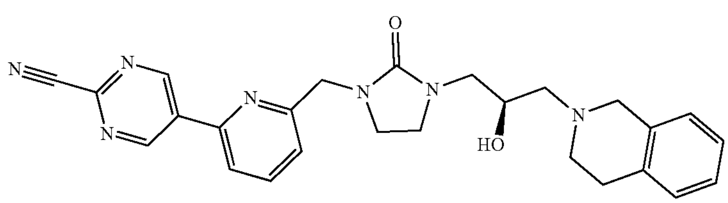 [SMILES: N#Cc1ncc(-c2cccc(CN3CCN(C[C@H](O)CN4CCc5ccccc5C4)C3=O)n2)cn1] | $^1$H NMR (600 MHz, DMSO-d6) δ 9.64-9.56 (m, 2H), 8.14 (dd, J = 7.8, 1.5 Hz, 1H), 7.99 (td, J = 7.9, 7.8, 1.9 Hz, 1H), 7.40 (dd, J = 7.8, 1.5 Hz, 1H), 7.06 (dtt, J = 7.7, 5.4, 5.4, 2.0, 2.0 Hz, 3H), 7.02-6.93 (m, 1H), 4.75-4.69 (m, 1H), 4.50-4.43 (m, 2H), 3.91-3.84 (m, 1H), 3.58 (s, 2H), 3.48 (tdd, J = 8.5, 8.5, 6.6, 1.5 Hz, 1H), 3.45-3.38 (m, 2H), 3.30-3.25 (m, 2H), 3.02 (ddd, J = 13.8, 7.2, 1.6 Hz, 1H), 2.80-2.73 (m, 2H), 2.68 (q, J = 6.2, 5.3, 5.3 Hz, 2H), 2.45-2.38 (m, 2H); LCMS: 470.1 [M + H]$^+$. |
| 56 | 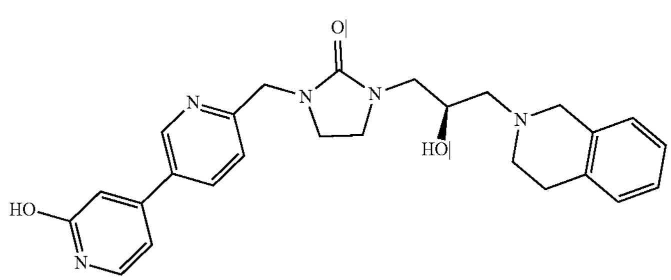 | $^1$H NMR (300 MHz, Chloroform-d) δ 8.77 (dd, J = 2.4, 0.8 Hz, 1H), 7.86 (dd, J = 8.2, 2.4 Hz, 1H), 7.48-7.39 (m, 2H), 7.18-7.07 (m, 4H), 7.04-6.98 (m, 1H), 6.79 (d, J = 1.7 Hz, 1H), 6.51 (dd, J = 6.9, 1.8 Hz, 1H), 4.58 (d, J = 2.7 Hz, 2H), 4.01 (s, 1H), 3.83 (d, J = 14.9 Hz, 1H), 3.71-3.36 (m, 7H), 3.19 (dd, J = 14.3, 6.6 Hz, 1H), 2.92 (d, J = 3.4 Hz, 2H), 2.76 (d, J = 9.0 Hz, 1H), 2.65-2.50 (m, 2H); LCMS: 460.4 [M + H]$^+$. |

TABLE 2-continued

| Comp. No | Structure | Characterization Data |
|---|---|---|
| 57 | 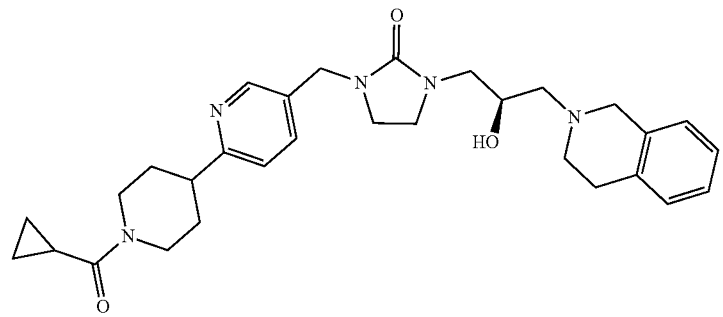 [SMILES: O=C(C1CC1)N1CCC(c2ccc(CN3CCN(C[C@H](O)CN4CCc5ccccc5C4)C3=O)cn2)CC1] | ¹H NMR (400 MHz, DMSO-d6) δ 8.41-8.38 (m, 1H), 7.58 (dd, J = 8.0, 2.3 Hz, 1H), 7.28 (dd, J = 8.0, 0.8 Hz, 1H), 7.10 (d, J = 3.5 Hz, 3H), 7.04 (s, 1H), 4.49 (d, J = 13.1 Hz, 1H), 4.36 (d, J = 13.5 Hz, 1H), 4.25 (s, 2H), 4.12 (q, J = 5.3, 5.3, 5.3 Hz, 1H), 3.87 (s, 1H), 3.66-3.56 (m, 1H), 3.46-3.37 (m, 2H), 3.26 (dd, J = 13.9, 4.2 Hz, 2H), 3.16 (tt, J = 8.4, 8.4, 4.5, 4.5 Hz, 7H), 3.08-2.91 (m, 3H), 2.80 (s, 2H), 2.03-1.94 (m, 2H), 1.93-1.76 (m, 3H), 1.63-1.45 (m, 4H); LCMS: 518.3 [M + H]⁺. |
| 58 | 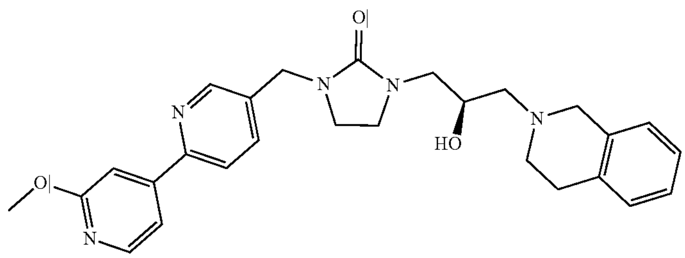 | ¹H NMR (400 MHz, DMSO-d6) δ 8.61 (dd, J = 2.2, 0.8 Hz, 1H), 8.28 (dd, J = 5.4, 0.7 Hz, 1H), 8.08 (dd, J = 8.2, 0.8 Hz, 1H), 7.80 (dd, J = 8.2, 2.3 Hz, 1H), 7.66 (dd, J = 5.4, 1.5 Hz, 1H), 7.46 (dd, J = 1.5, 0.7 Hz, 1H), 7.12-7.05 (m, 3H), 7.05-6.99 (m, 1H), 4.75 (d, J = 4.8 Hz, 1H), 4.36 (s, 2H), 3.90 (m, 4H), 3.60 (s, 2H), 3.49-3.37 (m, 2H), 3.28 (dd, J = 13.8, 4.1 Hz, 1H), 3.25-3.16 (m, 2H), 3.04 (dd, J = 13.9, 7.2 Hz, 1H), 2.79 (t, J = 5.8, 5.8 Hz, 2H), 2.75-2.64 (m, 2H), 2.44 (dd, J = 6.2, 2.7 Hz, 2H); LCMS: 474.1 [M + H]⁺. |
| 59 | 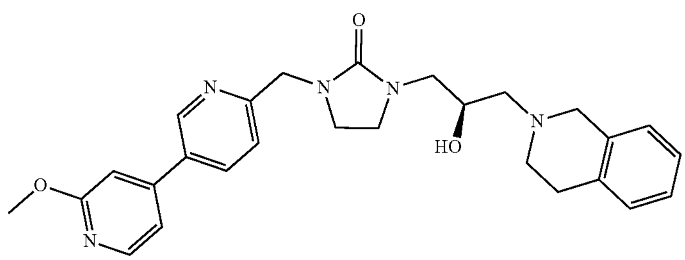 [SMILES: COc1cc(-c2ccc(CN3CCN(C[C@H](O)CN4CCc5ccccc5C4)C3=O)nc2)ccn1] | ¹H NMR (400 MHz, DMSO-d6) δ 8.94 (d, J = 2.3 Hz, 1H), 8.27 (d, J = 5.4 Hz, 1H), 8.18 (dd, J = 8.2, 2.4 Hz, 1H), 7.43-7.34 (m, 2H), 7.21 (d, J = 1.5 Hz, 1H), 7.14-7.06 (m, 3H), 7.06-7.00 (m, 1H), 4.76 (d, J = 4.8 Hz, 1H), 4.42 (s, 2H), 3.90 (s, 4H), 3.61 (s, 2H), 3.53-3.39 (m, 2H), 3.32-3.26 (m, 3H), 3.04 (dd, J = 13.9, 7.3 Hz, 1H), 2.80 (t, J = 5.8, 5.8 Hz, 2H), 2.71 (q, J = 5.7, 5.4, 5.4 Hz, 2H), 2.45 (dd, J = 6.1, 3.5 Hz, 2H); LCMS: 474.3 [M + H]⁺. |
| 60 | 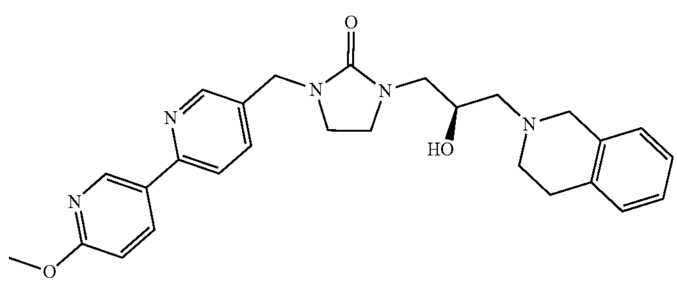 [SMILES: COc1ccc(-c2ccc(CN3CCN(C[C@H](O)CN4CCc5ccccc5C4)C3=O)cn2)cn1] | ¹H NMR (300 MHz, DMSO-d6) δ 8.91-8.84 (m, 1H), 8.54 (d, J = 1.8 Hz, 1H), 8.36 (ddd, J = 8.7, 2.5, 1.4 Hz, 1H), 7.98-7.89 (m, 1H), 7.73 (dt, J = 8.2, 1.8, 1.8 Hz, 1H), 7.15-6.98 (m, 4H), 6.93 (dq, J = 8.7, 0.8, 0.8 Hz, 1H), 4.76 (s, 1H), 4.33 (s, 2H), 3.91 (d, J = 1.4 Hz, 3H), 3.60 (tdd, J = 5.3, 4.3, 3.9, 2.3 Hz, 2H), 3.49-3.39 (m, 3H), 3.27 (td, J = 4.9, 4.1, 1.3 Hz, 1H), 3.18 (t, J = 7.8, 7.8 Hz, 2H), 3.08-2.98 (m, 1H), 2.85-2.67 (m, 4H), 2.45 (d, J = 6.2 Hz, 2H); LCMS: 474.2 [M + H]⁺. |
| 61 | 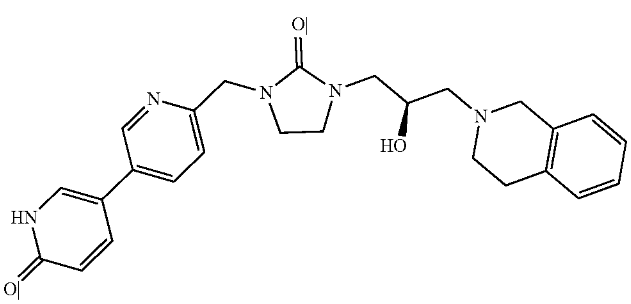 | ¹H NMR (300 MHz, DMSO-d6) δ 11.94 (s, 1H), 8.78-8.69 (m, 1H), 7.98-7.77 (m, 3H), 7.28 (d, J = 8.2 Hz, 1H), 7.16-6.96 (m, 4H), 6.45 (d, J = 9.5 Hz, 1H), 4.75 (d, J = 4.8 Hz, 1H), 4.36 (s, 2H), 3.88 (s, 1H), 3.61 (s, 2H), 3.51-3.38 (m, 2H), 3.32-3.24 (m, 3H), 3.03 (dd, J = 13.8, 7.2 Hz, 1H), 2.79 (d, J = 5.7 Hz, 2H), 2.76-2.66 (m, 2H), 2.43 (t, J = 1.9, 1.9 Hz, 2H); LCMS: 460 [M + H]⁺. |

TABLE 2-continued

| Comp. No | Structure | Characterization Data |
|---|---|---|
| 62 | 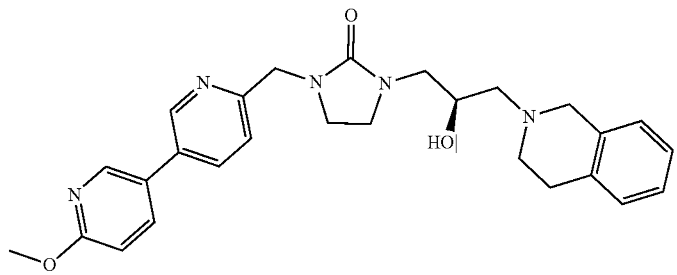 | ¹H NMR (300 MHz, DMSO-d6) δ 8.85-8.80 (m, 1H), 8.54 (dt, J = 2.6, 0.8, 0.8 Hz, 1H), 8.12-8.03 (m, 2H), 7.35 (d, J = 8.1 Hz, 1H), 7.13-6.99 (m, 4H), 6.95 (dt, J = 8.7, 0.8, 0.8 Hz, 1H), 4.76 (d, J = 4.7 Hz, 1H), 4.40 (s, 2H), 3.90 (d, J = 0.7 Hz, 3H), 3.61 (s, 2H), 3.54-3.39 (m, 3H), 3.31-3.24 (m, 3H), 3.03 (dd, J = 13.9, 7.2 Hz, 1H), 2.79 (d, J = 5.8 Hz, 2H), 2.70 (d, J = 7.8 Hz, 2H), 2.47-2.42 (m, 2H); LCMS: 474.4 [M + H]⁺. |
| 63 | 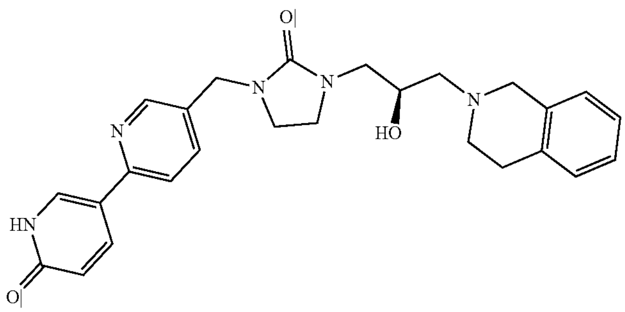 | ¹H NMR (300 MHz, DMSO-d6) δ 11.92 (s, 1H), 8.45 (d, J = 2.2 Hz, 1H), 8.21-8.08 (m, 2H), 7.84-7.76 (m, 1H), 7.65 (dd, J = 8.3, 2.3 Hz, 1H), 7.17-6.97 (m, 4H), 6.44 (dt, J = 9.7, 0.8, 0.8 Hz, 1H), 4.74 (d, J = 4.8 Hz, 1H), 4.29 (s, 2H), 3.86 (d, J = 6.7 Hz, 1H), 3.60 (s, 2H), 3.47-3.38 (m, 2H), 3.32-3.23 (m, 2H), 3.16 (t, J = 7.8, 7.8 Hz, 1H), 3.02 (dd, J = 13.8, 7.1 Hz, 1H), 2.79 (t, J = 5.8, 5.8 Hz, 2H), 2.71 (d, J = 5.1 Hz, 2H), 2.46-2.40 (m, 2H); LCMS: 460.0 [M + H]⁺. |
| 64 | 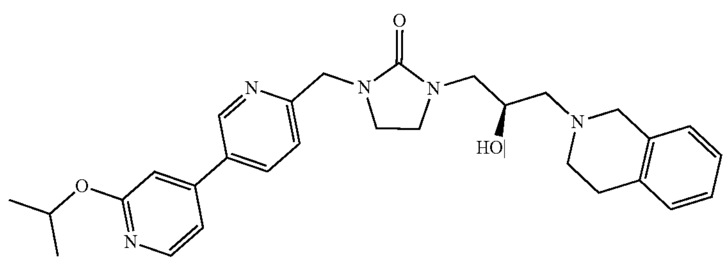 | ¹H NMR (400 MHz, DMSO-d6) δ 8.93 (dd, J = 2.4, 0.8 Hz, 1H), 8.27-8.21 (m, 1H), 8.17 (dd, J = 8.1, 2.4 Hz, 1H), 7.40-7.30 (m, 2H), 7.13-7.07 (m, 4H), 7.05-7.00 (m, 1H), 5.30 (p, J = 6.2, 6.2, 6.2, 6.2 Hz, 1H), 4.76 (d, J = 4.7 Hz, 1H), 4.41 (s, 2H), 3.89 (s, 1H), 3.61 (s, 2H), 3.53-3.38 (m, 2H), 3.28 (s, 2H), 3.04 (dd, J = 13.9, 7.3 Hz, 2H), 2.79 (d, J = 5.8 Hz, 2H), 2.76-2.65 (m, 2H), 2.45 (d, J = 6.0 Hz, 2H), 1.32 (d, J = 6.1 Hz, 6H); LCMS: 502.3 [M + H]⁺. |
| 65 | 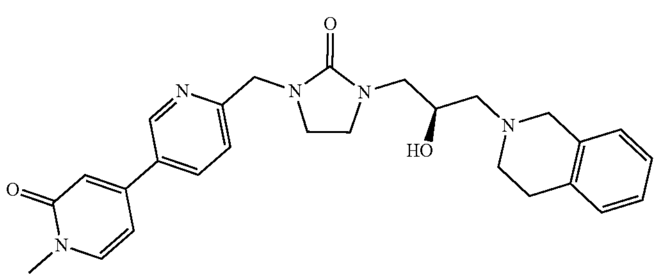 [SMILES: Cn1ccc(-c2ccc(CN3CCN(C[C@H](O)CN4CCc5ccccc5C4)C3=O)nc2)cc1=O] | ¹H NMR (300 MHz, Chloroform-d) δ 8.75 (dd, J = 2.4, 0.8 Hz, 1H), 7.84 (dd, J = 8.1, 2.4 Hz, 1H), 7.46-7.36 (m, 2H), 7.14 (tt, J = 5.2, 5.2, 2.5, 2.5 Hz, 3H), 7.05-6.99 (m, 1H), 6.79 (dd, J = 2.1, 0.5 Hz, 1H), 6.40 (dd, J = 7.0, 2.1 Hz, 1H), 4.56 (d, J = 2.6 Hz, 2H), 4.09-3.98 (m, 1H), 3.87 (d, J = 14.9 Hz, 1H), 3.73-3.62 (m, 1H), 3.60 (s, 3H), 3.59-3.47 (m, 2H), 3.47-3.33 (m, 3H), 3.20 (dd, J = 14.3, 6.4 Hz, 1H), 3.01-2.75 (m, 4H), 2.68-2.57 (m, 2H); LCMS: 474.2 [M + H]⁺. |
| 66 | 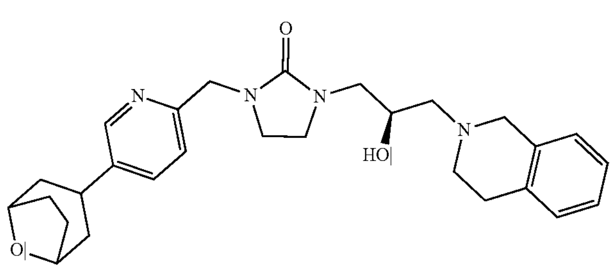 | ¹H NMR (400 MHz, DMSO-d6) δ 8.46 (d, J = 2.3 Hz, 1H), 7.71 (dd, J = 8.1, 2.4 Hz, 1H), 7.18 (dd, J = 8.1, 3.3 Hz, 1H), 7.13-7.06 (m, 3H), 7.03 (dd, J = 6.6, 2.4 Hz, 1H), 4.74 (s, 1H), 4.32 (d, J = 11.5 Hz, 4H), 3.92-3.83 (m, 1H), 3.61 (s, 2H), 3.50-3.37 (m, 2H), 3.31-3.21 (m, 3H), 3.02 (dd, J = 13.9, 7.2 Hz, 1H), 2.93-2.84 (m, 1H), 2.80 (t, J = 5.8, 5.8 Hz, 2H), 2.71 (d, J = 6.3 Hz, 2H), 2.44 (d, J = 5.9 Hz, 2H), 2.24 (dt, J = 14.3, 7.5, 7.5 Hz, 2H), 1.87-1.79 (m, 2H), 1.59 (t, J = 6.6, 6.6 Hz, 2H), 1.50 (ddd, J = 13.6, 9.8, 2.3 Hz, 2H); LCMS: 477.2 [M + H]⁺. |

TABLE 2-continued

| Comp. No | Structure | Characterization Data |
|---|---|---|
| 67 | 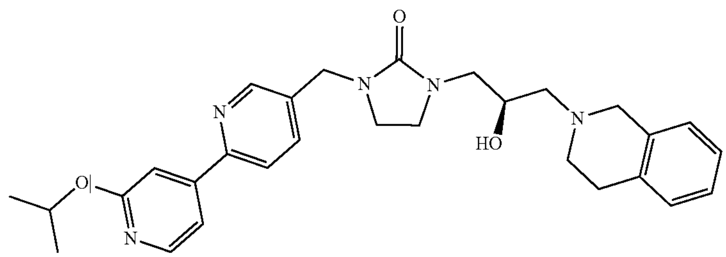 | $^1$H NMR (400 MHz, DMSO-d6) δ 8.60 (dd, J = 2.3, 0.8 Hz, 1H), 8.25 (dd, J = 5.4, 0.7 Hz, 1H), 8.08 (dd, J = 8.2, 0.9 Hz, 1H), 7.78 (dd, J = 8.2, 2.3 Hz, 1H), 7.61 (dd, J = 5.4, 1.5 Hz, 1H), 7.37 (dd, J = 1.5, 0.7 Hz, 1H), 7.12-6.99 (m, 4H), 5.29 (p, J = 6.2, 6.2, 6.2, 6.2 Hz, 1H), 4.75 (d, J = 4.8 Hz, 1H), 4.36 (s, 2H), 3.87 (d, J = 6.5 Hz, 1H), 3.60 (s, 2H), 3.46-3.36 (m, 2H), 3.31-3.16 (m, 3H), 3.04 (dd, J = 13.9, 7.2 Hz, 1H), 2.79 (t, J = 5.8, 5.8 Hz, 2H), 2.70 (q, J = 5.6, 5.2, 5.2 Hz, 2H), 2.44 (dd, J = 6.2, 2.8 Hz, 2H), 1.32 (d, J = 6.2 Hz, 6H); LCMS: 502.2 [M + H]$^+$. |
| 68 | 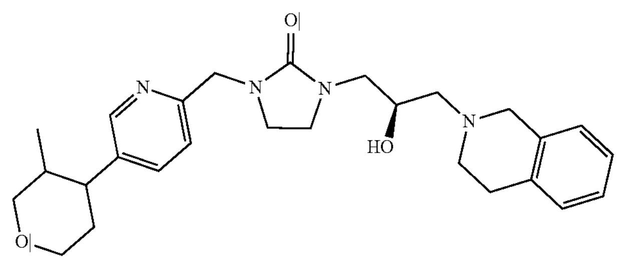 | $^1$H NMR (300 MHz, Chloroform-d) δ 8.38 (d, J = 2.3 Hz, 1H), 7.47 (dd, J = 8.1, 2.4 Hz, 1H), 7.31-7.27 (m, 1H), 7.18-7.08 (m, 3H), 7.04-6.97 (m, 1H), 4.50 (d, J = 2.6 Hz, 2H), 4.19-4.09 (m, 1H), 4.00 (ddt, J = 11.6, 4.8, 3.3, 3.3 Hz, 1H), 3.88-3.70 (m, 3H), 3.67-3.43 (m, 5H), 3.36 (t, J = 8.2, 8.2 Hz, 2H), 3.18 (dd, J = 14.3, 6.5 Hz, 1H), 3.08 (dt, J = 12.8, 3.9, 3.9 Hz, 1H), 2.97-2.86 (m, 3H), 2.79-2.69 (m, 1H), 2.64-2.49 (m, 2H), 2.31-2.13 (m, 2H), 2.00-1.87 (m, 2H), 1.62-1.51 (m, 2H); LCMS: 465.2 [M + H]$^+$. |
| 69 | 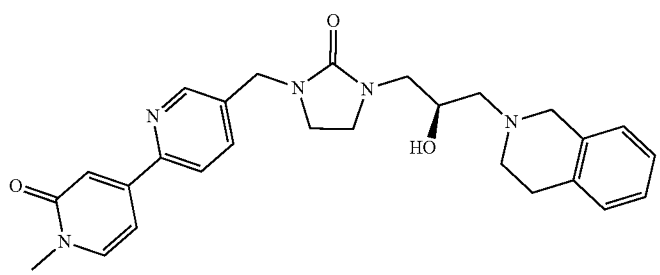 [SMILES: Cn1ccc(-c2ccc(CN3CCN(C[C@H](O)CN4CCc5ccccc5C4)C3=O)cn2)cc1=O] | $^1$H NMR (300 MHz, DMSO-d6) δ 8.62-8.56 (m, 1H), 8.02 (dd, J = 8.1, 0.9 Hz, 1H), 7.82-7.73 (m, 2H), 7.13-6.99 (m, 5H), 6.91 (dt, J = 7.1, 1.6, 1.6 Hz, 1H), 4.75 (d, J = 4.8 Hz, 1H), 4.35 (s, 2H), 3.87 (s, 1H), 3.60 (s, 2H), 3.46 (d, J = 1.1 Hz, 3H), 3.45-3.39 (m, 2H), 3.32-3.24 (m, 3H), 3.23-3.15 (m, 2H), 3.03 (dd, J = 13.9, 7.3 Hz, 1H), 2.79 (d, J = 5.6 Hz, 2H), 2.47-2.39 (m, 2H); LCMS: 474.1 [M + H]$^+$. |
| 70 | Isomer-1 | Isomer-I: $^1$H NMR (300 MHz, Chloroform-d) δ 8.49-8.43 (m, 1H), 7.61 (dd, J = 8.0, 2.4 Hz, 1H), 7.18-7.08 (m, 4H), 7.04-6.99 (m, 1H), 4.38 (t, J = 2.6, 2.6 Hz, 2H), 4.25-4.11 (m, 1H), 3.99 (ddt, J = 9.9, 7.3, 3.9, 3.9 Hz, 1H), 3.90-3.71 (m, 4H), 3.66-3.43 (m, 6H), 3.27-3.11 (m, 4H), 2.96-2.86 (m, 3H), 2.74 (dd, J = 9.9, 5.0 Hz, 1H), 2.65-2.48 (m, 2H), 2.33-2.16 (m, 2H), 1.72-1.61 (m, 2H); LCMS: 465.1 [M + H]$^+$. |
| 71 | Isomer-2 | Isomer-2: $^1$H NMR (300 MHz, Chloroform-d) δ 8.48-8.42 (m, 1H), 7.60 (dd, J = 8.0, 2.3 Hz, 1H), 7.17-7.09 (m, 4H), 7.04-6.99 (m, 1H), 4.38 (d, J = 2.6 Hz, 2H), 4.26-4.16 (m, 1H), 4.03 (ddd, J = 28.5, 11.2, 4.3 Hz, 3H), 3.83 (d, J = 14.9 Hz, 2H), 3.67-3.42 (m, 5H), 3.32-3.08 (m, 4H), 2.97-2.85 (m, 3H), 2.81-2.70 (m, 1H), 2.64-2.47 (m, 3H), 2.19-1.85 (m, 2H), 1.78-1.49 (m, 2H); LCMS: 465.3 [M + H]$^+$. |

TABLE 2-continued

| Comp. No | Structure | Characterization Data |
|---|---|---|
| 72 | 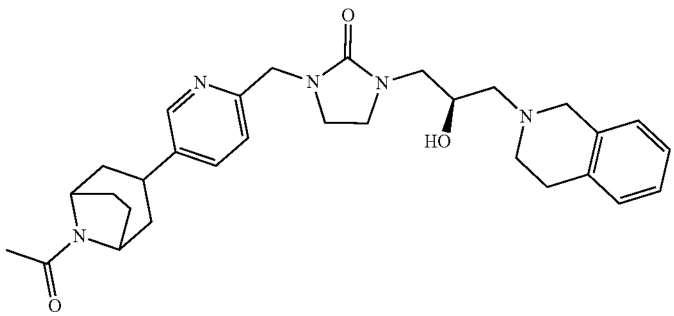 [SMILES: CC(=O)N1C2CCC1CC(c1ccc(CN3CCN(C[C@H](O)CN4CCc5ccccc5C4)C3=O)nc1)C2] | $^1$H NMR (400 MHz, Methanol-d4) δ 8.43-8.38 (m, 1H), 7.71 (dd, J = 8.1, 2.4 Hz, 1H), 7.35-7.30 (m, 1H), 7.14-7.01 (m, 4H), 4.68 (s, 2H), 4.43 (d, J = 2.0 Hz, 2H), 4.36 (s, 2H), 3.75 (s, 2H), 3.61-3.44 (m, 2H), 3.20 (dd, J = 14.2, 7.0 Hz, 2H), 2.90 (d, J = 9.5 Hz, 3H), 2.62 (d, J = 7.3 Hz, 4H), 2.14 (d, J = 6.7 Hz, 3H), 2.06-1.93 (m, 3H), 1.90-1.77 (m, 3H), 4.14-4.03 (m, 3H); LCMS: 518.3 [M + H]$^+$. |
| 73 | 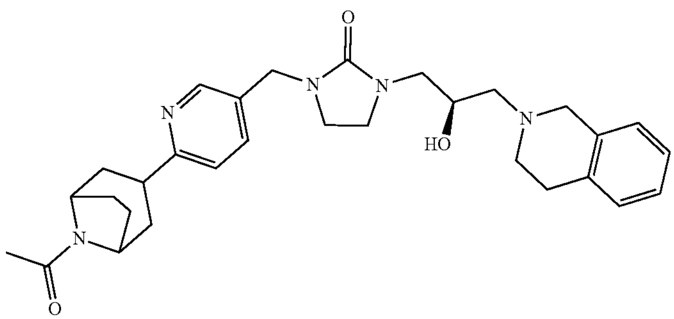 [SMILES: CC(=O)N1C2CCC1CC(c1ccc(CN3CCN(C[C@H](O)CN4CCc5ccccc5C4)C3=O)cn1)C2] | $^1$H NMR (400 MHz, Methanol-d4) δ 8.39 (dd, J = 2.3, 0.8 Hz, 1H), 7.68 (dd, J = 8.0, 2.3 Hz, 1H), 7.32 (dd, J = 8.1, 0.8 Hz, 1H), 7.12-7.06 (m, 3H), 7.02 (dd, J = 7.5, 2.3 Hz, 1H), 4.68 (d, J = 6.2 Hz, 1H), 4.35 (s, 3H), 4.05 (tt, J = 7.0, 7.0, 4.7, 4.7 Hz, 1H), 3.73 (s, 2H), 3.55-3.45 (m, 2H), 3.45-3.35 (m, 2H), 3.27-3.10 (m, 4H), 2.88 (dd, J = 20.3, 5.5 Hz, 4H), 2.59 (dd, J = 6.0, 3.5 Hz, 2H), 2.13 (s, 3H), 2.04-1.74 (m, 7H); LCMS: 518.3 [M + H]$^+$. |
| 74 | 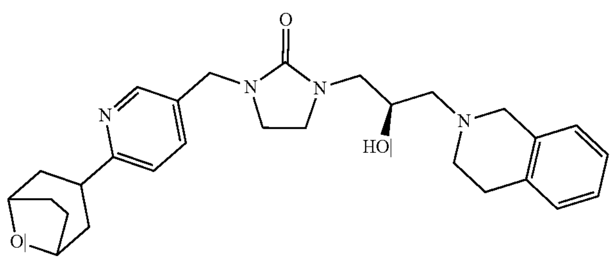 | $^1$H NMR (600 MHz, DMSO-d6) δ 8.37 (d, J = 2.0 Hz, 1H), 7.56 (dt, J = 8.2, 1.9, 1.9 Hz, 1H), 7.43 (d, J = 8.1 Hz, 1H), 7.14-7.00 (m, 4H), 4.74 (dd, J = 4.9, 1.6 Hz, 1H), 4.32-4.24 (m, 4H), 3.86 (h, J = 5.8, 5.8, 5.8, 5.6, 5.6 Hz, 1H), 3.59 (s, 2H), 3.43-3.36 (m, 2H), 3.27 (ddd, J = 13.8, 4.1, 1.6 Hz, 1H), 3.18-3.10 (m, 2H), 3.08-2.98 (m, 2H), 2.79 (t, J = 6.0, 6.0 Hz, 2H), 2.70 (tq, J = 11.3, 11.3, 6.0, 5.3, 5.3 Hz, 2H), 2.43 (pd, J = 6.5, 6.1, 6.1, 6.1, 1.6 Hz, 2H), 2.14 (dddd, J = 18.4, 9.1, 7.3, 4.0 Hz, 4H), 1.63 (qt, J = 7.7, 7.7, 7.3, 4.7, 4.7 Hz, 2H), 1.45 (qd, J = 6.7, 6.7, 6.5, 1.7 Hz, 2H); LCMS: 477.0 [M + H]$^+$. |
| 75 | 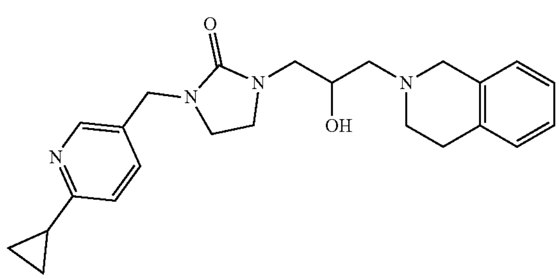 [SMILES: O=C1N(Cc2ccc(C3CC3)nc2)CCN1CC(O)CN1CCc2ccccc2C1] | $^1$H NMR (300 MHz, DMSO-d$_6$) δ: 8.27 (d, 1H), 7.48 (d, 1H), 7.25 (d, 1H), 7.14-6.97 (m, 4H), 4.72 (d, 1H), 4.21 (s, 2H), 3.84 (d, 1H), 3.59 (t, 2H), 3.45-3.37 (m, 1H), 3.33-3.22 (m, 1H), 3.11 (t, 2H), 3.06-2.94 (m, 1H), 2.79 (t, 2H), 2.75-2.66 (m, 2H), 2.42 (d, 2H), 2.08-2.02 (m, 1H), 1.80-1.72 (m, 1H), 1.02-0.77 (m, 4H). LCMS [M + H] + 407.4. |
| 76 | 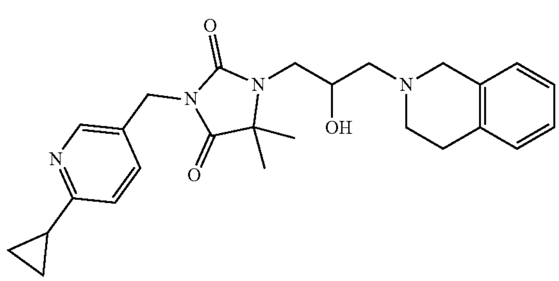 [SMILES: CC1(C)C(=O)N(Cc2ccc(C3CC3)nc2)C(=O)N1CC(O)CN1CCc2ccccc2C1] | 1H NMR (300 MHz, DMSO-d6) δ: 8.32-8.24 (m, 1H), 7.49 (dd, 1H), 7.24 (dd, 1H), 7.15-6.96 (m, 4H), 4.88 (d, 1H), 4.52 (s, 2H), 4.07 (s, 1H), 3.70-3.42 (m, 3H), 3.04 (dd, 1H), 2.83-2.61 (m, 6H), 2.13-1.99 (m, 1H), 1.32 (d, 6H), 0.97-0.78 (m, 4H). LCMS [M + H] +. |

Example-III: Synthesis of 1-((R)-3-(3,4-dihydroiso-quinolin-2(1H)-yl)-2-hydroxypropyl)-3-((5-(tetra-hydro-2H-pyran-3-yl)pyridin-2-yl)methyl)imidazoli-din-2-one Compound-77

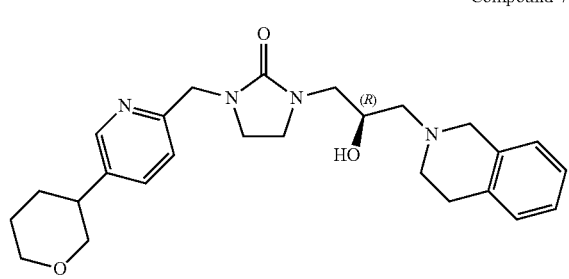

Step-a: Synthesis of 1-((R)-2-((tert-butyldimethylsi-lyl)oxy)-3-(3,4-dihydroisoquinolin-2(1H)-yl)pro-pyl)-3-((5-(tetrahydro-2H-pyran-3-yl)pyridin-2-yl)methyl)imidazolidin-2-one To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (Intermediate-2) (0.4 g, 0.714 mmol), DMA (10 mL), 3-bromotetrahydro-2H-pyran (0.141 g, 0.857 mmol), NiI$_2$ (0.022 g, 0.0714 mmol), Mn powder (0.078 g, 1.429 mmol), MgCl$_2$ (0.068 g, 0.714 mmol), 4,4'-di-ter-butyl-2,2'-bi-pyridyl (0.019 g, 0.0714 mmol), 4-Methyl pyridine (0.066 g, 0.714 mmol) and the reaction mixture was degassed with argon gas for 10 minutes, and reaction mixture was stirred for 16 h at 70° C. After completion of reaction (monitored by TLC, eluent: 5% methanol in DCM), the reaction mixture was diluted with cold water and extracted with ethyl acetate and the combined organics were washed with brine solution, dried over anhydrous sodium sulphate and concentrated under reduced pressure. The obtained residue was purified by column chromatography (SiO$_2$, 1-2% MeOH in DCM) to get (0.02 g, 4.96%) of 1-((R)-2-((tert-butyldimethylsilyl)oxy)-3-(3,4-dihydroisoquinolin-2(1H)-yl)propyl)-3-((5-(tetrahydro-2H-pyran-3-yl)pyridin-2-yl)methyl)imidazolidin-2-one. LCMS: 565.5 [M+H]$^+$.

Step-b: Synthesis of 1-((R)-3-(3,4-dihydroisoquino-lin-2(1H)-yl)-2-hydroxypropyl)-3-((5-(tetrahydro-2H-pyran-3-yl)pyridin-2-yl)methyl)imidazolidin-2-one To a stirred solution of 1-((R)-2-((tert-butyldimethylsilyl)oxy)-3-(3,4-dihydroisoquinolin-2(1H)-yl)propyl)-3-((5-(tetrahydro-2H-pyran-3-yl)pyridin-2-yl)methyl)imidazolidin-2-one (0.02 g, o.0354 mmol) in 10.0 mL of THF was added TBAF (1M solution in THF) (0.07 mL, 0.0798 mmol) at 0° C. and the reaction mixture was stirred for 12 h at RT. After completion of reaction (monitored by TLC, eluent: 5% methanol in DCM), the reaction mixture was concentrated under reduced pressure and obtained residue was diluted with water and extracted with ethyl acetate. The combined extracts were washed with brine solution and dried over anhydrous sodium sulphate concentrated under reduced pressure. The obtained residue was purified by prep purification. method: Column:XBRIDGE C18 [(21.2 mm×500 mm), 5µ]; Mobile phase: (A): 0.1% Ammonia in water; (B): Acetonitrile; Flow: 15 ml/min; Time/% B: 0/25, 2/30, 9/45 to get (0.010 g, 62.89%) of 1-((R)-3-(3,4-dihydroisoquinolin-2(1H)-yl)-2-hydroxypropyl)-3-((5-(tetrahydro-2H-pyran-3-yl)pyridin-2-yl)methyl)imidazolidin-2-one). $^1$H NMR (400 MHz, Methanol-d4) δ 8.41-8.38 (m, 1H), 7.74 (dd, J=8.1, 2.4 Hz, 1H), 7.33 (dd, J=8.0, 0.7 Hz, 1H), 7.11-7.06 (m, 3H), 7.05-7.01 (m, 1H), 4.43 (s, 2H), 4.07 (tt, J=7.3, 4.6 Hz, 1H), 3.98-3.86 (m, 2H), 3.73 (d, J=1.5 Hz, 2H), 3.58-3.43 (m, 4H), 3.38-3.32 (m, 3H), 3.24-3.17 (m, 1H), 2.91 (q, J=5.0 Hz, 4H), 2.87-2.81 (m, 2H), 2.65-2.54 (m, 2H), 2.00 (d, J=2.1 Hz, 1H), 1.87-1.70 (m, 3H); LCMS: 451.4 [M+H]$^+$.

The compounds listed in below Table-3 were prepared by procedure similar to the one described in Example-III with appropriate variations in reactants, quantities of reagents, protections and deprotections, solvents and reaction conditions. The characterization data of the compounds are summarized herein the below table.

TABLE 3

| Comp. No | Structure | Characterization Data |
|---|---|---|
| 78 | (structure shown) | $^1$H NMR (400 MHz, Methanol-d4) δ 8.49-8.45 (m, 1H), 7.99 (dd, J = 8.3, 2.4 Hz, 1H), 7.43 (d, J = 8.3 Hz, 1H), 7.12-7.07 (m, 3H), 7.04-6.99 (m, 1H), 5.10 (dd, J = 8.3, 6.1 Hz, 2H), 4.72 (t, J = 6.3 Hz, 2H), 4.47 (s, 2H), 4.37-4.26 (m, 1H), 4.07 (tt, J = 7.2, 4.5 Hz, 1H), 3.72 (s, 2H), 3.62-3.50 (m, 2H), 3.41-3.32 (m, 2H), 3.26-3.17 (m, 2H), 2.90 (d, J = 5.7 Hz, 2H), |

TABLE 3-continued

| Comp. No | Structure | Characterization Data |
|---|---|---|
| 79 | 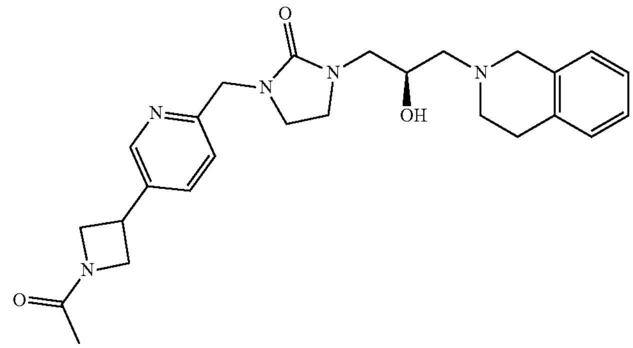 [SMILES: CC(=O)N1CC(c2ccc(CN3CCN(C[C@H](O)CN4CCc5ccccc5C4)C3=O)nc2)C1] | ¹H NMR (400 MHz, Methanol-d4) δ 8.33 (d, J = 2.2 Hz, 1H), 7.77 (dd, J = 8.2, 2.4 Hz, 1H), 7.30-7.26 (m, 1H), 6.99-6.94 (m, 3H), 6.92-6.86 (m, 1H), 4.49 (td, J = 7.9, 7.5, 4.4 Hz, 1H), 4.33 (s, 2H), 4.31-4.24 (m, 1H), 4.12 (dd, J = 8.5, 5.6 Hz, 1H), 3.95 (tt, J = 7.2, 4.5 Hz, 1H), 3.89-3.78 (m, 3H), 3.62 (s, 2H), 3.48-3.38 (m, 2H), 3.26-3.19 (m, 3H), 3.13-3.05 (m, 1H), 2.83-2.70 (m, 4H), 2.56-2.42 (m, 2H), 2.05 (m, 1 H), 1.78 (s, 3H); LCMS: 464.4 [M + H]⁺. |
| 80 | 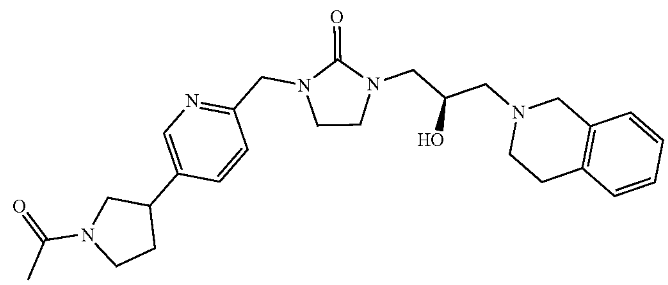 [SMILES: CC(=O)N1CCC(c2ccc(CN3CCN(C[C@H](O)CN4CCc5ccccc5C4)C3=O)nc2)C1] | ¹H NMR (400 MHz, DMSO-d6) δ 8.46 (dd, J = 9.6, 2.4 Hz, 1H), 7.72 (ddd, J = 10.8, 8.1, 2.4 Hz, 1H), 7.23 (dd, J = 8.1, 5.5 Hz, 1H), 7.12-7.06 (m, 3H), 7.05-6.99 (m, 1H), 4.74 (d, J = 4.8 Hz, 1H), 4.33 (d, J = 1.6 Hz, 2H), 3.93-3.80 (m, 2H), 3.65-3.56 (m, 3H), 3.55-3.38 (m, 4H), 3.29-3.22 (m, 2H), 3.21-3.12 (m, 2H), 3.02 (dd, J = 13.8, 7.2 Hz, 1H), 2.80 (t, J = 5.9 Hz, 2H), 2.71 (q, J = 5.4 Hz, 2H), 2.44 (dd, J = 6.1, 3.6 Hz, 1H), 1.96 (d, J = 4.9 Hz, 3H), 1.54 (d, J = 15.4 Hz, 3H); LCMS: 478.4 [M + H]⁺. |

Example-IV: Synthesis of 1-((5-(4-acetylpiperazin-1-yl)pyridin-2-yl)methyl)-3-(3-(8-fluoro-3,4-dihydroisoquinolin-2(1H)-yl)-2-hydroxypropyl)imidazolidin-2-one

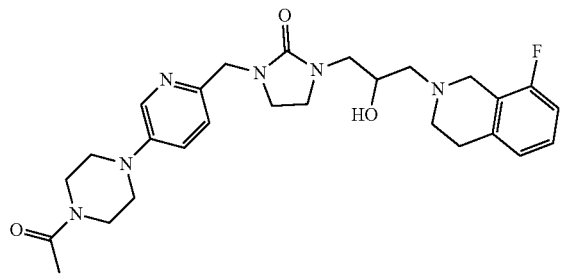

Compound-81

Step-a: Synthesis of tert-butyl (2-(((5-bromopyridin-2-yl)methyl)amino)ethyl)carbamate To a stirred solution of 5-bromopicolinaldehyde (20.0 g, 107.5 mmol) in 500 mL of methanol was added tert-butyl (2-aminoethyl)carbamate (17.22 g, 107.5 mmol) and the reaction mixture was stirred for 30 minutes at RT. The reaction mixture was cooled to 0° C., to this reaction mixture added Na(OAc)₃BH (68.35 g, 322.5 mmol) and stirred for 12 h at RT. After completion of reaction (monitored by TLC, eluent: 5% methanol in DCM), the reaction mixture was concentrated under reduced pressure and obtained residue was diluted with water and extracted with ethyl acetate. The combined organics were washed with brine solution, dried over anhydrous sodium sulphate and concentrated under reduced pressure to get 25.0 g of tert-butyl (2-(((5-bromopyridin-2-yl)methyl)amino)ethyl)carbamate. LCMS: 330.2 [M+]; 332.2 [M+2].

Step-b: Synthesis of 1-((5-bromopyridin-2-yl)methyl)imidazolidin-2-one

To a stirred solution of tert-butyl (2-(((5-bromopyridin-2-yl)methyl)amino)ethyl)carbamate (6.0 g, 18.23 mmol) in 100 mL of THF was added potassium tert-butoxide (4.1 g, 36.46 mmol) and stirred for 2 h at 60° C. temperature. After completion of reaction (monitored by TLC, eluent: 5% methanol in DCM), the reaction mixture was diluted with 5% MeOH in DCM and washed with water, brine solution, dried over anhydrous sodium sulphate and concentrated under reduced pressure. The obtained residue was triturated with ether and dried to get 4.75 g of 1-((5-bromopyridin-2-yl)methyl)imidazolidin-2-one as a yellow coloured solid. LCMS: 256.2 [M+]; 258.2 [M+2].

Step-c: Synthesis of 1-((5-bromopyridin-2-yl)methyl)-3-(oxiran-2-ylmethyl)imidazolidin-2-one To a stirred solution of 1-((5-bromopyridin-2-yl)methyl)imidazolidin-2-one (2.5 g, 9.8 mmol) in 50.0 mL of THF was added NaH (0.6 g, 14.7 mmol) at 0° C. and stirred for 30 minutes at same temperature, to this reaction mixture added epibromohydrin (2.0 g, 14.7 mmol) and allowed to stirred for 12 h at RT. After completion of reaction (monitored by TLC, eluent: 5% Methanol in DCM), the reaction mixture was quenched with water and extracted with ethyl acetate. The combined extracts were washed with water, brine solution, dried over anhydrous sodium sulphate and concentrated under reduced pressure. The obtained residue was purified by column chromatography (SiO$_2$, 3% MeOH in DCM) to get (1.7 g, 55.73%) of 1-((5-bromopyridin-2-yl)methyl)-3-(oxiran-2-ylmethyl)imidazolidin-2-one as a yellow sticky liquid. LCMS:LCMS: 312.2 [M+]; 314.2 [M+2].

Step-d: Synthesis of 1-((5-bromopyridin-2-yl)methyl)-3-(3-(8-fluoro-3,4-dihydroisoquinolin-2(1H)-yl)-2-hydroxypropyl)imidazolidin-2-one To a sealed tube, were added 1-((5-bromopyridin-2-yl)methyl)-3-(oxiran-2-ylmethyl)imidazolidin-2-one (0.5 g, 1.60 mmol), 8-fluoro-1,2,3,4-tetrahydroisoquinoline (0.29 g, 1.92 mmol), DIPEA (0.621 g, 4.81 mmol) and IPA (10 mL), and stirred for 12 h at 100° C. After completion of reaction (monitored by TLC, eluent: 5% methanol in DCM), the reaction mixture was distilled out and the obtained residue was purified by combi-flash column chromatography (SiO$_2$, 2-3% MeOH in DCM) to get (0.1 g, 14.8%) of 1-((5-bromopyridin-2-yl)methyl)-3-(3-(8-fluoro-3,4-dihydroisoquinolin-2(1H)-yl)-2-hydroxypropyl)imidazolidin-2-one. LCMS: 463.3 [M+]; 465.3 [M+2].

Step-e: Synthesis of 1-((5-(4-acetylpiperazin-1-yl)pyridin-2-yl)methyl)-3-(3-(8-fluoro-3,4-dihydroisoquinolin-2(1H)-yl)-2-hydroxypropyl)imidazolidin-2-one To a sealed tube, were added 1-((5-bromopyridin-2-yl)methyl)-3-(3-(8-fluoro-3,4-dihydroisoquinolin-2(1H)-yl)-2-hydroxypropyl)imidazolidin-2-one (0.1 g, 0.216 mmol), Toluene (10 mL), the reaction mixture was degassed with argon gas for 10 minutes. To this reaction were added 1-(piperazin-1-yl)ethan-1-one (0.033 g, 2.59 mmol), Sodium tert-Butoxide (0.031 g, 0.324 mmol), Pd$_2$(dba)$_3$ (0.004 g, 0.0043 mmol) and BINAP (0.008 g, 0.013 mmol) and stirred for 12 h at 100° C. temperature. After completion of reaction (monitored by TLC, eluent: 5% methanol in CHCl$_3$), the reaction mixture was filtered through celite bed and filtrate was concentrated under reduced pressure. The obtained residue was purified by preparative TLC plates eluted with 5% MeOH in DCM to get (0.02 g, 17.69%) of 1-((5-(4-acetylpiperazin-1-yl)pyridin-2-yl)methyl)-3-(3-(8-fluoro-3,4-dihydroisoquinolin-2(1H)-yl)-2-hydroxypropyl)imidazolidin-2-one. $^1$H NMR (400 MHz, Methanol-d4) δ 8.18 (d, J=2.9 Hz, 1H), 7.42 (dd, J=8.7, 3.0 Hz, 1H), 7.26 (d, J=8.7 Hz, 1H), 7.18-7.08 (m, 1H), 6.93 (d, J=7.6 Hz, 1H), 6.85 (t, J=9.0 Hz, 1H), 4.37 (s, 2H), 4.06 (t, J=4.5 Hz, 1H), 3.71 (dt, J=15.5, 5.9 Hz, 5H), 3.53 (td, J=7.9, 7.5, 2.9 Hz, 3H), 3.42-3.33 (m, 3H), 3.28-3.12 (m, 5H), 2.92 (d, J=5.9 Hz, 2H), 2.84 (t, J=5.7 Hz, 2H), 2.63 (dd, J=6.1, 3.4 Hz, 2H), 2.14 (s, 3H); LCMS: 511.4 [M+H]$^+$.

The compounds listed in below Table-4 were prepared by procedure similar to the one described in Example-IV with appropriate variations in reactants, quantities of reagents, protections and deprotections, solvents and reaction conditions. The characterization data of the compounds are summarized herein the below table.

TABLE 4

| Comp. No | Structure | Characterization Data |
|---|---|---|
| 82 | 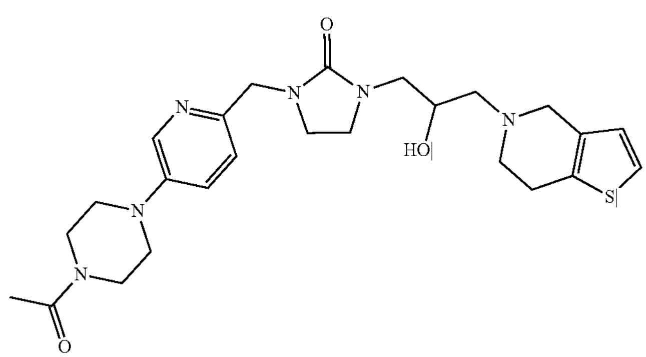 | $^1$H NMR (600 MHz, DMSO-d6) δ 8.25-8.21 (m, 1H), 7.34 (dt, J = 9.0, 2.2 Hz, 1H), 7.26 (dd, J = 5.2, 1.5 Hz, 1H), 7.11 (dd, J = 8.6, 1.5 Hz, 1H), 6.78 (dd, J = 5.2, 1.5 Hz, 1H), 4.74 (d, J = 4.5 Hz, 1H), 4.24 (d, J = 1.5 Hz, 2H), 3.87-3.80 (m, 1H), 3.57 (dq, J = 10.9, 7.2, 5.3 Hz, 4H), 3.52 (s, 2H), 3.44-3.40 (m, 2H), 3.28- 3.24 (m, 1H), 3.22-3.17 (m, 4H), 3.15-3.11 (m, 2H), 3.00 (ddd, J = 13.9, 7.2, 1.5 Hz, 1H), 2.80-2.72 (m, 4H), 2.48-2.44 (m, 2H), 2.03 (d, J = 1.5 Hz, 3H); LCMS: 499.4 [M + H]$^+$. |
| 83 | 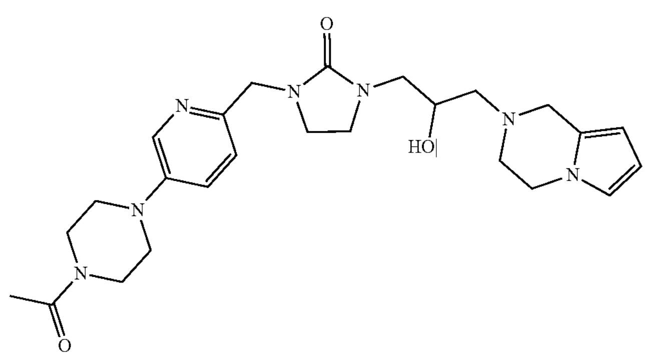 | $^1$H NMR (600 MHz, DMSO-d6) δ 8.23 (d, J = 2.8 Hz, 1H), 7.34 (dt, J = 8.6, 2.0 Hz, 1H), 7.11 (d, J = 8.6 Hz, 1H), 6.57 (dt, J = 2.8, 1.6 Hz, 1H), 5.95 (t, J = 3.0 Hz, 1H), 5.68 (dd, J = 3.3, 1.7 Hz, 1H), 4.78 (s, 1H), 4.25 (s, 2H), 3.89 (td, J = 5.6, 2.1 Hz, 2H), 3.83 (q, J = 6.2 Hz, 1H), 3.63-3.54 (m, 6H), 3.41 (q, J = 8.5, 7.4 Hz, 2H), 3.27-3.17 (m, 5H), 3.12 (t, J = 5.1 Hz, 2H), 3.04-2.97 (m, 1H), 2.81 (q, J = 5.2 Hz, 2H), 2.42 (td, J = 12.6, 11.6, 5.9 Hz, 2H), 2.04 (d, J = 1.4 Hz, 3H); LCMS: 482.4 [M + H]$^+$. |

TABLE 4-continued

| Comp. No | Structure | Characterization Data |
|---|---|---|
| 84 | 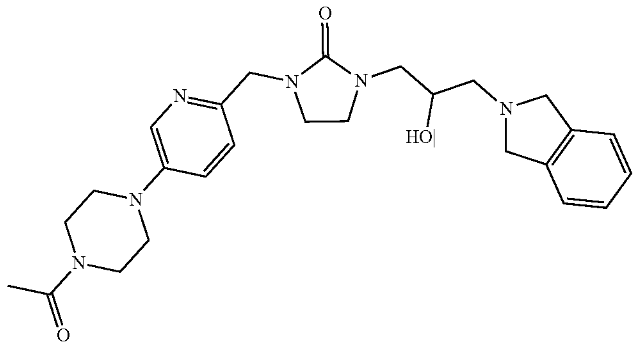 | ¹H NMR (600 MHz, DMSO-d6) δ 8.23 (d, J = 2.9 Hz, 1H), 7.34 (ddd, J = 8.7, 3.0, 1.2 Hz, 1H), 7.22 (ddt, J = 7.3, 5.0, 2.5 Hz, 2H), 7.20-7.15 (m, 2H), 7.12 (d, J = 8.6 Hz, 1H), 4.82 (d, J = 4.4 Hz, 1H), 4.57 (s, 1H), 4.26 (s, 2H), 3.93-3.85 (m, 4H), 3.81-3.76 (m, 1H), 3.57 (dd, J = 6.1, 3.6 Hz, 4H), 3.47-3.41 (m, 1H), 3.33-3.29 (m, 1H), 3.24-3.16 (m, 4H), 3.13-3.10 (m, 2H), 3.00 (ddd, J = 13.8, 7.4, 1.2 Hz, 1H), 2.70-2.60 (m, 2H), 2.11 (d, J = 1.1 Hz, 1H), 2.04 (d, J = 1.2 Hz, 3H); LCMS: 479.4 [M + H]⁺. |
| 85 | 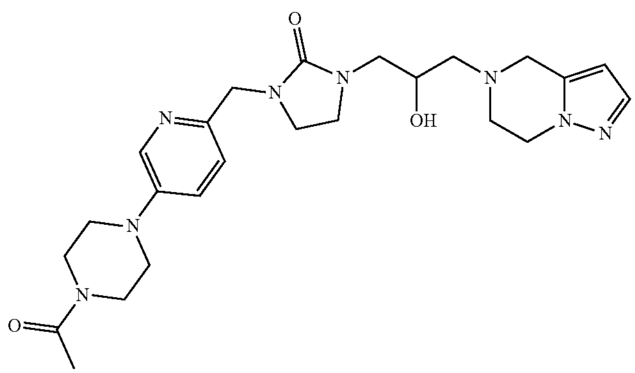 [SMILES: CC(=O)N1CCN(c2ccc(CN3CCN(CC(O)CN4CCn5nccc5C4)C3=O)nc2)CC1] | ¹H NMR (400 MHz, Methanol-d4) δ 8.19 (d, J = 2.9 Hz, 1H), 7.47-7.40 (m, 2H), 7.26 (d, J = 8.6 Hz, 1H), 6.04 (dd, J = 1.9, 0.9 Hz, 1H), 4.37 (s, 2H), 4.21-4.11 (m, 2H), 4.07-3.97 (m, 1H), 3.80 (d, J = 3.4 Hz, 2H), 3.72 (dq, J = 15.5, 5.3, 5.1, 5.1 Hz, 5H), 3.52 (td, J = 7.9, 7.4, 2.9 Hz, 2H), 3.41-3.31 (m, 2H), 3.28-3.17 (m, 5H), 3.10-3.03 (m, 2H), 2.67-2.58 (m, 2H), 2.14 (s, 3H); LCMS: 483.5 [M + H]⁺. |
| 86 | 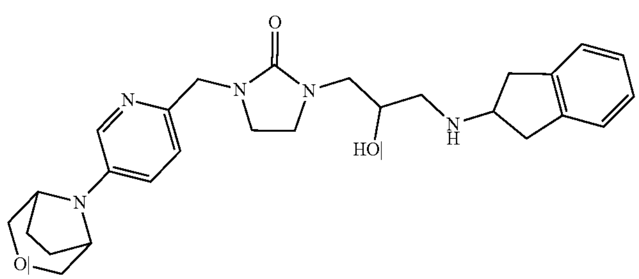 | ¹H NMR (400 MHz, Methanol-d4) δ 8.07 (dd, J = 2.8, 0.7 Hz, 1H), 7.28 (dd, J = 8.7, 2.9 Hz, 1H), 7.22 (dd, J = 8.6, 0.7 Hz, 1H), 7.17 (dd, J = 5.4, 3.3 Hz, 2H), 7.13-7.05 (m, 2H), 4.35 (s, 2H), 4.18-4.12 (m, 2H), 3.90 (ddt, J = 8.8, 6.8, 5.0, 5.0 Hz, 1H), 3.81 (d, J = 10.9 Hz, 2H), 3.61 (p, J = 7.1, 7.1, 7.1, 7.1 Hz, 1H), 3.57-3.44 (m, 4H), 3.40-3.31 (m, 2H), 3.29-3.24 (m, 2H), 3.18 (dt, J = 15.8, 6.9, 6.9 Hz, 2H), 2.83-2.73 (m, 3H), 2.65 (dd, J = 12.1, 8.2 Hz, 1H), 2.09-1.93 (m, 4H), 1.48-1.29 (m, 2H); LCMS: 478.8 [M + H]⁺. |
| 87 | 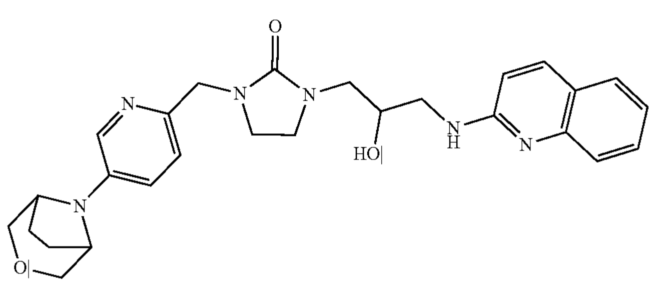 | ¹H NMR (400 MHz, Methanol-d4) δ 8.06 (d, J = 2.6 Hz, 1H), 7.86 (d, J = 8.9 Hz, 1H), 7.62-7.46 (m, 3H), 7.28-7.15 (m, 3H), 6.80 (d, J = 9.0 Hz, 1H), 4.36 (s, 2H), 4.15-4.11 (m, 2H), 4.04 (tdd, J = 6.6, 6.6, 5.0, 3.7 Hz, 1H), 3.80 (d, J = 11.0 Hz, 2H), 3.64 (dd, J = 14.1, 3.8 Hz, 1H), 3.59-3.45 (m, 5H), 3.41-3.32 (m, 4H), 2.08-1.90 (m, 4H); LCMS: 489.3 [M + H]⁺. |

Example-V: Synthesis of 1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one (Compound-88, 89 & 90)

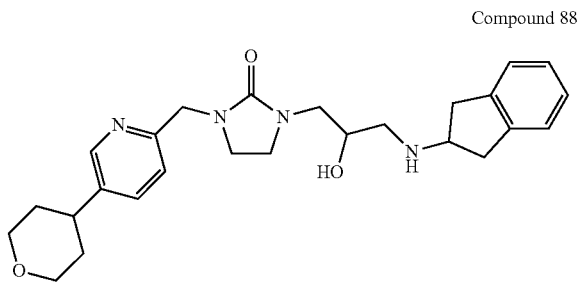 [SMILES: O=C1N(Cc2ccc(C3CCOCC3)cn2)CCN1CC(O)CNC1Cc2ccccc2C1]

Compound 88

Step-a: Synthesis of 1-((5-bromopyridin-2-yl)methyl)-3-(3-((2,3-dihydro-1H-inden-2-yl)amino)-2-hydroxypropyl)imidazolidin-2-one To a sealed tube, were added 1-((5-bromopyridin-2-yl)methyl)-3-(oxiran-2-ylmethyl)imidazolidin-2-one (1.0 g, 3.21 mmol), 2,3-dihydro-1H-inden-2-amine (0.63 g, 4.8 mmol), DIPEA (2.064 g, 16.0 mmol) and IPA (10 mL), and stirred for 12 h at 100° C. After completion of reaction (monitored by TLC, eluent: 5% methanol in DCM), the reaction mixture was distilled out and the obtained residue was purified by combi-flash column chromatography (SiO$_2$, 3% MeOH in DCM) to get (1.4 g, 97.28%) of 1-((5-bromopyridin-2-yl)methyl)-3-(3-((2,3-dihydro-1H-inden-2-yl)amino)-2-hydroxypropyl)imidazolidin-2-one. LCMS: 445.7 7 [M+2]; 447.7 [M+2].

Step-b: Synthesis of 1-(3-((2,3-dihydro-1H-inden-2-yl)amino)-2-hydroxypropyl)-3-((5-(3,6-dihydro-2H-pyran-4-yl)pyridin-2-yl)methyl)imidazolidin-2-one To a 100 mL sealed tube, were added 1-((5-bromopyridin-2-yl)methyl)-3-(3-((2,3-dihydro-1H-inden-2-yl)amino)-2-hydroxypropyl)imidazolidin-2-one (0.5 g, 1.122 mmol), DME/H$_2$O (4:1) (22 mL), the reaction mixture was degassed with argon gas for 10 minutes. To this reaction mixture were added 2-(3,6-dihydro-2H-pyran-4-yl)-4,4,5,5-tetramethyl-1,3,2-dioxaborolane (0.282 g, 1.346 mmol), Sodium carbonate (0.297 g, 2.805 mmol) and Pd(dppf)Cl$_2$ (0.091 g, 0.122 mmol) and stirred for 12 h at 65° C. temperature. After completion of reaction (monitored by TLC, eluent: 5% methanol in DCM), the reaction mixture was filtered through celite bed and filtrate was diluted with water and extracted with ethyl acetate and the combined organics were washed with brine solution, dried over anhydrous sodium sulphate and concentrated under reduced pressure. The obtained residue was purified by column chromatography (SiO$_2$, 1.5% MeOH in DCM) to get (0.3 g, 59.64%) of 1-(3-((2,3-dihydro-1H-inden-2-yl)amino)-2-hydroxypropyl)-3-((5-(3,6-dihydro-2H-pyran-4-yl)pyridin-2-yl)methyl)imidazolidin-2-one. LCMS: 448.8 [M+]; 450.8 [M+2].

Step-c: Synthesis of 1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one A mixture of 1-(3-((2,3-dihydro-1H-inden-2-yl)amino)-2-hydroxypropyl)-3-((5-(3,6-dihydro-2H-pyran-4-yl)pyridin-2-yl)methyl)imidazolidin-2-one (0.3 g, 0.668 mmol) and 10% Pd—C (0.1 g) in 100 mL of ethanol was taken in parr shaker vessel and hydrogenated at 60 psi pressure for 24 h at RT. After completion of reaction (monitored by TLC, eluent: 5% methanol in DCM), the reaction mixture was filtered through celite bed and filtrate was concentrated under reduced pressure. The obtained residue was purified by prep purification method: Column:WATERS XBRIDGE C18 [(150 mm×21.2 mm), 5µ]; Mobile phase: (A): 0.02% Ammonia in water; (B): Acetonitrile; Flow: 15 ml/min; Gradient programme: Time/% B: 0/20, 3/30, 10/60 to get (0.15 g, 50.0%) of 1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one. $^1$H NMR (400 MHz, DMSO-d$_6$) δ 8.42 (d, J=2.2 Hz, 1H), 7.66 (dd, J=8.1, 2.4 Hz, 1H), 7.22-7.13 (m, 3H), 7.13-7.07 (m, 2H), 4.81 (d, J=4.9 Hz, 1H), 4.32 (s, 2H), 3.94 (dt, J=11.1, 3.2 Hz, 2H), 3.68 (d, J=5.9 Hz, 1H), 3.54-3.36 (m, 6H), 3.26 (dd, J=9.0, 6.8 Hz, 2H), 3.20-3.00 (m, 5H), 2.87-2.75 (m, 1H), 2.69-2.55 (m, 3H), 1.73-1.62 (m, 4H); LCMS: 451.9 [M+H]$^+$.

Racemic compound-88 was separated by chiral prep HPLC method to get compound-89 (Isomer-1) and compound-90 (Isomer-2).

Method: Column:CHIRALPAK IA [(250 mm×10.0 mm), 5µ]; Mobile phase: (A): 0.1% DEA in Ethanol; (B): Acetonitrile; Flow: 8 ml/min; Isocratic method: A=50%, B=40%.

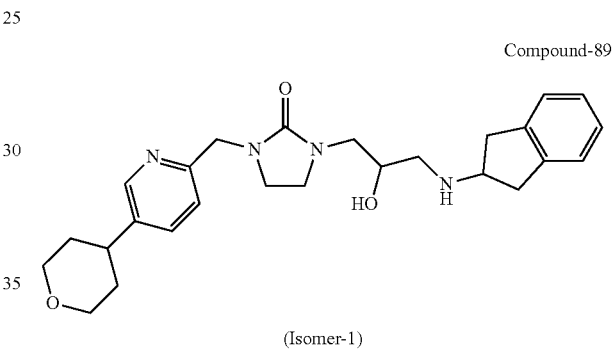

Compound-89

(Isomer-1)

$^1$H NMR (400 MHz, DMSO-d$_6$) δ 8.42 (d, J=2.0 Hz, 1H), 7.66 (dd, J=8.0, 2.4 Hz, 1H), 7.23-7.14 (m, 3H), 7.14-7.08 (m, 2H), 4.87 (s, 1H), 4.32 (s, 2H), 3.94 (dt, J=11.1, 3.1 Hz, 2H), 3.70 (s, 1H), 3.51 (dd, J=9.0, 4.4 Hz, 1H), 3.47-3.37 (m, 4H), 3.31-3.23 (m, 2H), 3.19-3.00 (m, 5H), 2.85-2.75 (m, 1H), 2.71-2.57 (m, 4H), 1.74-1.62 (m, 4H); LCMS: 451.4 [M+H]$^+$.

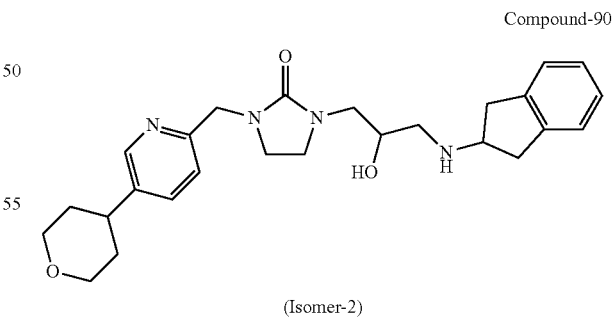

Compound-90

(Isomer-2)

$^1$H NMR (400 MHz, DMSO-d$_6$) δ 8.42 (d, J=2.3 Hz, 1H), 7.66 (dd, J=8.1, 2.4 Hz, 1H), 7.22-7.14 (m, 3H), 7.13-7.06 (m, 2H), 4.87 (s, 1H), 4.32 (s, 2H), 3.94 (dt, J=11.3, 3.1 Hz, 2H), 3.70 (s, 1H), 3.52 (s, 1H), 3.47-3.38 (m, 4H), 3.26 (t, J=8.0 Hz, 3H), 3.19-3.01 (m, 4H), 2.80 (p, J=8.3 Hz, 2H), 2.72-2.59 (m, 3H), 1.67 (h, J=4.1 Hz, 4H); LCMS: 451.2 [M+H]$^+$.

The compounds listed in below Table-5 were prepared by procedure similar to the one described in Example-V with appropriate variations in reactants, quantities of reagents, protections and deprotections, solvents and reaction conditions. The characterization data of the compounds are summarized herein the below table.

TABLE 5

| Comp. No | Structure | Characterization Data |
|---|---|---|
| 91 | 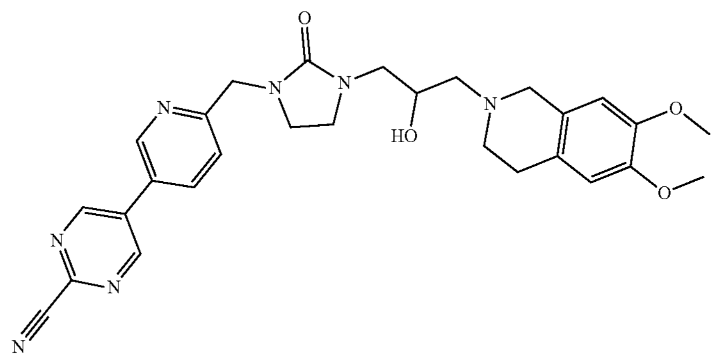 [SMILES: COc1cc2c(cc1OC)CN(CC(O)CN1CCN(Cc3ccc(-c4cnc(C#N)nc4)cn3)C1=O)CC2] | $^1$H NMR (400 MHz, DMSO-d6) δ 9.46 (s, 2H), 9.08-9.03 (m, 1H), 8.34-8.29 (m, 1H), 7.51-7.44 (m, 1H), 6.63 (d, J = 16.6 Hz, 2H), 4.74 (d, J = 4.8 Hz, 1H), 4.45 (s, 2H), 3.93-3.84 (m, 2H), 3.69 (d, J = 4.5 Hz, 5H), 3.51 (d, J = 7.5 Hz, 4H), 3.31-3.25 (m, 2H), 3.09-2.98 (m, 2H), 2.70 (s, 4H), 2.43 (s, 2H); LCMS: 530 [M + H]$^+$. |
| 92 | 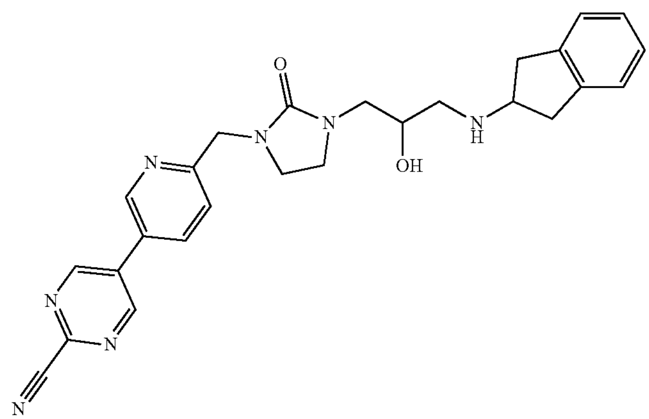 [SMILES: N#Cc1ncc(-c2ccc(CN3CCN(CC(O)CNC4Cc5ccccc5C4)C3=O)nc2)cn1] | $^1$H NMR (400 MHz, Methanol-d4) δ 9.25 (s, 2H), 8.93 (dd, J = 2.4, 0.8 Hz, 1H), 8.23 (dd, J = 8.2, 2.4 Hz, 1H), 7.57 (d, J = 8.3 Hz, 1H), 7.16 (t, J = 4.3 Hz, 2H), 7.13-7.06 (m, 2H), 4.56 (s, 2H), 3.97-3.90 (m, 1H), 3.67-3.51 (m, 3H), 3.46 (dd, J = 9.3, 7.6 Hz, 2H), 3.20 (dq, J = 15.8, 8.3 Hz, 3H), 2.85-2.75 (m, 3H), 2.69 (dd, J = 12.1, 8.1 Hz, 2H); LCMS: 470.8 [M + H]$^+$. |
| 93 | 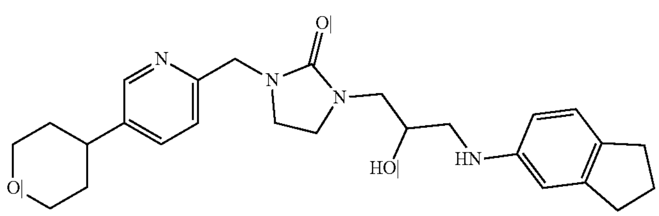 | $^1$H NMR (400 MHz, Methanol-d4) δ 8.38 (d, J = 2.3 Hz, 1H), 7.69 (dd, J = 8.1, 2.3 Hz, 1H), 7.33 (d, J = 8.1 Hz, 1H), 6.96 (d, J = 8.0 Hz, 1H), 6.62-6.58 (m, 1H), 6.49 (dd, J = 8.0, 2.2 Hz, 1H), 4.45 (s, 2H), 4.04 (dt, J = 11.1, 3.1, 3.1 Hz, 2H), 3.97 (p, J = 5.7, 5.7, 5.6, 5.6 Hz, 1H), 3.55 (ddt, J = 16.4, 10.9, 6.1, 6.1 Hz, 4H), 3.41-3.32 (m, 3H), 3.19 (dd, J = 13.0, 5.3 Hz, 1H), 3.09 (dd, J = 13.0, 6.8 Hz, 1H), 2.88 (dq, J = 10.5, 5.7, 5.7, 5.3 Hz, 1H), 2.78 (dt, J = 11.1, 7.4, 7.4 Hz, 4H), 2.01 (p, J = 7.4, 7.4, 7.3, 7.3 Hz, 2H), 1.76 (td, J = 9.9, 8.6, 3.7 Hz, 4H); LCMS: 451.2 [M + H]$^+$. |
| 94 | 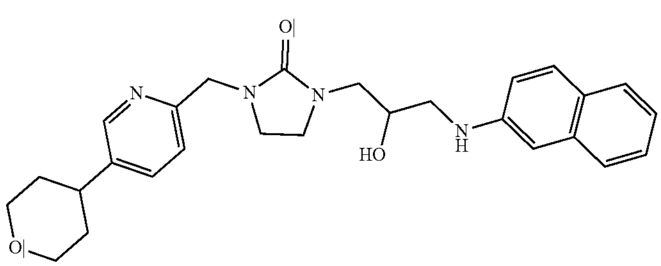 | $^1$H NMR (400 MHz, Methanol-d4) δ 8.36 (d, J = 2.2 Hz, 1H), 7.64-7.54 (m, 4H), 7.34-7.26 (m, 2H), 7.13 (ddd, J = 8.1, 6.8, 1.2 Hz, 1H), 6.98 (dd, J = 8.8, 2.3 Hz, 1H), 6.85 (d, J = 2.3 Hz, 1H), 4.46 (s, 2H), 4.11-3.96 (m, 4H), 3.62-3.47 (m, 4H), 3.42-3.32 (m, 4H), 3.23 (dd, J = 13.1, 6.7 Hz, 1H), 2.80 (td, J = 10.3, 9.9, 4.9 Hz, 1H), 1.77-1.65 (m, 4H); LCMS: 461.8 [M + H]$^+$. |

Example-VI: Synthesis of (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic acid

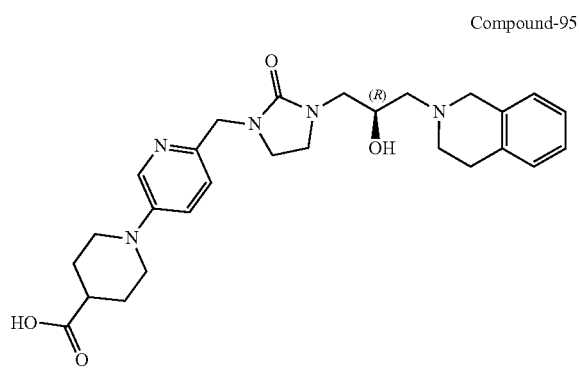

Compound-95

Step-a: Synthesis of (R)-1-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-4-carbonitrile To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (Intermediate-2) (1.0 g, 1.786 mmol), Toluene (30 mL), the reaction mixture was degassed with argon gas for 10 minutes. To this reaction mixture were added piperidine-4-carbonitrile (0.23 g, 2.14 mmol), Sodium tert-Butoxide (0.25 g, 2.68 mmol), Pd$_2$(dba)$_3$ (0.032 g, 0.0357 mmol) and BINAP (0.066 g, 0.1072 mmol) and stirred for 12 h at 100° C. temperature. After completion of reaction (monitored by TLC, eluent: 7% methanol in DCM), the reaction mixture was filtered through celite bed and the filtrate was concentrated under reduced pressure. The obtained residue was purified with column chromatography (SiO$_2$, 2% MeOH in DCM) to get (0.6 g, 57.12%) of (R)-1-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-4-carbonitrile. LCMS: 589.5 [M+H]$^+$.

Step-b: Synthesis of (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic To a stirred suspension of (R)-1-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidine-4-carbonitrile (0.1 g, 0.1698 mmol), in 1,4-Di-Oxane (4.0 mL) added 6N HCl and stirred for 12 h at 100° C. temperature. After completion of reaction (monitored by TLC, eluent: 15% methanol in DCM), the reaction mixture was concentrated under reduced pressure. The obtained residue was basified with NaHCO$_3$ solution and washed with ethyl acetate and aqueous layer was acidified with Conc HCl and extracted with 10% MeOH in DCM. The combined organics were washed with water, brine solution, dried over anhydrous sodium sulphate and concentrated under reduced pressure to get (0.008 g, 9.63%) of (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic acid. $^1$H NMR (400 MHz, Methanol-d4) δ 8.15 (s, 1H), 7.39 (dd, J=8.7, 2.5 Hz, 1H), 7.27-7.14 (m, 4H), 7.13-7.08 (m, 1H), 4.36 (s, 2H), 4.18 (t, J=6.6 Hz, 1H), 4.08 (s, 2H), 3.71 (dt, J=12.7, 3.6 Hz, 2H), 2.44-2.32 (m, 2H), 3.53 (td, J=7.8, 2.7 Hz, 2H), 3.28-3.18 (m, 4H), 3.04 (d, J=7.0 Hz, 2H), 2.93 (t, J=5.9 Hz, 2H), 2.88-2.77 (m, 2H), 1.99 (d, J=12.6 Hz, 2H), 1.86-1.71 (m, 2H); LCMS: 494.4 [M+H]$^+$.

Example-VII: Synthesis of (R)-1-((5-(4-(azetidine-1-carbonyl)piperidin-1-yl)pyridin-2-yl)methyl)-3-(3-(3,4-dihydroisoquinolin-2(1H)-yl)-2-hydroxypropyl)imidazolidin-2-one

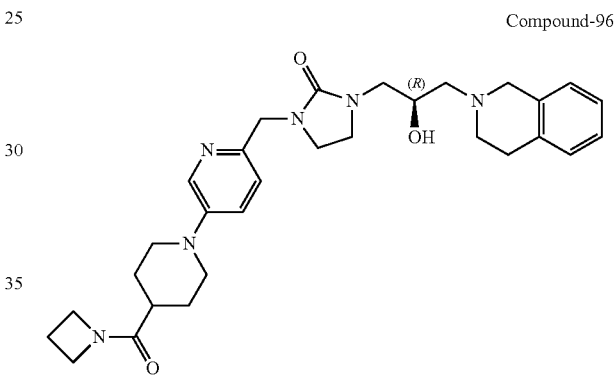

Compound-96

To a stirred solution of (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic acid (0.1 g, 0.202 mmol) in 5 mL of DMF, were added DIPEA (0.078 g, 0.607 mmol), HATU (0.115 g, 0.303 mmol) and azetidine hydrochloride (0.022 g, 0.243 mmol) at 0° C. and stirred for 12 h at RT. After completion of reaction (monitored by TLC, eluent: 10% methanol in DCM), the reaction mixture was diluted with water and extracted with 10% MeOH in DCM. The combined organics were washed with brine solution, dried over anhydrous sodium sulphate and concentrated under reduced pressure. The obtained residue was purified by preparative TLC plates (SiO$_2$, 5% MeOH/DCM) to get (0.012 g, 5.6%) of (R)-1-((5-(4-(azetidine-1-carbonyl)piperidin-1-yl)pyridin-2-yl)methyl)-3-(3-(3,4-dihydroisoquinolin-2(1H)-yl)-2-hydroxypropyl)imidazolidin-2-one. $^1$H NMR (400 MHz, Methanol-d4) δ 8.15 (d, J=2.9 Hz, 1H), 7.39 (dd, J=8.7, 2.9 Hz, 1H), 7.23 (d, J=8.7 Hz, 1H), 7.14-7.06 (m, 3H), 7.03 (dd, J=7.5, 2.4 Hz, 1H), 4.35 (s, 2H), 4.30 (dd, J=8.3, 7.1 Hz, 2H), 4.11-3.97 (m, 3H), 3.82-3.72 (m, 4H), 3.57-3.47 (m, 2H), 3.38-3.32 (m, 2H), 3.22-3.16 (m, 2H), 2.91 (d, J=5.4 Hz, 2H), 2.88-2.76 (m, 4H), 2.63-2.57 (m, 2H), 2.50-2.41 (m, 1H), 2.36-2.26 (m, 2H), 1.78 (h, J=3.7 Hz, 4H); LCMS: 533.6 [M+H]$^+$.

Example-VIII: Synthesis of (R)-1-(6-((3-(3-(3,4-dihydroisoquinolin-2(1H)-yl)-2-hydroxypropyl)-2-oxoimidazolidin-1-yl)methyl)pyridin-3-yl)-N,N-dimethylpiperidine-4-carboxamide Compound-97

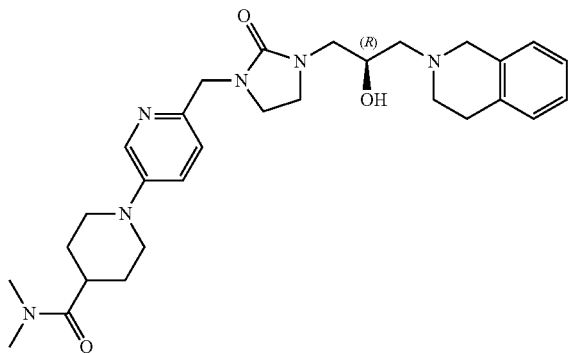

Compound-97 was synthesized by following experimental procedure same as Example-VII. $^1$H NMR (400 MHz, Methanol-d4) δ 8.17-8.14 (m, 1H), 7.40 (dd, J=8.7, 3.0 Hz, 1H), 7.23 (d, J=8.7 Hz, 1H), 7.12-7.06 (m, 3H), 7.03 (dd, J=5.5, 2.6 Hz, 1H), 4.36 (s, 2H), 4.13-4.02 (m, 1H), 3.79 (d, J=12.5 Hz, 2H), 3.71 (s, 2H), 3.60-3.45 (m, 3H), 3.42-3.32 (m, 2H), 3.23-3.12 (m, 4H), 2.95-2.79 (m, 10H), 2.63-2.53 (m, 2H), 1.85-1.77 (m, 4H); LCMS: 521.5 [M+H]$^+$.

Example-IX: Synthesis of (R)-1-((5-(1-((1H-1,2,3-triazol-4-yl)methyl)piperidin-4-yl)pyridin-2-yl)methyl)-3-(3-(3,4-dihydroisoquinolin-2(1H)-yl)-2-hydroxypropyl)imidazolidin-2-one Compound-98

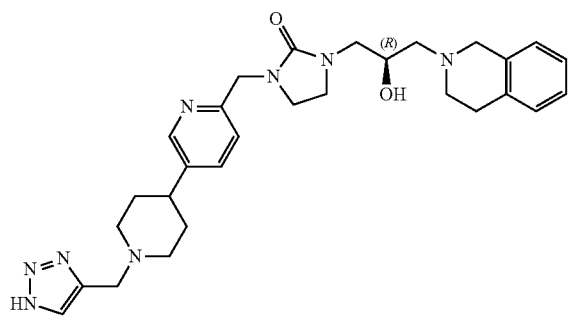

Step-a: Synthesis of (R)-1-(2-((tert-butyldimethylsilyl)oxy)-3-(3,4-dihydroisoquinolin-2(1H)-yl)propyl)-3-((5-(1-(prop-2-yn-1-yl)piperidin-4-yl)pyridin-2-yl)methyl)imidazolidin-2-one To a stirred solution of (R)-1-(2-((tert-butyldimethylsilyl)oxy)-3-(3,4-dihydro-isoquinolin-2(1H)-yl)propyl)-3-((5-(piperidin-4-yl)pyridin-2-yl)methyl)imidazolidin-2-one (Intermediate-4) (0.25 g, 0.44 mmol) in 10 mL of acetone was added potassium carbonate (0.061 g, 0.443 mmol) and propargyl bromide (0.052 g, 0.443 mmol) and stirred for 12 h at RT. After completion of reaction (monitored by TLC, eluent: 5% methanol in DCM), the reaction mixture was concentrated under reduced pressure. The obtained residue was purified by preparative TLC plates (SiO$_2$, 2% MeOH in DCM) to get (0.2 g, 75.18%) of (R)-1-(2-((tert-butyldimethylsilyl)oxy)-3-(3,4-dihydroisoquinolin-2(1H)-yl)propyl)-3-((5-(1-(prop-2-yn-1-yl)piperidin-4-yl)pyridin-2-yl)methyl)imidazolidin-2-one. LCMS: 602.6 [M+H]$^+$.

Step-b: Synthesis of (R)-1-((5-(1-((1H-1,2,3-triazol-4-yl)methyl)piperidin-4-yl)pyridin-2-yl)methyl)-3-(2-((tert-butyldimethylsilyl)oxy)-3-(3,4-dihydroisoquinolin-2(1H)-yl)propyl)imidazolidin-2-one To a stirred solution of (R)-1-(2-((tert-butyldimethylsilyl)oxy)-3-(3,4-dihydroisoquinolin-2(1H)-yl)propyl)-3-((5-(1-(prop-2-yn-1-yl)piperidin-4-yl)pyridin-2-yl)methyl)imidazolidin-2-one (0.12 g, 0.199 mmol) in 10 mL of DMF: MeOH (1:1) were added Trimethyl silyl azide (0.114 g, 0.998 mmol) DIPEA (0.077 g, 0.599 mmol) and CuI (0.0036, 0.018 mmol) and stirred for 12 h at 100° C. temperature. After completion of reaction (monitored by TLC, eluent: 10% methanol in DCM), the reaction mixture was concentrated under reduced pressure. The obtained residue was purified by column chromatography (SiO$_2$, 10% MeOH in DCM) to get (0.07 g, 54.68%) of (R)-1-((5-(1-41H-1,2,3-triazol-4-yl)methyl)piperidin-4-yl)pyridin-2-yl)methyl)-3-(2-((tert-butyldimethylsilyl)-oxy)-3-(3,4-dihydroisoquinolin-2(1H)-yl)propyl)imidazolidin-2-one. LCMS: 645.6 [M+H]$^+$.

Step-c: Synthesis of (R)-1-((5-(1-((1H-1,2,3-triazol-4-yl)methyl)piperidin-4-yl)pyridin-2-yl)methyl)-3-(3-(3,4-dihydroisoquinolin-2(1H)-yl)-2-hydroxypropyl)imidazolidin-2-one To a stirred solution of (R)-1-((5-(1-((1H-1,2,3-triazol-4-yl)methyl)piperidin-4-yl)pyridin-2-yl)methyl)-3-(2-((tert-butyldimethylsilyloxy)-3-(3,4-dihydroisoquinolin-2 (1H)-yl)propyl)imidazolidin-2-one (0.07 g, 0.108 mmol) in 10.0 mL of THF was added TBAF (1M solution in THF) (0.35 mL, 0.325 mmol) at 0° C. and stirred for 12 h at RT. After completion of reaction (monitored by TLC, eluent: 10% methanol in DCM), the reaction mixture was concentrated under reduced pressure and obtained residue was purified by prep purification. Method: Column:KINTEX EVO C18 [(21.2 mm×500 mm), 5µ]; Mobile phase: (A): 0.02% Ammonia in water; (B): Acetonitrile; Flow: 18 ml/min; Time/% B: 0/10, 2/15, 10/40 to get (0.02 g, 35.08%) of (R)-1-((5-(1-((1H-1,2,3-triazol-4-yl)methyl)piperidin-4-yl)pyridin-2-yl)methyl)-3-(3-(3,4-dihydroisoquinolin-2(1H)-yl)-2-hydroxypropyl) imidazolidin-2-one. $^1$H NMR (400 MHz, Methanol-d4) δ 8.42 (s, 1H), 8.04 (s, 1H), 7.74 (d, J=8.0 Hz, 1H), 7.41-7.24 (m, 4H), 7.20 (d, J=6.6 Hz, 1H), 4.54 (s, 2H), 4.46 (d, J=1.5 Hz, 2H), 4.33 (dq, J=9.6, 4.9 Hz, 1H), 3.69 (d, J=12.1 Hz, 2H), 3.56 (ddd, J=29.8, 8.8, 7.5 Hz, 2H), 3.39 (t, J=8.4 Hz, 2H), 3.27-3.18 (m, 5H), 2.99 (d, J=10.0 Hz, 1H), 2.19-2.08 (m, 2H), 1.99 (s, 2H), 1.65 (ddd, J=11.9, 10.0, 6.2 Hz, 4H), 1.41 (h, J=7.4 Hz, 3H); LCMS: 531.5 [M+H]$^+$.

Example-X: Synthesis of (R)-1-((5-(1-((2H-tetrazol-5-yl)methyl)piperidin-4-yl)pyridin-2-yl)methyl)-3-(3-(3,4-dihydroisoquinolin-2(1H)-yl)-2-hydroxypropyl)imidazolidin-2-one

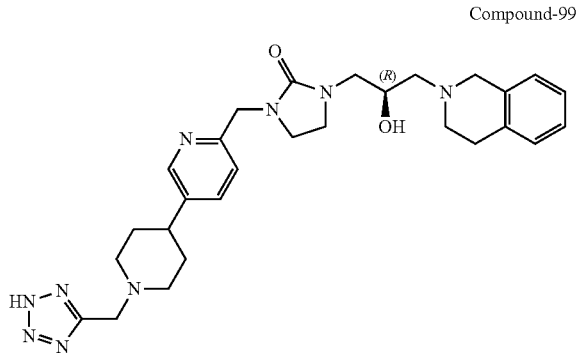

Compound-99

Step-a: Synthesis of (R)-2-(4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidin-1-yl)acetonitrile To a stirred solution of (R)-1-(2-((tert-butyldimethylsilyl)oxy)-3-(3,4-dihydroisoquinolin-2(1H)-yl)propyl)-3-((5-(piperidin-4-yl)pyridin-2-yl)methyl)imidazolidin-2-one (Intermediate-4) (0.4 g, 0.709 mmol) in 10 mL of acetonitrile were added potassium carbonate (0.061 g, 0.443 mmol) and 2-chloroacetonitrile (0.064 g, 0.851 mmol) 0° C. and stirred for 12 h at RT. After completion of reaction (monitored by TLC, eluent: 5% methanol in DCM), the reaction mixture was diluted with water and extracted with ethyl acetate and combined organics were washed with brine solution, dried over anhydrous sodium sulphate and concentrated under reduced pressure. The obtained residue was purified by column chromatography (SiO$_2$, 4% MeOH in DCM) to get (0.32 g, 70.25%) of (R)-2-(4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidin-1-yl)acetonitrile. LCMS: 603.5 [M+H]$^+$.

Step-b: Synthesis of (R)-2-(4-(6-((3-(3-(3,4-dihydroisoquinolin-2(1H)-yl)-2-hydroxypropyl)-2-oxoimidazolidin-1-yl)methyl)pyridin-3-yl)piperidin-1-yl)acetonitrile To a stirred solution of (R)-2-(4-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)piperidin-1-yl)acetonitrile (0.32 g, 0.53 mmol) in 15.0 mL of THF was added TBAF (1M solution in THF) (1.6 mL, 1.592 mmol) at 0° C. and stirred for 12 h at RT. After completion of reaction (monitored by TLC, eluent: 10% methanol in DCM), the reaction mixture was concentrated under reduced pressure and obtained residue was purified by column chromatography (SiO$_2$, 3-4% MeOH in DCM) to get (0.21 g, 81.78%) of (R)-2-(4-(6-((3-(3-(3,4-dihydroisoquinolin-2(1H)-yl)-2-hydroxypropyl)-2-oxoimidazolidin-1-yl)methyl)pyridin-3-yl)piperidin-1-yl)acetonitrile. LCMS: 489.6 [M+H]$^+$.

Step-c: Synthesis of (R)-1-((5-(1-((2H-tetrazol-5-yl)methyl)piperidin-4-yl)pyridin-2-yl)methyl)-3-(3-(3,4-dihydroisoquinolin-2(1H)-yl)-2-hydroxypropyl)imidazolidin-2-one To a stirred solution of (R)-1-(2-((tert-butyldimethylsilyl)oxy)-3-(3,4-dihydroisoquinolin-2(1H)-yl)propyl)-3-((5-(1-(prop-2-yn-1-yl)piperidin-4-yl)pyridin-2-yl)methyl)imidazolidin-2-one (0.06 g, 0.122 mmol) in 10 mL of 1,4-Dioxane were added Trimethyl silyl azide (0.141 g, 1.227 mmol) Dibutyl tin oxide (0.015 g, 0.0613 mmol) and stirred for 12 h at 100° C. temperature. After completion of reaction [monitored by TLC, eluent: methanol:n-butanol:DCM (4:1:20)], the reaction mixture was concentrated under reduced pressure. The obtained residue was purified by preparative TLC plates [SiO$_2$, Methanol:n-butanol:DCM (4:1:20)] to get (0.02 g, 31.25%) of (R)-1-((5-(1-((2H-tetrazol-5-yl)methyl)piperidin-4-yl)pyridin-2-yl)methyl)-3-(3-(3,4-dihydroisoquinolin-2(1H)-yl)-2-hydroxypropyl)imidazolidin-2-one as a sticky solid. $^1$H NMR (400 MHz, DMSO-d$_6$) δ 8.40 (d, J=2.2 Hz, 1H), 7.62 (dd, J=8.0, 2.4 Hz, 1H), 7.20 (d, J=8.1 Hz, 1H), 7.13-6.99 (m, 4H), 5.35-5.28 (m, 1H), 4.79 (s, 1H), 4.31 (s, 2H), 4.13 (s, 2H), 3.89 (s, 1H), 3.65 (s, 2H), 3.45 (d, J=8.3 Hz, 2H), 3.25 (t, J=7.6, 7.6 Hz, 5H), 3.02 (dd, J=14.0, 7.2 Hz, 1H), 2.86-2.71 (m, 4H), 2.69-2.63 (m, 3H), 2.35-2.30 (m, 2H), 2.08-1.92 (m, 1H), 1.88-1.69 (m, 3H); LCMS: 532.7 [M+H]$^+$.

Example-XI: Synthesis of (R)-6'-((3-(3-(3,4-dihydroisoquinolin-2(1H)-yl)-2-hydroxypropyl)-2-oxoimidazolidin-1-yl)methyl)-2-oxo-2H-[1,3'-bipyridine]-4-carbonitrile

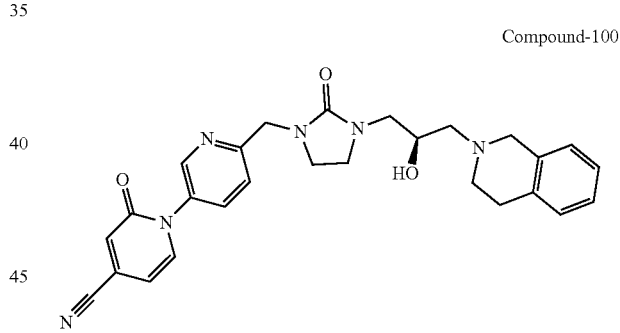

Compound-100

Step-a: Synthesis of (R)-6'-((3-(2-((tert-butyldimethylsilyl)oxy)-3-(3,4-dihydroisoquinolin-2(1H)-yl)propyl)-2-oxoimidazolidin-1-yl)methyl)-2-oxo-2H-[1,3'-bipyridine]-4-carbonitrile To a microwave vial, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (Intermediate-2) (02 g, 0.357 mmol) dmso (5 mL), 2-oxo-1,2-dihydropyridine-4-carbonitrile (0.068 g, 0.536 mmol) CuI (0.07 g, 0.0357 mmol) 1,10-Phenanthroline (0.013 g, 0.071 mmol) and K$_3$PO$_4$ (0.227 g, 1.072 mmol) and the reaction mixture was degassed with argon gas for 10 minutes and stirred for 2 h at 145° C. temperature under microwave irradiation. After completion of reaction (monitored by TLC, eluent: 5% methanol in DCM), the reaction mixture was filtered through celite bed and filtrate was washed with water, brine solution, anhydrous sodium sulphate and concentrated under reduced pressure. The obtained residue was purified by preparative TLC plates (SiO₂, 5% MeOH in DCM) to get 0.04 g of (R)-6'-((3-(2-((tert-butyldimethylsilyl)oxy)-3-(3,4-dihydroisoquinolin-2(1H)-yl)propyl)-2-oxoimidazolidin-1-yl)methyl)-2-oxo-2H-[1,3'-bipyridine]-4-carbonitrile. LCMS: 598.8 [M+H]⁺.

Step-b: Synthesis of (R)-6'-((3-(3-(3,4-dihydroisoquinolin-2(1H)-yl)-2-hydroxypropyl)-2-oxoimidazolidin-1-yl)methyl)-2-oxo-2H-[1,3'-bipyridine]-4-carbonitrile To a stirred solution of (R)-6'-((3-(2-((tert-butyldimethylsilyl)oxy)-3-(3,4-dihydroisoquinolin-2(1H)-yl)propyl)-2-oxoimidazolidin-1-yl)methyl)-2-oxo-2H-[1,3'-bipyridine]-4-carbonitrile (0.04 g, 0.066 mmol) in 2.0 mL of THF was added TBAF (1M solution in THF) (0.2 mL, 0.20 mmol) at 0° C. and stirred for 12 h at RT. After completion of reaction (monitored by TLC, eluent: 10% Methanol in DCM), the reaction mixture was concentrated under reduced pressure and the obtained residue was purified by prep purification. Method: Column:GEMINI NX C18 [(21.2 mm×500 mm), 5µ]; Mobile phase: (A): 0.01% TFA in water; (B): Acetonitrile; Flow: 18 ml/min; Time/% B: 0/10, 2/15, 7/45 to get (0.01 g, 40.0%) of (R)-6'-((3-(3-(3,4-dihydroisoquinolin-2(1H)-yl)-2-hydroxypropyl)-2-oxoimidazolidin-1-yl)methyl)-2-oxo-2H-[1,3'-bipyridine]-4-carbonitrile. ¹H NMR (400 MHz, Chloroform-d) δ 8.54 (dd, J=2.5, 0.7 Hz, 1H), 7.77 (dd, J=8.4, 2.6 Hz, 1H), 7.51 (dd, J=8.4, 0.7 Hz, 1H), 7.44 (dd, J=7.1, 0.8 Hz, 1H), 7.19-7.08 (m, 3H), 7.05-6.98 (m, 2H), 6.42 (dd, J=7.1, 1.8 Hz, 1H), 4.58 (d, J=3.9 Hz, 2H), 4.01 (ddt, J=9.9, 7.2, 3.7, 3.7 Hz, 1H), 3.83 (d, J=14.9 Hz, 1H), 3.68-3.38 (m, 6H), 3.19 (dd, J=14.3, 6.6 Hz, 1H), 2.99-2.88 (m, 3H), 2.75 (dd, J=9.6, 6.2 Hz, 1H), 2.65-2.52 (m, 2H); LCMS: 485.8 [M+H]⁺.

Example-XII: Synthesis of (R)-6'-((3-(3-(3,4-dihydroisoquinolin-2(1H)-yl)-2-hydroxypropyl)-2-oxoimidazolidin-1-yl)methyl)-2H-[1,3'-bipyridin]-2-one Compound-101

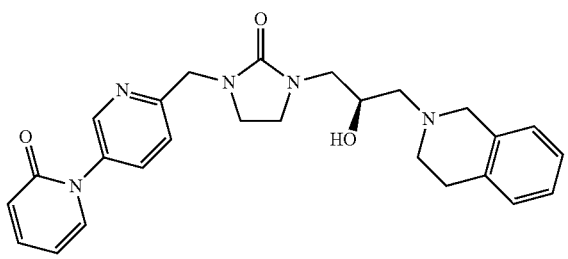

Compound-101 experimental procedure is same as Example-XI. ¹H NMR (300 MHz, Chloroform-d) δ 8.56 (d, J=2.4 Hz, 1H), 7.80 (dd, J=8.4, 2.6 Hz, 1H), 7.51-7.38 (m, 2H), 7.31 (dd, J=6.8, 2.1 Hz, 1H), 7.19-7.07 (m, 3H), 7.07-6.99 (m, 1H), 6.71-6.63 (m, 1H), 6.30 (td, J=6.7, 6.7, 1.4 Hz, 1H), 4.57 (d, J=1.7 Hz, 2H), 4.01 (s, 1H), 3.84 (d, J=14.8 Hz, 1H), 3.69-3.49 (m, 3H), 3.48-3.35 (m, 3H), 3.20 (dd, J=14.3, 6.4 Hz, 1H), 2.92 (d, J=3.3 Hz, 3H), 2.76 (t, J=7.4, 7.4 Hz, 1H), 2.66-2.54 (m, 2H); LCMS: 460.2 [M+H]⁺.

Example-XIII: Synthesis of (R)-1-(3-(3,4-dihydroisoquinolin-2(1H)-yl)-2-hydroxypropyl)-3-((5-(2-(pyrrolidine-1-carbonyl)pyrimidin-5-yl)pyridin-2-yl)methyl)imidazolidin-2-one Compound-102

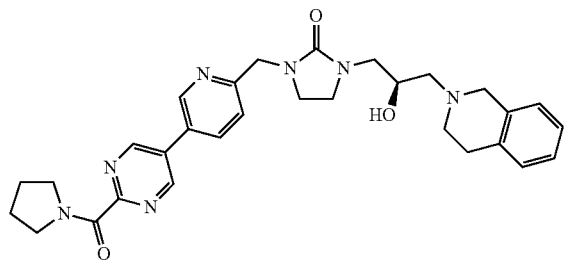

Step-a: Synthesis of (R)-5-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)pyrimidine-2-carbonitrile To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (3.5 g, 6.254 mmol), DME/H₂O (4:1) (70 mL), 5-(4,4,5,5-tetramethyl-1,3,2-dioxaborolan-2-yl)pyrimidine-2-carbonitrile (1.589 g, 6.879 mmol), Sodium carbonate (1.657 g, 15.635 mmol) and Pd(dppf)Cl₂ (0.51 g, 0.625 mmol) and the reaction mixture was degassed with Argon gas for 10 minutes, and stirred for 12 h at 70° C. temperature. After completion of reaction (monitored by TLC, eluent: 5% methanol in DCM), the reaction mixture was filtered through celite bed and filtrate was diluted with water and extracted with ethyl acetate and the combined organics were washed with brine solution, dried over anhydrous sodium sulphate and concentrated under reduced pressure. The obtained residue was purified by column chromatography (SiO₂, 2-3% MeOH in DCM) to get (2.0 g, 54.77%) of (R)-5-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)pyrimidine-2-carbonitrile. LCMS: 281.3 [M+H]⁺.

Step-b: Synthesis of Methyl (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carboxylate To a stirred solution of (R)-5-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)pyrimidine-2-carbonitrile (1.6 g, 2.74 mmol) in (30 mL) methanol was added Methanolic HCl (2M solution) (8.3 mL) at 0° C. and stirred for 12 h at 60° C. temperature. After completion of reaction (monitored by TLC, eluent: 5% methanol in DCM), the reaction mixture was concentrated under reduced pressure. The obtained residue was diluted with water and extracted with ethyl acetate. The combined organics were washed with brine solution, dried over anhydrous sodium sulphate and concentrated under reduced pressure to get 0.65 g of Methyl (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carboxylate. LCMS: 547.2 [M+H]⁺.

Step-c: Synthesis of (R)-5-(6-((3-(3-(3,4-dihydroisoquinolin-2(1H)-yl)-2-hydroxypropyl)-2-oxo-imidazolidin-1-yl)methyl)pyridin-3-yl)pyrimidine-2-carboxylic acid with lithium salt To a stirred solution of methyl (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carboxylate (0.2 g, 0.398 mmol) in THF:H$_2$O (4:1) (10 mL) was added Lithium hydroxide (0.033 g, 0.796 mmol) at 0° C. and stirred for 12 h at RT. After completion of reaction (monitored by TLC, eluent: 5% methanol in DCM), the reaction mixture was concentrated under reduced pressure to get 0.25 g of lithium salt of (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carboxylic acid. LCMS: 547.2 [M+H]$^+$.

Step-d: Synthesis of (R)-1-(3-(3,4-dihydroisoquinolin-2(1H)-yl)-2-hydroxypropyl)-3-((5-(2-(pyrrolidine-1-carbonyl)pyrimidin-5-yl)pyridin-2-yl)methyl)imidazolidin-2-one To a stirred solution of (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carboxylic acid with lithium salt (0.25 g, 0.505 mmol) in 15 mL of DMF, were added DIPEA (0.391 g, 3.032 mmol), HATU (0.288 g, 0.758 mmol) and Pyrrolidine (0.053 g, 0.758 mmol) at 0° C. and stirred for 12 h at RT. After completion of reaction (monitored by TLC, eluent: 5% methanol in DCM), the reaction mixture was diluted with water and extracted with ethyl acetate and the combined organics were washed with brine solution, dried over anhydrous sodium sulphate and concentrated under reduced pressure. The obtained residue was purified by Prep purification. Method: Column:WATERS XBRIDGE C18 [(21.2 mm×150 mm), 5µ]; Mobile phase: (A): 0.02% Ammonia in water; (B): Acetonitrile; Flow: 15 ml/min; Time/% B: 0/10, 3/15, 10/45 to get 0.015 of (R)-1-(3-(3,4-dihydroisoquinolin-2(1H)-yl)-2-hydroxypropyl)-3-((5-(2-(pyrrolidine-1-carbonyl)pyrimidin-5-yl)pyridin-2-yl)methyl)imidazolidin-2-one. $^1$H NMR (400 MHz, Methanol-d4) δ 9.21 (s, 2H), 8.91 (dd, J=2.4, 0.8 Hz, 1H), 8.22 (dd, J=8.2, 2.4 Hz, 1H), 7.56 (dd, J=8.2, 0.8 Hz, 1H), 7.14-7.08 (m, 3H), 7.04 (dd, J=5.0, 2.5 Hz, 1H), 4.56 (s, 2H), 4.10 (tt, J=7.2, 4.5 Hz, 1H), 3.78 (d, J=1.7 Hz, 2H), 3.67 (dd, J=7.4, 6.0 Hz, 2H), 3.64-3.57 (m, 3H), 3.47-3.35 (m, 3H), 3.27-3.16 (m, 2H), 2.98-2.87 (m, 4H), 2.72-2.62 (m, 2H), 2.05-1.93 (m, 4H); LCMS: 542.4 [M+H]$^+$.

Example-XIV: Synthesis of (R)-1-(3-(3,4-dihydroisoquinolin-2(1H)-yl)-2-hydroxypropyl)-3-((6-(2-(pyrrolidine-1-carbonyl)pyrimidin-5-yl)pyridin-3-yl)methyl)imidazolidin-2-one Compound-103

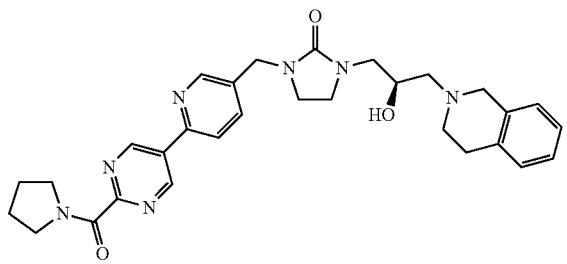

Compound-103 experimental procedure is same as Example-XIII. $^1$H NMR (400 MHz, Methanol-d4) δ 9.49 (s, 2H), 8.69 (d, J=2.2 Hz, 1H), 8.06 (d, J=8.1 Hz, 1H), 7.91 (dd, J=8.2, 2.3 Hz, 1H), 7.14-6.99 (m, 4H), 4.47 (s, 2H), 4.13-4.05 (m, 3H), 3.77 (s, 2H), 3.71-3.52 (m, 5H), 3.39-3.34 (m, 2H), 3.22 (dd, J=14.2, 7.0 Hz, 1H), 2.92 (s, 4H), 2.64 (s, 2H), 2.05-1.93 (m, 4H); LCMS: 542.4 [M+H]$^+$.

Example-XV: Synthesis of (R)-1-(3-(3,4-dihydroisoquinolin-2(1H)-yl)-2-methoxypropyl)-3-((5-(tetrahydro-2H-pyran-4-yl)pyridin-2-yl)methyl)imidazolidin-2-one Compound-104

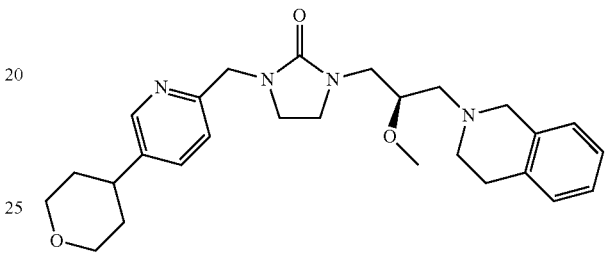

To a stirred solution of (R)-1-(3-(3,4-dihydroisoquinolin-2(1H)-yl)-2-hydroxypropyl)-3-((5-(tetrahydro-2H-pyran-4-yl)pyridin-2-yl)methyl)imidazolidin-2-one (0.03 g, 0.0665 mmol) in 2 mL of THF was added NaH (0.0039 g, 0.0998 mmol) at 0° C. and stirred for 30 min at same temperature, to this reaction mixture added MeI (0.0043 g, 0.0798 mmol) and stirred for 20 h at RT. After completion of reaction (monitored by TLC, eluent: 5% methanol in DCM), the reaction mixture was diluted with water and extracted with ethyl acetate and combined organics were washed with brine solution, dried over anhydrous sodium sulphate and concentrated under reduced pressure. The obtained residue was purified by Preparative TLC plates (SiO$_2$, 5% MeOH in DCM) to get (0.006 g, 19%) of (R)-1-(3-(3,4-dihydroisoquinolin-2(1H)-yl)-2-methoxypropyl)-3-((5-(tetrahydro-2H-pyran-4-yl)pyridin-2-yl)methyl)imidazolidin-2-one. $^1$H NMR (300 MHz, Chloroform-d) δ 8.41 (d, J=2.3 Hz, 1H), 7.51 (dd, J=8.1, 2.4 Hz, 1H), 7.27 (d, J=9.0 Hz, 1H), 7.10 (dd, J=5.9, 3.7 Hz, 3H), 7.05-6.98 (m, 1H), 5.34 (t, J=4.7 Hz, 1H), 4.48 (s, 2H), 4.13-4.01 (m, 2H), 3.70 (s, 2H), 3.68-3.60 (m, 1H), 3.60-3.51 (m, 3H), 3.30 (ddd, J=11.1, 8.9, 5.8 Hz, 4H), 2.89 (d, J=5.8 Hz, 2H), 2.79 (dd, J=10.9, 5.2 Hz, 3H), 2.72-2.57 (m, 2H), 2.22 (t, J=7.6 Hz, 1H), 2.00 (t, J=6.8 Hz, 2H), 1.88-1.72 (m, 5H); LCMS: 465.4 [M+H]$^+$.

PRMT5 Inhibition Based on TR-FRET Assay:

Protein arginine methyltransferase 5 (PRMT5) is a type II arginine methyltransferase that catalyze mono- and symmetric demethylation on arginine residues of histone or non-histone proteins in presence of S-adenosylmethionine (AdoMet or SAM) a cofactor responsible for donating the methyl group. PRMT5 is reported to be overexpressed in several human cancers. To identify compounds that inhibit the PRMT5 and decrease its activity, a TR-FRET based assay has been established. Time-resolved fluorescence resonance energy transfer (TR-FRET) HTS assays are homogeneous proximity assays where the interaction of two dye-labeled binding partners is detected by the energy transfer between a donor and an acceptor dye, and the subsequent light emission by the acceptor dye. PRMT5 catalyzes Histone H4 peptide [1-16] which is biotin tagged to the Lysine amino acid at carboxyl end, in presence of S-adenosyl-1-methionine (SAM) to methylate the peptide. The antibody specific to mono methylated H4 peptide (H4R3) with Ig conjugate binds to the methylated peptide, indirectly binding to the Europium lanthanide. SureLight Allophycocyanin-Streptavidin binds to the biotin tag of the peptide, therefore accepting the energy transferred from the Europium lanthanide. This energy transfer between Europium to SureLight Allophycocyanin is a direct measure of the activity/inhibition of the PRMT5 enzyme.

Reagents and Equipments:

| Reagents/Equipment | Supplier | Catalogue No. |
|---|---|---|
| Bicine | Sigma | B8660 |
| Sodium Chloride | Sigma | S9888 |
| Bovine serum albumin | Sigma | 5470 |
| Tween-20 | Sigma | P1379 |
| DMSO | Rankem | D0178 |
| DL-Dithiothreitol | Sigma | D0632 |
| SGRGKGGKGLGKGGA-K(Biotin) | AnaSpec | SGA-11292-01-QUNNS |
| PRMT5/MEP50 Complex | Reaction Biology | HMT-22-148 |
| S-(5'-Adenosyl)-L-methionine chloride dihydrochloride | Sigma | A7007 |
| Goat polyclonal to Rabbit IgG (Europium) | Abcam | ab187910 |
| Rabbit polyclonal to Histone H4 (mono methyl R3) | Abcam | ab17339 |
| SureLight Allophycocyanin-Streptavidin | Perkin Elmer | CR-130-100 |
| Potassium Fluoride | Sigma | 449148 |
| 384 well Polystyrene F-Bottom Micro plates, White, Med Binding | Greiner | 781075 |
| Victor-3 (Wallac) | Perkin Elmer | — |
| GraphPad Prism 7 | GraphPad Software, Inc. | — |
| Micropipettes | Eppendorf | — |

Assay buffer: 20 mM BICINE (pH 7.6), 25 mM NaCl, 2 mM DTT, 0.01% Tween-20 and 0.01% BSA.

Reagent Preparation:

| Reagent | Stock conc. | Working conc. | Final assay conc. |
|---|---|---|---|
| DMSO | 100% | 7.50% | 1% |
| Histone-H4 Peptide | 5 µM | 250 nM | 50 nM |
| SAM | 300 µM | 3 µM | 1 µM |
| PRMT5:MEP50 complex | 8.7 µM | 96 nM | 32 nM |
| Detection Mix | | | |
| Anti H4R3 Ab. | 6.6 µM | 60 nM | 3 nM |
| Anti IgG Europium | 6.6 µM | 60 nM | 3 nM |
| Streptavidin SAPC | 6.35 µM | 60 nM | 3 nM |
| Potassium Fluoride | 2 M | 2 M | 200 mM |

The compound dilutions were prepared as 7.5% DMSO stock solutions in assay buffer. To 2 µL (7.5×) of test compound, 5 µL of PRMT5 enzyme prepared in assay buffer (Final concentration of 32 nM in 15 µL reaction volume) was added and allowed for 30 minutes pre-incubation time in a white polystyrene 384-well plate at room temperature. A total of 8 µL substrate mix solution containing Biotinylated H4 peptide SGRGKGGKGLGKGGA-K (Biotin, 3 µl) and S-Adenosylmethionine (5 µl) was added to each well to start the reaction at a final concentration of 50 nM and 1 µM respectively. The reactions were incubated for 90 minutes at room temperature and then quenched with 5 µL of detection mixture per well (making final volume of each well is 20 µL solution). The plates were then read on Victor-3 with Excitation at 340 nm and Emissions collected at 615 and 665 nm in TR-FRET protocol.

The following calculations were made:
1. Fold Activity: Signal at F665/F615*10000 of positive control/signal at F665/F615*10000 of substrate control.
2. Percentage inhibition: 100−{signal at F665/F615*1000 of NCE/signal at F665/F615*10000 of positive control}*100.

The percentage inhibition vs. concentration of the test compound was plotted using Graphpad Prism to calculate the $IC_{50}$. For $IC_{50}$ concentrations, 1:3 dilution of compound in 100% DMSO based on potency expected from screening followed by buffer dilution from each concentration. The results are shown in Table-6.

TABLE 6

$IC_{50}$ of compounds of present invention on PRMT5 inhibition

| Compound No. | PRMT5 $IC_{50}$ (µM) |
|---|---|
| 1 | 0.042 |
| 2 | 0.041 |
| 3 | 0.02 |
| 4 | 0.026 |
| 5 | 0.05 |
| 6 | 0.009 |
| 7 | 0.048 |
| 8 | 0.03 |
| 9 | 0.058 |
| 10 | 0.052 |
| 12 | 0.036 |
| 13 | 0.017 |
| 14 | 0.116 |
| 15 | 0.012 |
| 16 | 0.015 |
| 17 | 0.012 |
| 18 | 0.025 |
| 19 | 0.037 |
| 20 | 0.031 |
| 21 | 0.037 |
| 22 | 0.031 |
| 23 | 0.032 |
| 24 | 0.234 |
| 25 | 0.036 |
| 26 | 0.097 |
| 27 | 0.02 |
| 28 | 0.05 |
| 29 | 0.163 |
| 30 | 0.092 |
| 31 | 0.059 |
| 32 | 0.022 |
| 33 | 0.014 |
| 34 | 0.047 |
| 35 | 0.014 |
| 36 | 0.013 |
| 37 | 0.053 |
| 38 | 0.069 |
| 39 | 0.026 |
| 40 | 0.163 |
| 41 | 0.025 |
| 42 | 0.012 |
| 43 | 0.01 |
| 44 | 0.011 |
| 45 | 0.018 |
| 46 | 0.012 |
| 47 | 0.085 |
| 48 | 0.03 |
| 49 | 0.043 |
| 50 | 0.024 |
| 51 | 0.066 |
| 52 | 0.017 |
| 53 | 0.018 |

TABLE 6-continued

IC$_{50}$ of compounds of present invention on PRMT5 inhibition

| Compound No. | PRMT5 IC$_{50}$ (μM) |
|---|---|
| 54 | 0.07 |
| 55 | 0.032 |
| 56 | 0.018 |
| 57 | 0.04 |
| 58 | 0.02 |
| 59 | 0.025 |
| 60 | 0.065 |
| 61 | 0.025 |
| 62 | 0.044 |
| 63 | 0.059 |
| 64 | 0.039 |
| 65 | 0.076 |
| 66 | 0.043 |
| 67 | 0.059 |
| 68 | 0.054 |
| 69 | 0.059 |
| 70 | 0.14 |
| 71 | 0.211 |
| 72 | 0.019 |
| 73 | 0.039 |
| 74 | 0.026 |
| 75 | 0.207 |
| 76 | 0.061 |
| 77 | ND |
| 78 | 0.119 |
| 79 | 0.041 |
| 80 | 0.178 |
| 81 | 0.019 |
| 82 | 0.057 |
| 83 | 0.593 |
| 84 | 0.197 |
| 85 | NI |
| 86 | 0.061 |
| 88 | 0.022 |
| 89 | 0.015 |
| 90 | 0.285 |
| 92 | 0.021 |
| 95 | 0.366 |
| 96 | 0.036 |
| 97 | 0.119 |
| 98 | 0.025 |
| 99 | 0.119 |
| 100 | 0.024 |
| 101 | 0.068 |
| 102 | 0.046 |
| 103 | 0.039 |
| 104 | 0.444 |

Z138 Cell Proliferation Assay:

Z138 cells were seeded in a 96-well round-bottom plate and treated with varying concentration of compound. The final DMSO concentration was maintained at 0.05%. The selected compounds of present invention were screened in a 9-point dose response format starting with 10 μM and 1/3$^{rd}$ serial dilution. On the 4th day, cells were spun down and media was replaced while maintaining the initial compound concentration in each well. At the end of the 7th day, cells were spun down and media was aspirated. 50 4 of XTT containing media was added to the wells. The plates were read using the M3 spectrophotometer at 465 nm. GI$_{50}$ values were calculated by fitting the dose response data to sigmoidal curve fitting equation using GraphPad Prism software V7. The results are shown in Table-7.

The compounds were screened in the above mentioned assay procedures for determining IC$_{50}$ and GI$_{50}$ values in inhibiting PRMT5. The results for selected compounds are summarized in the Table 6 below wherein "A" refers to GI$_{50}$ value lower than 0.1 μM, "B" refers to GI$_{50}$ value between 0.1 μM and 0.3 μM (both inclusive) and "C" refers to GI$_{50}$ value higher than 0.3 μM.

TABLE 7

GI50 of compounds of present invention on PRMT5 inhibition

| Compound No. | Z138 GI$_{50}$ (μM) |
|---|---|
| 1 | A |
| 2 | C |
| 3 | A |
| 4 | B |
| 5 | C |
| 6 | A |
| 7 | C |
| 8 | B |
| 9 | A |
| 10 | B |
| 12 | B |
| 13 | B |
| 14 | C |
| 15 | B |
| 16 | B |
| 17 | B |
| 18 | B |
| 19 | A |
| 20 | A |
| 21 | B |
| 22 | A |
| 23 | A |
| 24 | C |
| 25 | A |
| 26 | B |
| 27 | C |
| 28 | B |
| 29 | B |
| 30 | A |
| 31 | A |
| 32 | A |
| 33 | A |
| 34 | A |
| 35 | A |
| 36 | A |
| 37 | C |
| 38 | A |
| 39 | A |
| 40 | C |
| 41 | A |
| 42 | B |
| 43 | A |
| 44 | A |
| 45 | B |
| 46 | B |
| 47 | B |
| 48 | A |
| 49 | A |
| 50 | A |
| 51 | B |
| 52 | A |
| 53 | A |
| 54 | C |
| 55 | B |
| 56 | A |
| 58 | A |
| 59 | A |
| 60 | B |
| 61 | A |
| 62 | A |
| 63 | B |
| 64 | A |
| 65 | A |
| 66 | A |
| 67 | A |
| 68 | A |
| 69 | B |
| 70 | A |
| 71 | C |
| 72 | A |
| 73 | B |
| 74 | A |
| 77 | B |
| 79 | A |
| 80 | C |
| 82 | C |

TABLE 7-continued

GI50 of compounds of present invention on PRMT5 inhibition

| Compound No. | Z138 GI$_{50}$ (µM) |
| --- | --- |
| 83 | C |
| 84 | C |
| 85 | C |
| 86 | C |
| 89 | B |
| 92 | B |
| 95 | C |
| 96 | A |
| 97 | A |
| 98 | A |
| 99 | C |
| 100 | B |
| 101 | B |
| 102 | A |
| 103 | B |

We claim:

1. A compound of formula (I):

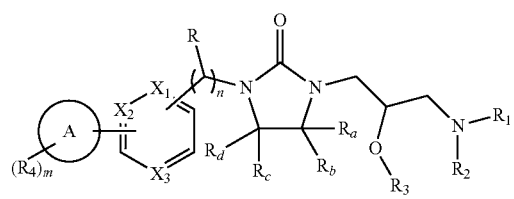

(I)

or a pharmaceutically acceptable salt thereof or a stereoisomer thereof;
wherein, each $X_1$, $X_2$ and $X_3$ are independently $CR_5$ or N;
ring A is cycloalkyl, aryl, heterocycloalkyl or heteroaryl;
R is hydrogen, alkyl or halo;

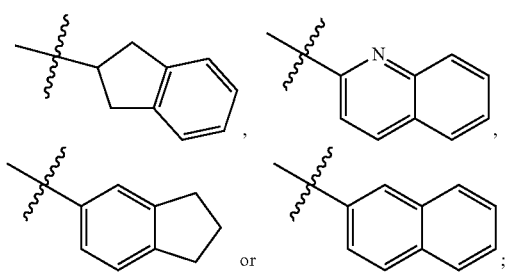

$R_1$ is
$R_2$ is hydrogen or alkyl;
alternatively, $R_1$ and $R_2$ together with the nitrogen to which they are attached form a bicyclic heterocyclyl ring optionally containing 1 to 3 additional heteroatoms selected from N, O and S; wherein the bicyclic heterocyclyl ring is optionally substituted by one or more $R_6$;
$R_3$ is hydrogen or alkyl;
$R_4$ at each occurrence independently is hydrogen, halo, haloalkyl, cyano, alkyl, alkenyl, alkynyl, hydroxy, alkoxy, —C(O)$R_7$, -alkyl-C(O)$R_7$, —S(O)$_2R_7$; wherein the said alkyl, alkenyl and alkynyl are optionally substituted with 1 to 3 groups selected from hydroxyl, halo, heterocycloalkyl and heteroaryl;
alternatively, two $R_4$ on the same atom together form an oxo (=O) group;
$R_5$ at each occurrence independently is hydrogen, alkyl, halo, haloalkyl or alkoxy;

$R_6$ is alkyl, alkoxy, hydroxy, cyano, halo, or haloalkyl;
$R_7$ is alkyl, hydroxy, alkoxy, —$NR_eR_f$, cycloalkyl, aryl, heterocycloalkyl or heteroaryl; wherein each alkyl, cycloalkyl, aryl, heterocycloalkyl and heteroaryl is further optionally substituted by one or more $R_6$;
$R_a$ and $R_b$ each independently are hydrogen or alkyl;
$R_c$ and $R_d$ each independently are hydrogen or alkyl; alternatively $R_c$ and $R_d$ together represent an oxo (=O) group;
$R_e$ and $R_f$ each independently are hydrogen or alkyl; alternatively, $R_e$ and $R_f$ together with the nitrogen to which they are attached form an optionally substituted 3 to 7 membered heterocyclic ring with 1 to 2 additional heteroatoms selected from N, O and S; wherein the optional substituent is one or more $R_6$;
'm' is an integer from 1 to 3; and
'n' is 0 or 1.

2. The compound of claim 1, having a compound of formula (IA):

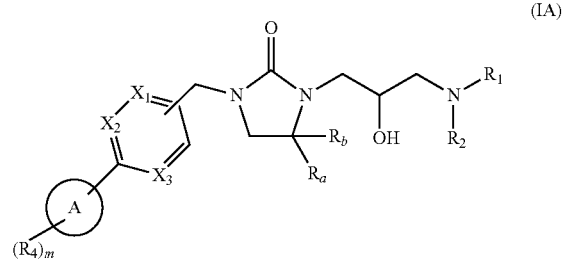

(IA)

or a pharmaceutically acceptable salt thereof or a stereoisomer thereof.

3. The compound of claim 1, having a compound of formula (IB):

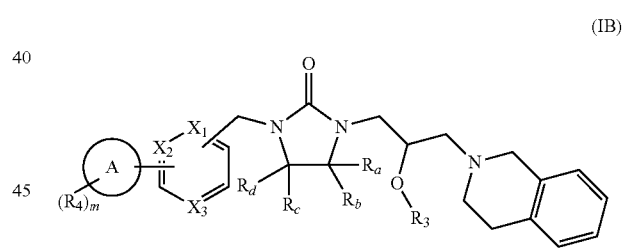

(IB)

or a pharmaceutically acceptable salt thereof or a stereoisomer thereof.

4. The compound of claim 1, having a compound of formula (IC):

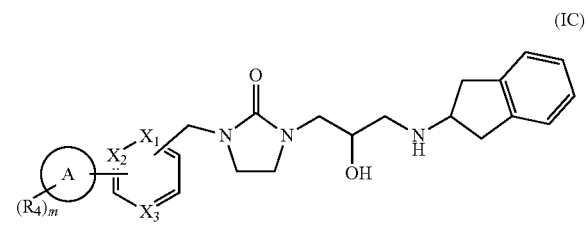

(IC)

or a pharmaceutically acceptable salt thereof or a stereoisomer thereof.

5. The compound of claim 1, having a compound of formula (ID):

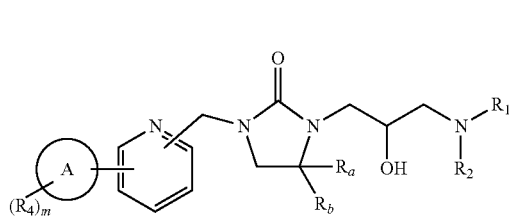

(ID)

or a pharmaceutically acceptable salt thereof or a stereoisomer thereof.

6. The compound of claim 1, having a compound of formula (IE):

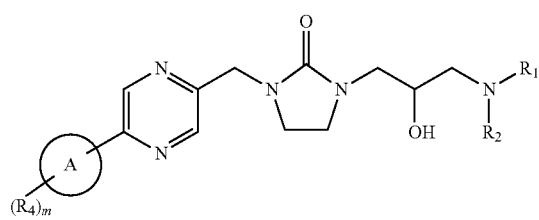

(IE)

or a pharmaceutically acceptable salt thereof or a stereoisomer thereof.

7. The compound of claim 1, having a compound of formula (IF):

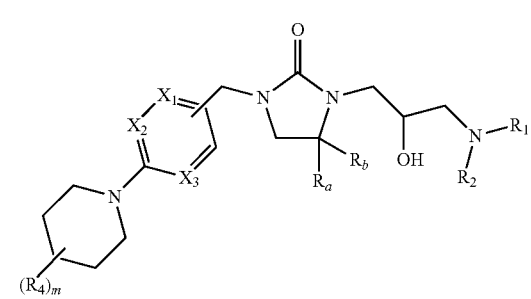

(IF)

or a pharmaceutically acceptable salt thereof or a stereoisomer thereof.

8. The compound of claim 1, having a compound of formula (IG) or (IH):

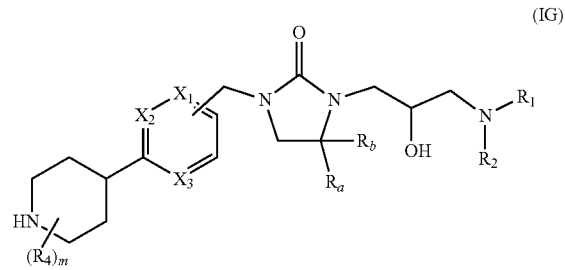

(IG)

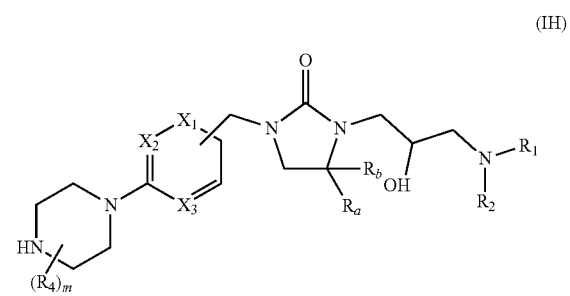

(IH)

or a pharmaceutically acceptable salt thereof or a stereoisomer thereof.

9. The compound of claim 1, having a compound of formula (IJ) or (IK):

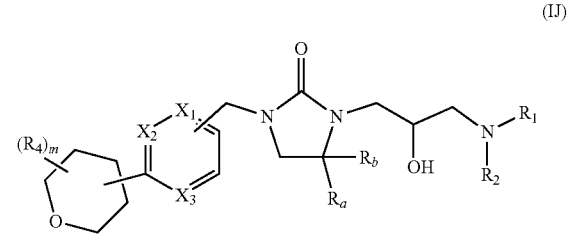

(IJ)

(IK)

or a pharmaceutically acceptable salt thereof or a stereoisomer thereof.

10. The compound of claim 1, having a compound of formula (IL):

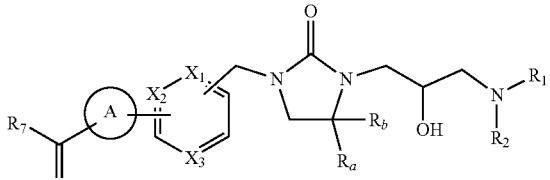

(IL)

or a pharmaceutically acceptable salt thereof or a stereoisomer thereof.

11. The compound of claim 1, wherein, ring

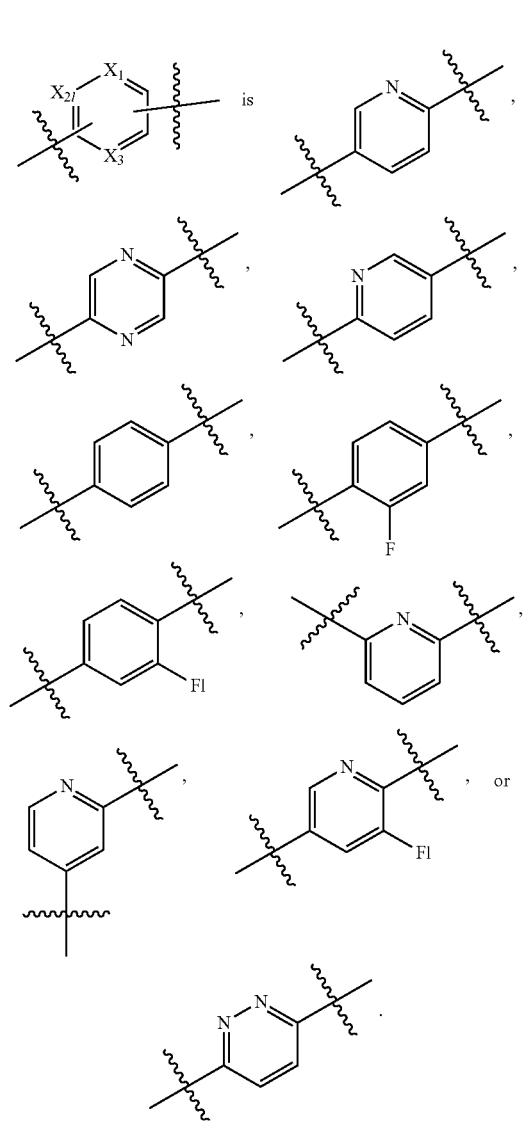

12. The compound of claim 1 wherein, ring A is a 3-10 membered monocyclic ring system.

13. The compound of claim 1 wherein, ring A is a 6-12 membered bicyclic ring selected from fused, bridged and spirocyclic ring systems.

14. The compound of claim 1 wherein, ring A is

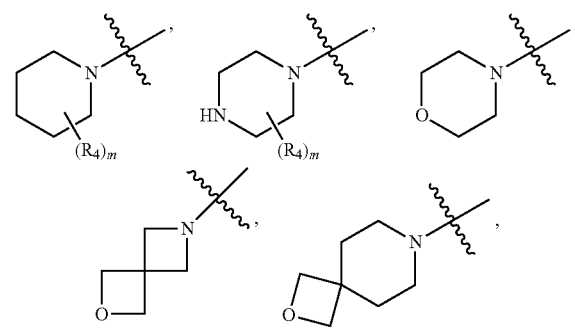

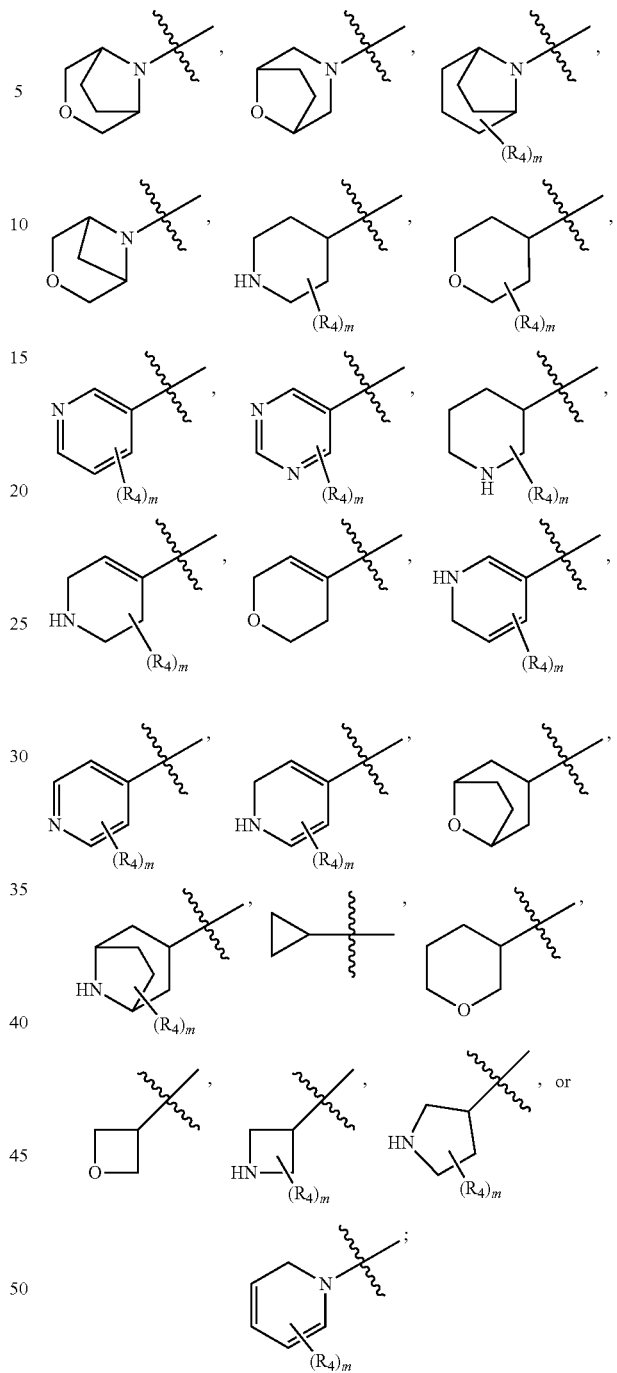

wherein ⁓ is the point of attachment with ring having $X_1$, $X_2$ and $X_3$.

15. The compound of claim 1 wherein, each $X_1$, $X_2$ and $X_3$ are $CR_5$; or $X_1$ is N; $X_2$ and $X_3$ are $CR_5$; or $X_2$ is N; $X_1$ and $X_3$ are $CR_5$; or $X_1$ is $CR_5$; $X_2$ and $X_3$ are N; or $X_2$ is $CR_5$; $X_1$ and $X_3$ are N; or $X_3$ is $CR_5$; $X_1$ and $X_2$ are N.

16. The compound of claim 1 wherein, the group

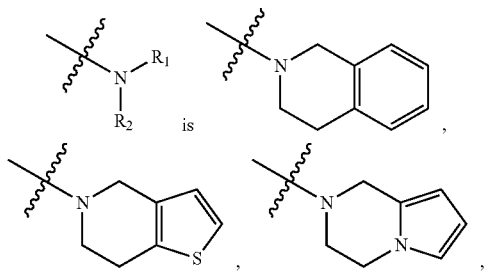 is 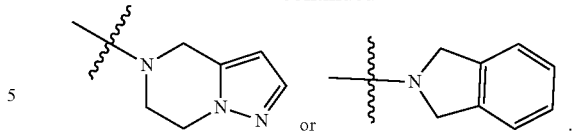 or

17. The compound of claim 1 wherein, $R_3$, $R_a$, $R_b$, $R_c$ and $R_d$ are hydrogen.

18. The compound of claim 1 selected from:

| Comp. No | IUPAC Name |
|---|---|
| 1 | (R)-1-(3-(3,4-dihydroisoquinolin-2(1H)-yl)-2-hydroxypropyl)-3-((5-(4-(pyrrolidine-1-carbonyl)piperidin-1-yl)pyridin-2-yl)methyl)imidazolidin-2-one; |
| 2 | (R)-1-((5-(4-acetylpiperazin-1-yl)pyrazin-2-yl)methyl)-3-(3-(3,4-dihydroisoquinolin-2(1H)-yl)-2-hydroxypropyl)imidazolidin-2-one; |
| 3 | (R)-1-((5-(4-acetylpiperazin-1-yl)pyridin-2-yl)methyl)-3-(3-(3,4-dihydroisoquinolin-2(1H)-yl)-2-hydroxypropyl)imidazolidin-2-one; |
| 4 | (R)-1-(3-(3,4-dihydroisoquinolin-2(1H)-yl)-2-hydroxypropyl)-3-((5-morpholinopyridin-2-yl)methyl)imidazolidin-2-one; |
| 5 | (R)-1-((5-(2-oxa-6-azaspiro[3.3]heptan-6-yl)pyridin-2-yl)methyl)-3-(3-(3,4-dihydroisoquinolin-2(1H)-yl)-2-hydroxypropyl)imidazolidin-2-one; |
| 6 | (R)-1-((5-(4-(cyclopropanecarbonyl)piperazin-1-yl)pyridin-2-yl)methyl)-3-(3-(3,4-dihydroisoquinolin-2(1H)-yl)-2-hydroxypropyl)imidazolidin-2-one; |
| 7 | (R)-1-((5-(4-acetylpiperidin-1-yl)pyrazin-2-yl)methyl)-3-(3-(3,4-dihydroisoquinolin-2(1H)-yl)-2-hydroxypropyl)imidazolidin-2-one; |
| 8 | (R)-1-((5-(4-(cyclopropanecarbonyl)piperazin-1-yl)pyrazin-2-yl)methyl)-3-(3-(3,4-dihydroisoquinolin-2(1H)-yl)-2-hydroxypropyl)imidazolidin-2-one; |
| 9 | (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carbonitrile; |
| 10 | (R)-1-(5-((3-(3-(3,4-dihydroisoquinolin-2(1H)-yl)-2-hydroxypropyl)-2-oxoimidazolidin-1-yl)methyl)pyrazin-2-yl)piperidine-4-carbonitrile; |
| 11 | (R)-1-((5-(4-acetylpiperidin-1-yl)pyridin-2-yl)methyl)-3-(3-(3,4-dihydroisoquinolin-2(1H)-yl)-2-hydroxypropyl)imidazolidin-2-one; |
| 12 | (R)-1-((5-(2-oxa-7-azaspiro[3.5]nonan-7-yl)pyridin-2-yl)methyl)-3-(3-(3,4-dihydroisoquinolin-2(1H)-yl)-2-hydroxypropyl)imidazolidin-2-one; |
| 13 | ethyl(R)-2-(1-(6-((3-(3-(3,4-dihydroisoquinolin-2(1H)-yl)-2-hydroxypropyl)-2-oxoimidazolidin-1-yl)methyl)pyridin-3-yl)piperidin-4-yl)-2-methylpropanoate; |
| 14 | (R)-2-(1-(6-((3-(3-(3,4-dihydroisoquinolin-2(1H)-yl)-2-hydroxypropyl)-2-oxoimidazolidin-1-yl)methyl)pyridin-3-yl)piperidin-4-yl)-2-methylpropanoic acid; |
| 15 | (R)-1-(6-((3-(3-(3,4-dihydroisoquinolin-2(1H)-yl)-2-hydroxypropyl)-2-oxoimidazolidin-1-yl)methyl)pyridin-3-yl)-N,N-dimethylpiperidine-4-sulfonamide; |
| 16 | (R)-1-(5-((3-(3-(3,4-dihydroisoquinolin-2(1H)-yl)-2-hydroxypropyl)-2-oxoimidazolidin-1-yl)methyl)pyridin-2-yl)-N,N-dimethylpiperidine-4-sulfonamide; |
| 17 | (R)-1-(3-(3,4-dihydroisoquinolin-2(1H)-yl)-2-hydroxypropyl)-3-((6-(4-(pyrrolidine-1-carbonyl)piperidin-1-yl)pyridin-3-yl)methyl)imidazolidin-2-one; |
| 18 | 1-((5-(3-oxa-8-azabicyclo[3.2.1]octan-8-yl)pyridin-2-yl)methyl)-3-((R)-3-(3,4-dihydroisoquinolin-2(1H)-yl)-2-hydroxypropyl)imidazolidin-2-one; |
| 19 | 1-((5-(3-oxa-8-azabicyclo[3.2.1]octan-8-yl)pyridin-2-yl)methyl)-3-((R)-3-(3,4-dihydroisoquinolin-2(1H)-yl)-2-hydroxypropyl)imidazolidin-2-one; |
| 20 | 1-((5-((3R,5S)-4-acetyl-3,5-dimethylpiperazin-1-yl)pyridin-2-yl)methyl)-3-((R)-3-(3,4-dihydroisoquinolin-2(1H)-yl)-2-hydroxypropyl)imidazolidin-2-one; |
| 21 | 1-((5-(4-acetyl-2-methylpiperazin-1-yl)pyridin-2-yl)methyl)-3-((R)-3-(3,4-dihydroisoquinolin-2(1H)-yl)-2-hydroxypropyl)imidazolidin-2-one; |
| 22 | 1-((5-(8-oxa-3-azabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |
| 23 | 1-((6-(8-oxa-3-azabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 24 | 1-((5-(3-oxa-8-azabicyclo[3.2.1]octan-8-yl)pyrazin-2-yl)methyl)-3-((R)-3-(3,4-dihydroisoquinolin-2(1H)-yl)-2-hydroxypropyl)imidazolidin-2-one; |
| 25 | 1-((6-(3,3-difluoro-8-azabicyclo[3.2.1]octan-8-yl)pyridin-3-yl)methyl)-3-((R)-3-(3,4-dihydroisoquinolin-2(1H)-yl)-2-hydroxypropyl)imidazolidin-2-one; |
| 26 | 1-(4-(3-oxa-8-azabicyclo[3.2.1]octan-8-yl)benzyl)-3-((R)-3-(3,4-dihydroisoquinolin-2(1H)-yl)-2-hydroxypropyl)imidazolidin-2-one; |
| 27 | 1-((6-(3-oxa-6-azabicyclo[3.1.1]heptan-6-yl)pyridin-3-yl)methyl)-3-((R)-3-(3,4-dihydroisoquinolin-2(1H)-yl)-2-hydroxypropyl)imidazolidin-2-one; |
| 28 | 1-(4-(3-oxa-8-azabicyclo[3.2.1]octan-8-yl)-3-fluorobenzyl)-3-((R)-3-(3,4-dihydroisoquinolin-2(1H)-yl)-2-hydroxypropyl)imidazolidin-2-one; |
| 29 | 1-((5-(3-oxa-6-azabicyclo[3.1.1]heptan-6-yl)pyridin-2-yl)methyl)-3-((R)-3-(3,4-dihydroisoquinolin-2(1H)-yl)-2-hydroxypropyl)imidazolidin-2-one; |

| Comp. No | IUPAC Name |
|---|---|
| 30 | 1-((5-(3-oxa-8-azabicyclo[3.2.1]octan-8-yl)-3-fluoropyridin-2-yl)methyl)-3-((R)-3-(3,4-dihydroisoquinolin-2(1H)-yl)-2-hydroxypropyl)imidazolidin-2-one; |
| 31 | 1-(4-(3-oxa-8-azabicyclo[3.2.1]octan-8-yl)-2-fluorobenzyl)-3-((R)-3-(3,4-dihydroisoquinolin-2(1H)-yl)-2-hydroxypropyl)imidazolidin-2-one; |
| 32 | (R)-1-((6-(1-acetylpiperidin-4-yl)pyridin-3-yl)methyl)-3-(3-(3,4-dihydroisoquinolin-2(1H)-yl)-2-hydroxypropyl)imidazolidin-2-one; |
| 33 | (R)-1-((5-(1-acetylpiperidin-4-yl)pyridin-2-yl)methyl)-3-(3-(3,4-dihydroisoquinolin-2(1H)-yl)-2-hydroxypropyl)imidazolidin-2-one; |
| 34 | (R)-1-((5-(1-acetylpiperidin-4-yl)pyrazin-2-yl)methyl)-3-(3-(3,4-dihydroisoquinolin-2(1H)-yl)-2-hydroxypropyl)imidazolidin-2-one; |
| 35 | (R)-1-(3-(3,4-dihydroisoquinolin-2(1H)-yl)-2-hydroxypropyl)-3-((5-(tetrahydro-2H-pyran-4-yl)pyridin-2-yl)methyl)imidazolidin-2-one; |
| 36 | (R)-1-((5-(1-(cyclopropanecarbonyl)piperidin-4-yl)pyridin-2-yl)methyl)-3-(3-(3,4-dihydroisoquinolin-2(1H)-yl)-2-hydroxypropyl)imidazolidin-2-one; |
| 37 | (R)-1-(3-(3,4-dihydroisoquinolin-2(1H)-yl)-2-hydroxypropyl)-3-((5-(pyridin-3-yl)pyrazin-2-yl)methyl)imidazolidin-2-one; |
| 38 | (R)-1-((6-(1-acetylpiperidin-4-yl)pyridazin-3-yl)methyl)-3-(3-(3,4-dihydroisoquinolin-2(1H)-yl)-2-hydroxypropyl)imidazolidin-2-one; |
| 39 | 1-((5-(1-acetylpiperidin-4-yl)pyridin-2-yl)methyl)-3-(3-(3,4-dihydroisoquinolin-2(1H)-yl)-2-hydroxypropyl)-4,4-dimethylimidazolidin-2-one; |
| 40 | (R)-1-(3-(3,4-dihydroisoquinolin-2(1H)-yl)-2-hydroxypropyl)-3-((5-(tetrahydro-2H-pyran-4-yl)pyrazin-2-yl)methyl)imidazolidin-2-one; |
| 41 | (R)-1-((5-(1-(cyclopropanecarbonyl)piperidin-4-yl)pyrazin-2-yl)methyl)-3-(3-(3,4-dihydroisoquinolin-2(1H)-yl)-2-hydroxypropyl)imidazolidin-2-one; |
| 42 | (R)-1-(3-(3,4-dihydroisoquinolin-2(1H)-yl)-2-hydroxypropyl)-3-((5-(pyrimidin-5-yl)pyridin-2-yl)methyl)imidazolidin-2-one; |
| 43 | (R)-1-(3-(3,4-dihydroisoquinolin-2(1H)-yl)-2-hydroxypropyl)-3-((5-(1-(methylsulfonyl)piperidin-4-yl)pyridin-2-yl)methyl)imidazolidin-2-one; |
| 44 | (R)-1-(3-(3,4-dihydroisoquinolin-2(1H)-yl)-2-hydroxypropyl)-3-((5-(1-propionylpiperidin-4-yl)pyridin-2-yl)methyl)imidazolidin-2-one; |
| 45 | (S)-1-((5-(1-acetylpiperidin-4-yl)pyridin-2-yl)methyl)-3-(3-(3,4-dihydroisoquinolin-2(1H)-yl)-2-hydroxypropyl)imidazolidin-2-one; |
| 46 | 1-((5-(1-acetylpiperidin-3-yl)pyridin-2-yl)methyl)-3-((R)-3-(3,4-dihydroisoquinolin-2(1H)-yl)-2-hydroxypropyl)imidazolidin-2-one; |
| 47 | (R)-1-(3-(3,4-dihydroisoquinolin-2(1H)-yl)-2-hydroxypropyl)-3-((5-(1-methylpiperidin-4-yl)pyridin-2-yl)methyl)imidazolidin-2-one; |
| 48 | (R)-1-((1'-acetyl-1',2',3',6'-tetrahydro-[3,4'-bipyridin]-6-yl)methyl)-3-(3-(3,4-dihydroisoquinolin-2(1H)-yl)-2-hydroxypropyl)imidazolidin-2-one; |
| 49 | (R)-1-((5-(3,6-dihydro-2H-pyran-4-yl)pyridin-2-yl)methyl)-3-(3-(3,4-dihydroisoquinolin-2(1H)-yl)-2-hydroxypropyl)imidazolidin-2-one; |
| 50 | (R)-5-(6-((3-(3-(3,4-dihydroisoquinolin-2(1H)-yl)-2-hydroxypropyl)-2-oxoimidazolidin-1-yl)methyl)pyridin-3-yl)pyrimidine-2-carbonitrile; |
| 51 | (R)-1-(3-(3,4-dihydroisoquinolin-2(1H)-yl)-2-hydroxypropyl)-3-((6-(tetrahydro-2H-pyran-4-yl)pyridazin-3-yl)methyl)imidazolidin-2-one; |
| 52 | (R)-6'-((3-(3-(3,4-dihydroisoquinolin-2(1H)-yl)-2-hydroxypropyl)-2-oxoimidazolidin-1-yl)methyl)-1-methyl-[3,3'-bipyridin]-6(1H)-one; |
| 53 | (R)-1-(3-(3,4-dihydroisoquinolin-2(1H)-yl)-2-hydroxypropyl)-3-((5-(1-(3-methyloxetane-3-carbonyl)piperidin-4-yl)pyridin-2-yl)methyl)imidazolidin-2-one; |
| 54 | (R)-5-(2-((3-(3-(3,4-dihydroisoquinolin-2(1H)-yl)-2-hydroxypropyl)-2-oxoimidazolidin-1-yl)methyl)pyridin-4-yl)pyrimidine-2-carbonitrile; |
| 55 | (R)-5-(6-((3-(3-(3,4-dihydroisoquinolin-2(1H)-yl)-2-hydroxypropyl)-2-oxoimidazolidin-1-yl)methyl)pyridin-2-yl)pyrimidine-2-carbonitrile; |
| 56 | (R)-1-(3-(3,4-dihydroisoquinolin-2(1H)-yl)-2-hydroxypropyl)-3-((2'-hydroxy-[3,4'-bipyridin]-6-yl)methyl)imidazolidin-2-one; |
| 57 | (R)-1-((6-(1-(cyclopropanecarbonyl)piperidin-4-yl)pyridin-3-yl)methyl)-3-(3-(3,4-dihydroisoquinolin-2(1H)-yl)-2-hydroxypropyl)imidazolidin-2-one; |
| 58 | (R)-1-(3-(3,4-dihydroisoquinolin-2(1H)-yl)-2-hydroxypropyl)-3-((2'-methoxy-[2,4'-bipyridin]-5-yl)methyl)imidazolidin-2-one; |
| 59 | (R)-1-(3-(3,4-dihydroisoquinolin-2(1H)-yl)-2-hydroxypropyl)-3-((2'-methoxy-[2,4'-bipyridin]-5-yl)methyl)imidazolidin-2-one; |
| 60 | (R)-1-(3-(3,4-dihydroisoquinolin-2(1H)-yl)-2-hydroxypropyl)-3-((6'-methoxy-[2,3'-bipyridin]-5-yl)methyl)imidazolidin-2-one; |
| 61 | (R)-6'-((3-(3-(3,4-dihydroisoquinolin-2(1H)-yl)-2-hydroxypropyl)-2-oxoimidazolidin-1-yl)methyl)-[3,3'-bipyridin]-6(1H)-one; |
| 62 | (R)-1-(3-(3,4-dihydroisoquinolin-2(1H)-yl)-2-hydroxypropyl)-3-((6'-methoxy-[3,3'-bipyridin]-6-yl)methyl)imidazolidin-2-one; |
| 63 | (R)-5-((3-(3-(3,4-dihydroisoquinolin-2(1H)-yl)-2-hydroxypropyl)-2-oxoimidazolidin-1-yl)methyl)-[2,3'-bipyridin]-6'(1'H)-one; |
| 64 | (R)-1-(3-(3,4-dihydroisoquinolin-2(1H)-yl)-2-hydroxypropyl)-3-((2'-isopropoxy-[3,4'-bipyridin]-6-yl)methyl)imidazolidin-2-one; |
| 65 | (R)-6-((3-(3-(3,4-dihydroisoquinolin-2(1H)-yl)-2-hydroxypropyl)-2-oxoimidazolidin-1-yl)methyl)-1'-methyl-[3,4'-bipyridin]-2'(1'H)-one; |
| 66 | 1-((5-(8-oxabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |

| Comp. No | IUPAC Name |
| --- | --- |
| 67 | (R)-1-(3-(3,4-dihydroisoquinolin-2(1H)-yl)-2-hydroxypropyl)-3-((2'-isopropoxy-[2,4'-bipyridin]-5-yl)methyl)imidazolidin-2-one; |
| 68 | 1-((R)-3-(3,4-dihydroisoquinolin-2(1H)-yl)-2-hydroxypropyl)-3-((5-(3-methyltetrahydro-2H-pyran-4-yl)pyridin-2-yl)methyl)imidazolidin-2-one; |
| 69 | (R)-5-((3-(3-(3,4-dihydroisoquinolin-2(1H)-yl)-2-hydroxypropyl)-2-oxoimidazolidin-1-yl)methyl)-1'-methyl-[2,4'-bipyridin]-2'(1'H)-one; |
| 70 | 1-((R)-3-(3,4-dihydroisoquinolin-2(1H)-yl)-2-hydroxypropyl)-3-((6-(3-methyltetrahydro-2H-pyran-4-yl)pyridin-3-yl)methyl)imidazolidin-2-one; |
| 71 | 1-((R)-3-(3,4-dihydroisoquinolin-2(1H)-yl)-2-hydroxypropyl)-3-((6-(3-methyltetrahydro-2H-pyran-4-yl)pyridin-3-yl)methyl)imidazolidin-2-one; |
| 72 | 1-((5-(8-acetyl-8-azabicyclo[3.2.1]octan-3-yl)pyridin-2-yl)methyl)-3-((R)-3-(3,4-dihydroisoquinolin-2(1H)-yl)-2-hydroxypropyl)imidazolidin-2-one; |
| 73 | 1-((6-(8-acetyl-8-azabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 74 | 1-((6-(8-oxabicyclo[3.2.1]octan-3-yl)pyridin-3-yl)methyl)-3-((R)-3-(3,4-dihydroisoquinolin-2(1H)-yl)-2-hydroxypropyl)imidazolidin-2-one; |
| 75 | 1-((6-cyclopropylpyridin-3-yl)methyl)-3-(3-(3,4-dihydroisoquinolin-2(1H)-yl)-2-hydroxypropyl)imidazolidin-2-one; |
| 76 | 3-((6-cyclopropylpyridin-3-yl)methyl)-1-(3-(3,4-dihydroisoquinolin-2(1H)-yl)-2-hydroxypropyl)-5,5-dimethylimidazolidine-2,4-dione; |
| 77 | 1-((R)-3-(3,4-dihydroisoquinolin-2(1H)-yl)-2-hydroxypropyl)-3-((5-(tetrahydro-2H-pyran-3-yl)pyridin-2-yl)methyl)imidazolidin-2-one; |
| 78 | (R)-1-(3-(3,4-dihydroisoquinolin-2(1H)-yl)-2-hydroxypropyl)-3-((5-(oxetan-3-yl)pyridin-2-yl)methyl)imidazolidin-2-one; |
| 79 | (R)-1-((5-(1-acetylazetidin-3-yl)pyridin-2-yl)methyl)-3-(3-(3,4-dihydroisoquinolin-2(1H)-yl)-2-hydroxypropyl)imidazolidin-2-one; |
| 80 | 1-((5-(1-acetylpyrrolidin-3-yl)pyridin-2-yl)methyl)-3-((R)-3-(3,4-dihydroisoquinolin-2(1H)-yl)-2-hydroxypropyl)imidazolidin-2-one; |
| 81 | 1-((5-(4-acetylpiperazin-1-yl)pyridin-2-yl)methyl)-3-(3-(8-fluoro-3,4-dihydroisoquinolin-2(1H)-yl)-2-hydroxypropyl)imidazolidin-2-one; |
| 82 | 1-((5-(4-acetylpiperazin-1-yl)pyridin-2-yl)methyl)-3-(3-(6,7-dihydrothieno[3,2-c]pyridin-5(4H)-yl)-2-hydroxypropyl)imidazolidin-2-one; |
| 83 | 1-((5-(4-acetylpiperazin-1-yl)pyridin-2-yl)methyl)-3-(3-(3,4-dihydropyrrolo[1,2-a]pyrazin-2(1H)-yl)-2-hydroxypropyl)imidazolidin-2-one; |
| 84 | 1-((5-(4-acetylpiperazin-1-yl)pyridin-2-yl)methyl)-3-(2-hydroxy-3-(isoindolin-2-yl)propyl)imidazolidin-2-one; |
| 85 | 1-((5-(4-acetylpiperazin-1-yl)pyridin-2-yl)methyl)-3-(3-(6,7-dihydropyrazolo[1,5-a]pyrazin-5(4H)-yl)-2-hydroxypropyl)imidazolidin-2-one; |
| 86 | 1-((5-(3-oxa-8-azabicyclo[3.2.1]octan-8-yl)pyridin-2-yl)methyl)-3-(3-((2,3-dihydro-1H-inden-2-yl)amino)-2-hydroxypropyl)imidazolidin-2-one; |
| 87 | 1-((5-(3-oxa-8-azabicyclo[3.2.1]octan-8-yl)pyridin-2-yl)methyl)-3-(2-hydroxy-3-(quinolin-2-ylamino)propyl)imidazolidin-2-one; |
| 88 | 1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 89 | (R)-1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 90 | (S)-1-(3-((2,3-dihydro-1H-inden-2-yl)amino)-2-hydroxypropyl)-3-((5-(tetrahydro-2H-pyran-4-yl)pyridin-2-yl)methyl)imidazolidin-2-one; |
| 91 | 5-(6-((3-(3-(6,7-dimethoxy-3,4-dihydroisoquinolin-2(1H)-yl)-2-hydroxypropyl)-2-oxoimidazolidin-1-yl)methyl)pyridin-3-yl)pyrimidine-2-carbonitrile; |
| 92 | 5-(6-((3-(3-((2,3-dihydro-1H-inden-2-yl)amino)-2-hydroxypropyl)-2-oxoimidazolidin-1-yl)methyl)pyridin-3-yl)pyrimidine-2-carbonitrile; |
| 93 | 1-(3-((2,3-dihydro-1H-inden-5-yl)amino)-2-hydroxypropyl)-3-((5-(tetrahydro-2H-pyran-4-yl)pyridin-2-yl)methyl)imidazolidin-2-one; |
| 94 | 1-(2-hydroxy-3-(naphthalen-2-ylamino)propyl)-3-((5-(tetrahydro-2H-pyran-4-yl)pyridin-2-yl)methyl)imidazolidin-2-one; |
| 95 | (R)-1-(6-((3-(3-(3,4-dihydroisoquinolin-2(1H)-yl)-2-hydroxypropyl)-2-oxoimidazolidin-1-yl)methyl)pyridin-3-yl)piperidine-4-carboxylic acid; |
| 96 | (R)-1-((5-(4-(azetidine-1-carbonyl)piperidin-1-yl)pyridin-2-yl)methyl)-3-(3-(3,4-dihydroisoquinolin-2(1H)-yl)-2-hydroxypropyl)imidazolidin-2-one; |
| 97 | (R)-1-(6-((3-(3-(3,4-dihydroisoquinolin-2(1H)-yl)-2-hydroxypropyl)-2-oxoimidazolidin-1-yl)methyl)pyridin-3-yl)-N,N-dimethylpiperidine-4-carboxamide; |
| 98 | (R)-1-((5-(1-((1H-1,2,3-triazol-4-yl)methyl)piperidin-4-yl)pyridin-2-yl)methyl)-3-(3-(3,4-dihydroisoquinolin-2(1H)-yl)-2-hydroxypropyl)imidazolidin-2-one; |
| 99 | (R)-1-((5-(1-((2H-tetrazol-5-yl)methyl)piperidin-4-yl)pyridin-2-yl)methyl)-3-(3-(3,4-dihydroisoquinolin-2(1H)-yl)-2-hydroxypropyl)imidazolidin-2-one; |
| 100 | (R)-6'-((3-(3-(3,4-dihydroisoquinolin-2(1H)-yl)-2-hydroxypropyl)-2-oxoimidazolidin-1-yl)methyl)-2-oxo-2H-[1,3'-bipyridine]-4-carbonitrile |
| 101 | (R)-6'-((3-(3-(3,4-dihydroisoquinolin-2(1H)-yl)-2-hydroxypropyl)-2-oxoimidazolidin-1-yl)methyl)-2H-[1,3'-bipyridin]-2-one; |
| 102 | (R)-1-(3-(3,4-dihydroisoquinolin-2(1H)-yl)-2-hydroxypropyl)-3-((5-(2-(pyrrolidine-1-carbonyl)pyrimidin-5-yl)pyridin-2-yl)methyl)imidazolidin-2-one; |

-continued

| Comp. No | IUPAC Name |
|---|---|
| 103 | (R)-1-(3-(3,4-dihydroisoquinolin-2(1H)-yl)-2-hydroxypropyl)-3-((6-(2-(pyrrolidine-1-carbonyl)pyrimidin-5-yl)pyridin-3-yl)methyl)imidazolidin-2-one; and |
| 104 | (R)-1-(3-(3,4-dihydroisoquinolin-2(1H)-yl)-2-methoxypropyl)-3-((5-(tetrahydro-2H-pyran-4-yl)pyridin-2-yl)methyl)imidazolidin-2-one; | or a pharmaceutically acceptable salt or a stereoisomer thereof.

19. A pharmaceutical composition comprising a compound of claim 1, or a pharmaceutically acceptable salt or a stereoisomer thereof and at least one pharmaceutically acceptable carrier or excipient.

* * * * *